US012577605B2

(12) United States Patent
Abate et al.

(10) Patent No.: US 12,577,605 B2
(45) Date of Patent: Mar. 17, 2026

(54) PRINTING DROPLETS CONTAINING BIOLOGICAL MATERIAL

(71) Applicant: The Regents of the University of California, Oakland, CA (US)

(72) Inventors: Adam R. Abate, San Francisco, CA (US); Linfeng Xu, San Francisco, CA (US); Leqian Liu, San Francisco, CA (US); Kai-chun Chang, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 756 days.

(21) Appl. No.: 17/928,198

(22) PCT Filed: May 27, 2021

(86) PCT No.: PCT/US2021/034554
§ 371 (c)(1),
(2) Date: Nov. 28, 2022

(87) PCT Pub. No.: WO2021/243041
PCT Pub. Date: Dec. 2, 2021

(65) Prior Publication Data
US 2023/0212646 A1     Jul. 6, 2023

Related U.S. Application Data

(60) Provisional application No. 63/174,955, filed on Apr. 14, 2021, provisional application No. 63/081,724, (Continued)

(51) Int. Cl.
*B01L 3/00* (2006.01)
*B01D 15/08* (2006.01)
(Continued)

(52) U.S. Cl.
CPC ...... *C12Q 1/6806* (2013.01); *B01L 3/502715* (2013.01); *B01L 3/502784* (2013.01);
(Continued)

(58) Field of Classification Search
CPC .... C12Q 1/6806; C12Q 1/6827; C12Q 1/686; C12Q 2600/156; B01L 3/502715;
(Continued)

(56) References Cited

U.S. PATENT DOCUMENTS

2009/0261243 A1    10/2009  Bamberger et al.
2014/0235464 A1     8/2014  Van Den Boom et al.
(Continued)

FOREIGN PATENT DOCUMENTS

WO        2016065056        4/2016
WO        2019139650        7/2019
WO    WO-2019139650 A2 *    7/2019  ............. A61K 9/127

OTHER PUBLICATIONS

Becht et al. (2018) "Dimensionality reduction for visualizing single-cell data using UMAP" Nature Biotechnology 37: 38-44.
(Continued)

*Primary Examiner* — Jennifer Wecker
*Assistant Examiner* — Oyeleye Alexander Alabi
(74) *Attorney, Agent, or Firm* — Edward J. Baba; Bozicevic, Field & Francis LLP

(57) ABSTRACT

Provided is a method including encapsulating a biological material in a droplet having a volume of 500 nl or less, depositing the droplet to an addressable location of a substrate, and performing mass spectroscopy on the droplet. The method can further include conducting omic analysis on the droplet, such as sequencing DNA or analyzing mRNA, after the mass spectroscopy. In some cases, the method can be used to screen thousands of genetically different cells to identify correlations between genetics and the production of
(Continued)

a metabolite, wherein the metabolite is detected by mass spectroscopy. Also provided is a system for performing the method.

41 Claims, 38 Drawing Sheets

Related U.S. Application Data filed on Sep. 22, 2020, provisional application No. 63/031,750, filed on May 29, 2020.

(51) Int. Cl.

| | |
|---|---|
| *B01F 33/302* | (2022.01) |
| *B01F 33/3033* | (2022.01) |
| *B01J 20/285* | (2006.01) |
| *B01J 20/287* | (2006.01) |
| *B01J 20/32* | (2006.01) |
| *B01L 7/00* | (2006.01) |
| *B01L 9/00* | (2006.01) |
| *B65G 47/80* | (2006.01) |
| *B82Y 20/00* | (2011.01) |
| *B82Y 30/00* | (2011.01) |
| *B82Y 40/00* | (2011.01) |
| *C12M 1/34* | (2006.01) |
| *C12M 3/06* | (2006.01) |
| *C12N 1/14* | (2006.01) |
| *C12N 1/20* | (2006.01) |
| *C12Q 1/02* | (2006.01) |
| *C12Q 1/6806* | (2018.01) |
| *C12Q 1/6827* | (2018.01) |
| *C12Q 1/6844* | (2018.01) |
| *C12Q 1/6848* | (2018.01) |
| *C12Q 1/686* | (2018.01) |
| *G01N 15/10* | (2024.01) |
| *G01N 15/14* | (2024.01) |
| *G01N 15/1433* | (2024.01) |
| *G01N 21/29* | (2006.01) |
| *G01N 21/33* | (2006.01) |
| *G01N 21/64* | (2006.01) |
| *G01N 21/65* | (2006.01) |
| *G01N 21/76* | (2006.01) |
| *G01N 30/02* | (2006.01) |
| *G01N 30/60* | (2006.01) |
| *G01N 30/72* | (2006.01) |
| *G01N 33/00* | (2006.01) |
| *G01N 33/50* | (2006.01) |
| *G01N 33/543* | (2006.01) |
| *G01N 33/557* | (2006.01) |
| *G01N 33/574* | (2006.01) |
| *G01N 33/58* | (2006.01) |
| *G01N 33/68* | (2006.01) |
| *G01N 35/00* | (2006.01) |
| *H05B 45/10* | (2020.01) |

(52) U.S. Cl.

CPC ........... *C12Q 1/6827* (2013.01); *C12Q 1/686* (2013.01); *B01L 2200/027* (2013.01); *B01L 2200/16* (2013.01); *B01L 2300/0636* (2013.01); *B01L 2300/0816* (2013.01); *B01L 2300/0861* (2013.01); *C12Q 2600/156* (2013.01)

(58) Field of Classification Search

CPC ......... B01L 3/502784; B01L 2200/027; B01L 2200/16; B01L 2300/0636; B01L 2300/0816; B01L 2300/0861; G01N 33/6842; G01N 33/6848; A61K 9/501

See application file for complete search history.

(56) References Cited

U.S. PATENT DOCUMENTS

| | | | |
|---|---|---|---|
| 2018/0056288 A1* | 3/2018 | Abate | ................ G01N 15/1484 |
| 2018/0369818 A1 | 12/2018 | Kiani et al. | |
| 2020/0122135 A1 | 4/2020 | Abate et al. | |

OTHER PUBLICATIONS

Cole et al. (2017) "Printed droplet microfluidics for on demand dispensing of picoliter droplets and cells" PNAS 114:33 8728-8733.

Jez et al. (2000) "Structural control of polyketide formation in plant-specific polyketide synthases" Cell Chemical Biology 7:12 919-930.

Jindaprasert et al (2008) "Pyrone polyketides synthesized by a type III polyketide synthase from Drosophyllum lusitanicum" Pytochemistry 69: 3043-3053.

Markham et al. (2018) "Rewiring Yarrowia lipolytica toward triacetic acid lactone for materials generation" PNAS 115:9 2096-2101.

Si et al. (2017) "Profiling of Microbial Colonies for High-Throughput Engineering of Multistep Enzymatic Reactions via Optically Guided Matrix-Assisted Laser Desorption/Ionization Mass Spectrometry" Journal of the American Chemical Society, 139: 12466-12473.

Tebani et al. (2020) "Integration of molecular profiles in a longitudinal wellness profiling cohort" Nature Communications 11: 4487, 14 pages.

Haidas Dominik et al. (2020) "Parallel Sampling of Nanoliter Droplet Arrays for Noninvasive Protein Analysis in Discrete Yeast Cultivations by MALDI-MS" vol. 92, No. 5, Jan. 28, 2020.

Kazdal Daniel et al, (2018) "Digital PCT After Maldi-Mass Spectrometry Imaging to Combine Proteomic Mapping and Identification of Activating Mutations in Pulmonary Adenocarcinoma" Proteomics Clinical Applications, vol. 13, No. 1, Oct. 15, 2018.

* cited by examiner

FIG. 1

| Power 150 126 | 0.5 | 0.4 | 0.3 | 0.2 | 0.1 | 0 | Blank |
|---|---|---|---|---|---|---|---|
| AVEsignal | 15.5 | 11.0 | 6.9 | 3.0 | 0.6 | 0.2 | 0.0 |
| CV | 0.7 | 0.0 | 1.0 | 2.5 | 0.1 | 0.1 | 0.0 |
| CV % | 4.6 | 0.0 | 14.3 | 84.9 | 12.9 | 47.1 | 0.0 |

| Library | # of microwells | Percentage |
|---|---|---|
| Positive | 101 | 19.8% |
| Negative | 410 | 80.2% |

①  *S. Cer.* with 350 µg/mL Naringenin production
②  *S. Cer.* with 350 µg/mL Naringenin production 10 fold dilution
③  *S. Cer.* with 350 µg/mL Naringenin production 100 fold dilution
④  *S. Cer.* with 350 µg/mL Naringenin production 1000 fold dilution
⑤  *S. Cer.* with 50 µg/mL Naringenin production

FIG. 6

Electropherogram Summary Continued ...

Library prep

FIG. 7 (Cont.)

| "21S_RRNA" | 2971 | 2347 | 1371 | 1332 | 1396 | 935 | 1333 |
|---|---|---|---|---|---|---|---|
| "Q0050" | 559 | 558 | 342 | 300 | 357 | 190 | 162 |
| "15S_RRNA" | 585 | 660 | 247 | 265 | 293 | 172 | 139 |
| "Q0055" | 131 | 112 | 48 | 57 | 73 | 37 | 26 |
| "OLI1" | 48 | 45 | 36 | 35 | 38 | 17 | 28 |
| "YMR251W... | 76 | 40 | 28 | 32 | 22 | 16 | 10 |
| "HSP12" | 56 | 45 | 32 | 26 | 13 | 20 | 7 |
| "AI4" | 46 | 26 | 18 | 17 | 17 | 13 | 20 |
| "YMR175W" | 31 | 22 | 10 | 8 | 11 | 17 | 0 |
| "YHR162W" | 22 | 18 | 16 | 10 | 6 | 7 | 4 |
| "SCEI" | 13 | 8 | 7 | 8 | 12 | 6 | 4 |
| "HSP82" | 23 | 10 | 11 | 7 | 6 | 5 | 2 |
| "YNR034W-... | 15 | 14 | 3 | 8 | 1 | 3 | 0 |
| "YBR072W" | 16 | 9 | 13 | 4 | 4 | 5 | 1 |
| "SOD1" | 12 | 6 | 3 | 6 | 3 | 5 | 1 |
| "HMRA1" | 13 | 4 | 5 | 6 | 1 | 8 | 3 |
| "Q0070" | 19 | 11 | 4 | 6 | 1 | 0 | 3 |
| "ATP6" | 12 | 6 | 6 | 3 | 5 | 3 | 0 |
| "YLL026W" | 9 | 14 | 7 | 2 | 5 | 4 | 0 |
| "YPR036W... | 13 | 17 | 11 | 4 | 4 | 4 | 0 |
| "YGR142W" | 8 | 9 | 5 | 3 | 6 | 2 | 2 |
| "Q0110" | 18 | 6 | 6 | 2 | 5 | 3 | 4 |
| "g2ps1" | 2 | 1 | 0 | 0 | 0 | 1 | 0 |
| "snR31" | 1 | 1 | 1 | 0 | 0 | 0 | 0 |

└─Heterologous tricetic acid lactone synthesis gene

Picking based on Mass spec imaging

Push water into the dried microwell

Withdraw water contains yeast cell

After MALDI

After picking

Droplet printing and MALDI MS Imaging

Negative control

Positive control

Mock library

MALDI MS Imaging for m/z 126 ± 0.1

Culture single yeast cells in droplet

Single yeast cultured in droplets for 3 days

Specification of substrate 75 mm by 25 mm slide with 10,000 mircowells (150 um in diameter, 300 um pitches)

75 mm by 25 mm slide with 100,000 mircowells (80 um in diameter, 150 um pitches)

Bowl-shape microwell to enhance MS sensitivity

Push water into the dried mircowell

Withdraw water contains yeast cell

Target gene retrieval after MS ion imaging

Manual retrieval using glass micropipette

Triacetic Acid
Lactone (TAL)
[M + H+] m/z: 127.1

6-acetonyl-4-hydroxy-
2-pyrone (AHP)
[M + H+] m/z: 169.1 a b a b a

*Fluorescent Imaging*

*m/z ion intesity heatmap*

*Quantification*

Spatial map of m/z 127 region signal strength

Spatial map of m/z 169 region signal strength a b c m/z 116.3924
m/z 136.3026
m/z 154.0608
m/z 166.3175
m/z 175.1312
m/z 192.4029
m/z 205.3333
m/z 212.2943
m/z 232.3917
m/z 258.346
m/z 263.4358
m/z 270.3408
m/z 296.2951
m/z 393.1701
m/z 399.3827
m/z 414.5025
m/z 529.5474
m/z 573.5594
m/z 617.5714 e f

PRINTING DROPLETS CONTAINING BIOLOGICAL MATERIAL

CROSS-REFERENCE

This application is a 371 of PCT/US2021/034554 filed May 27, 2021, which claims priority to U.S. Application No. 63/031,750 filed May 29, 2020; and 63/081,724, filed Sep. 22, 2020, and 63/174,955, filed Apr. 14, 2021, which are incorporated herein by reference.

INTRODUCTION

Microbes can be designed and engineered to synthesize a variety of valuable chemicals, including pharmaceuticals, fuels, fabrics, foods and fragrances, and accomplish this at normal temperature and pressure and in aqueous environments. They accomplish these feats using enzymes, biocatalysts that are unmatched in their ability to accelerate chemical transformations with high specificity. To advance microbial bioproduction by improving its production efficiency and expanding its products profile, scientists sometimes identify a novel enzyme or engineer existing enzyme for high specificity and efficacy. For example, enzymes are discovered and engineered to enable the bioproduction of antimalaria drug, the complete biosynthesis of medicinal cannabinoids as well as the production of drop-in jet biofuel. These efforts help advance microbial cell factories to replace traditional chemical synthesis industry with a significantly positive impact on both economics and environment.

The discovery and engineering of biocatalytic enzymes with novel functions have accelerated in recent years with the advance of DNA synthesis and sequencing technologies. Together, they allow comprehensive probing of enzyme sequence-function landscapes to identify enzymes with powerful new abilities. Key to this process is the ability to construct and test massive numbers of enzyme mutants, which typically relies on testing modalities that utilize fluorogenic reporters or chemical assays. Construction of such testing modalities can be complicated, lead to false-discoveries, and is sometimes only applicable to a small fraction of enzymes compatible with the selection or fluorescence assay.

SUMMARY

Provided is a method including encapsulating a biological material in a droplet having a volume of 500 nl or less, depositing the droplet to an addressable location of a substrate, and performing mass spectroscopy on the droplet. The method can further include conducting omic analysis on the droplet, such as sequencing DNA or analyzing mRNA, after the mass spectroscopy. In some cases, the method can be used to screen thousands of genetically different cells to identify correlations between genetics and the production of a metabolite, wherein the metabolite is detected by mass spectroscopy. Also provided is a system for performing the method.

BRIEF DESCRIPTION OF THE DRAWINGS

FIG. 1 shows overall process of the method to combine droplet microfluidics and mass spec imaging with example on the discovery of power biocatalyst by screening a large yeast library.

FIG. 16A shows application of mapping g2ps1 mutant catalysis through metabolite fingerprinting. a, Overview of the coated and etched microscope slide, measuring 75 mm×25 mm, used for droplet printing and MALDI MS imaging. Magnified blue box shows one of the 100-well clusters; further magnified orange box shows a single droplet printed in a well; final green box shows well cross section and depth measured by a polymer impression.

FIG. 16B shows Schematic of how MALDI MS imaging produces metabolites information for each picowell. The heatmap demonstrates the selected m/z signal intensity for each picowell.

Figure 24:
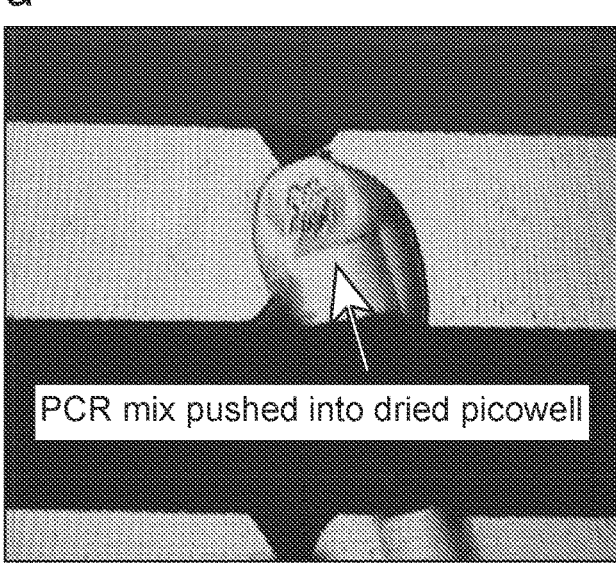
Figure 24:
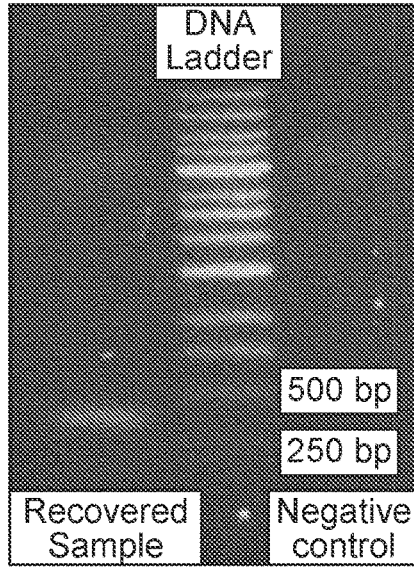

FIG. 24 shows recover cells after MALDI MS ion imaging for mutation sequencing. a, a glass micropipette is used to add a water droplet to the dried yeast in the picowells and then b, this water droplet containing yeast cells is withdraw and transferred to a PCR tube for c, PCR of the mutation site (380 bp) and sanger sequencing.

Figure 25:
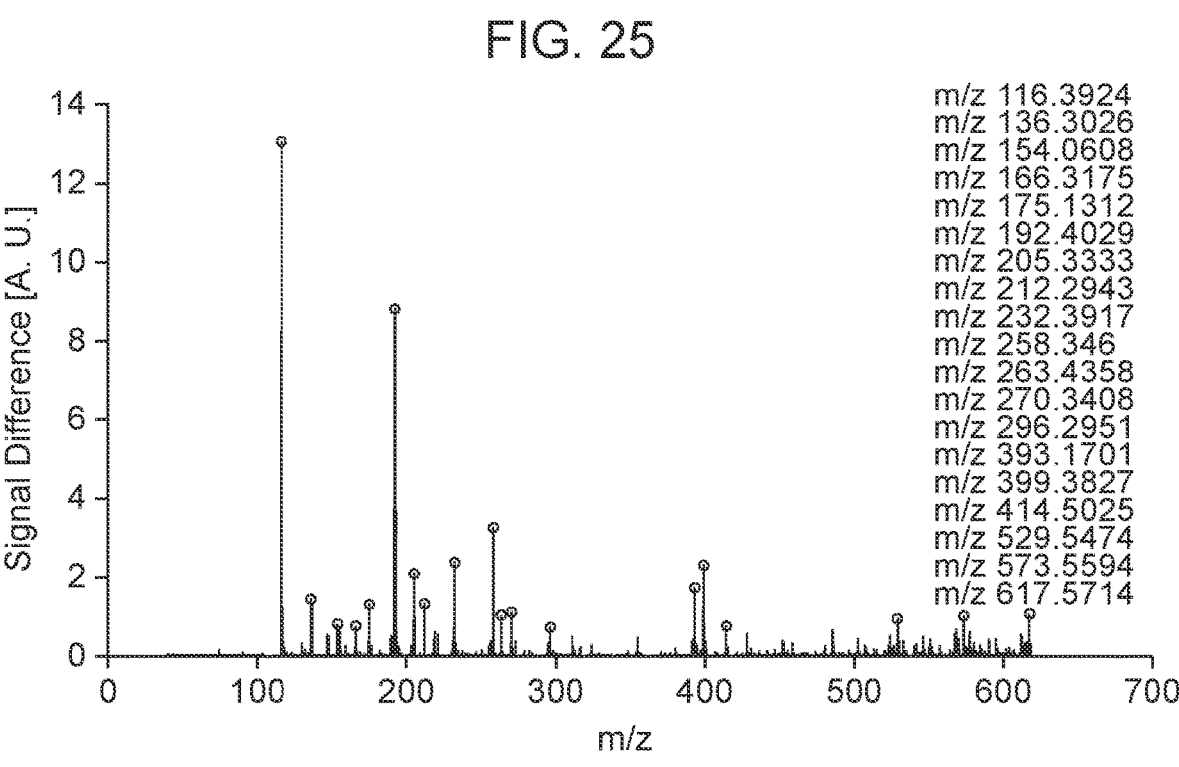

FIG. 25 shows m/z peaks used for UMAP analysis. Based on the positive difference spectrum (red line) between the average m/z signal of the 9000 library picowells and the 1000 reference picowells, the top 19 m/z peaks (black circles) are chosen for UMAP analysis.

Figure 26:
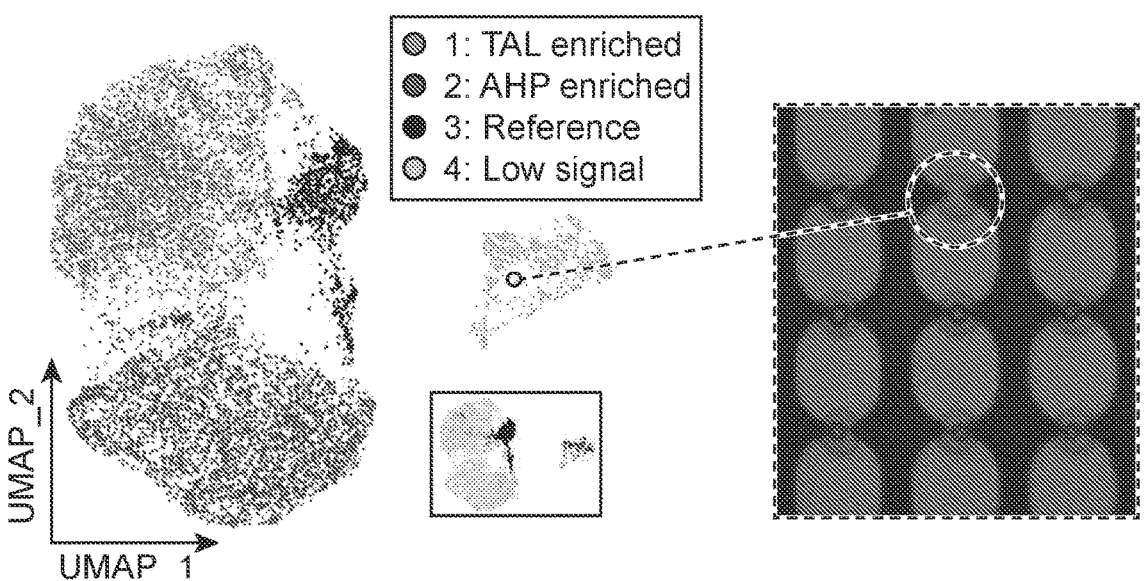

FIG. 26 shows low signal cluster of the UMAP corresponds to empty or near-empty wells. Transillumination imaging of picowell samples clustered within the outlier cluster of the UMAP full of low signal indicates misprints of droplets that lacking cell material.

Figure 27:
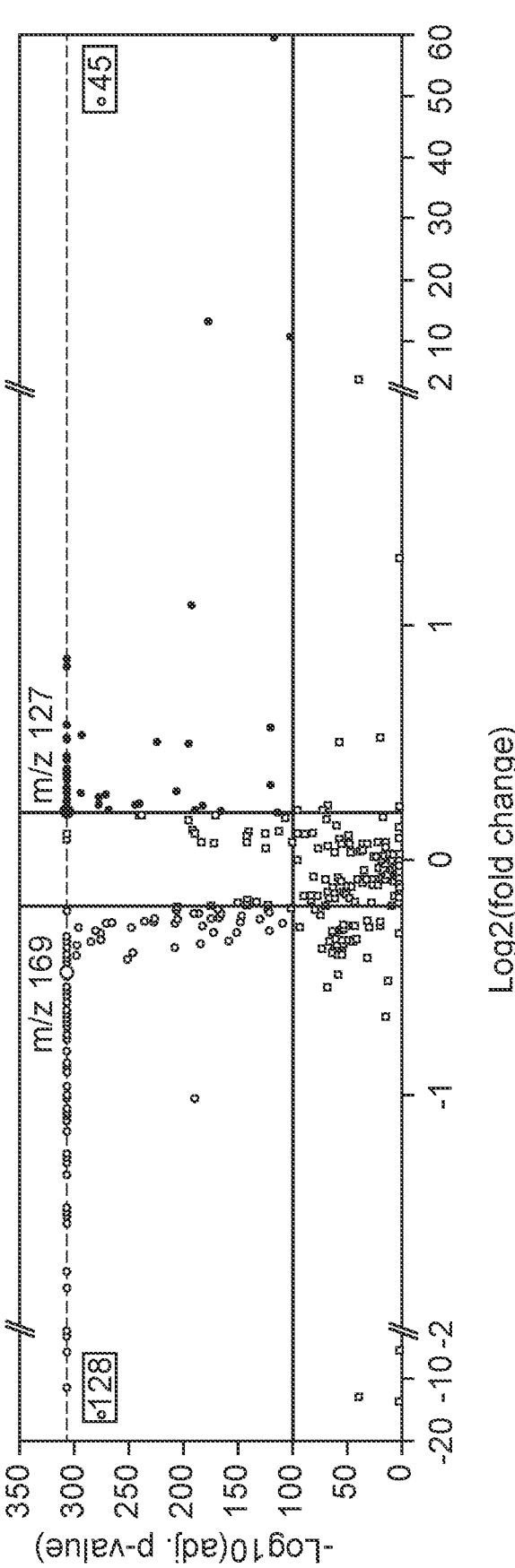

FIG. 27 shows volcano plot between the TAL enriched cluster and AHP enriched cluster to reveal the differential strength of m/z peaks. As expected, TAL (dark red dot, m/z 127) is higher in the TAL enriched cluster while AHP (dark green dot, m/z 169) is more abundant in the AHP enriched cluster, along with dozens of other m/z peaks (128 for green dots and 45 for red dots). The horizontal red line represents the −Log 10(adj. p-value) threshold at 100 and the vertical red lines indicate +/−0.2 threshold values for Log 2 (fold change). Gray dash line indicates the smallest computational value in R for −Log 10 (adj. p-value) at an (adj. p-value) =2.225074E-308.

Figure 28:
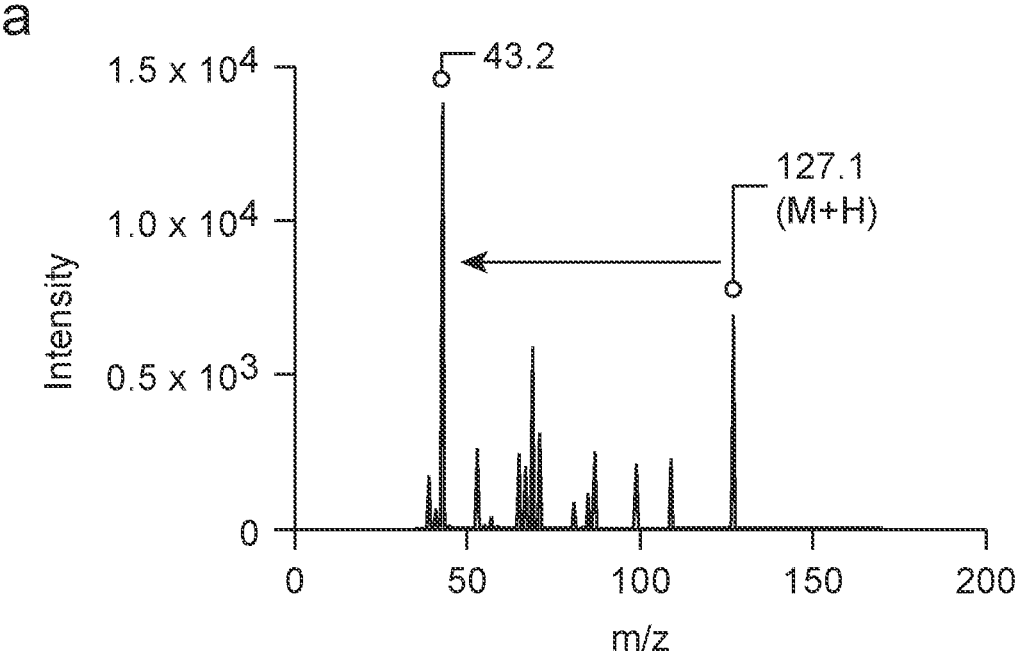
Figure 28:
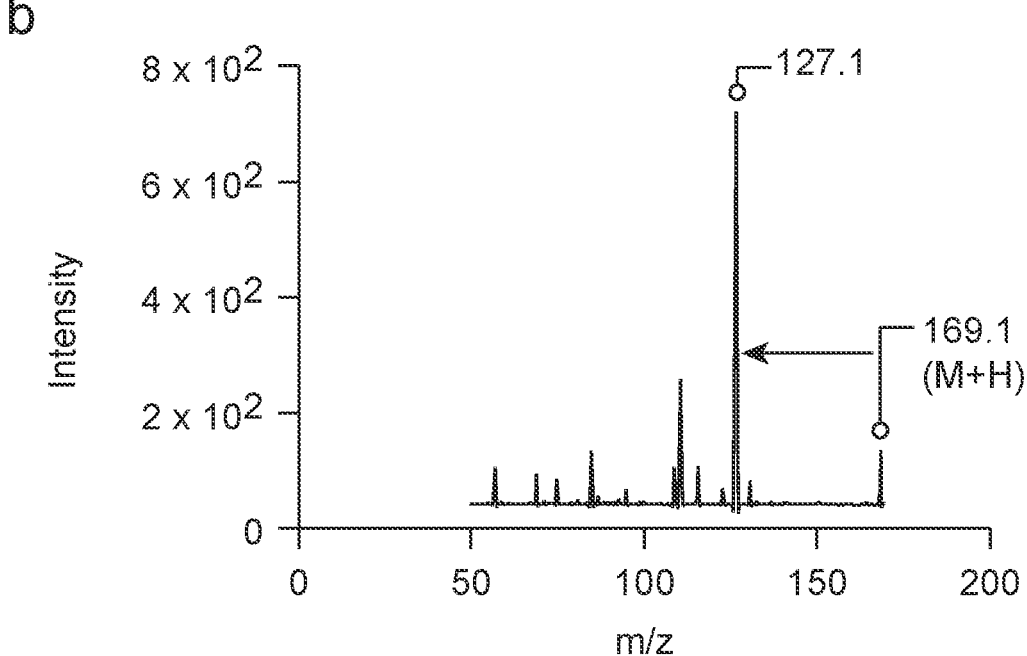
Figure 28:
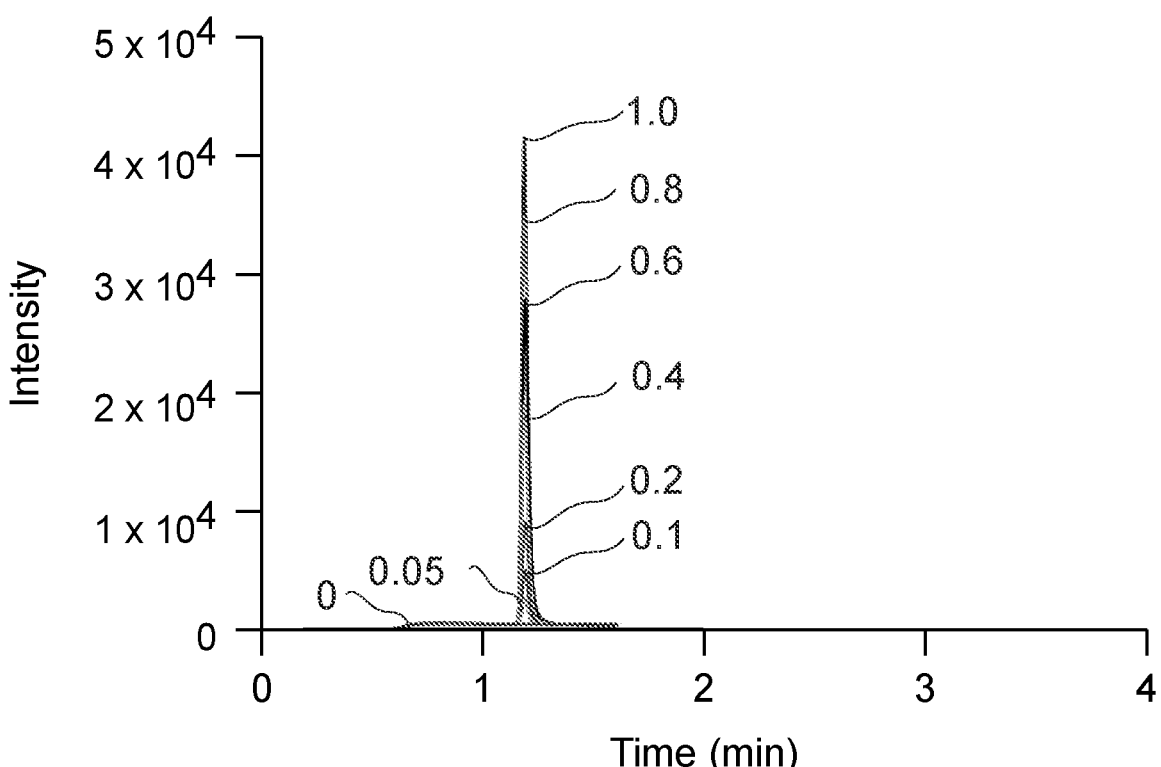
Figure 28:
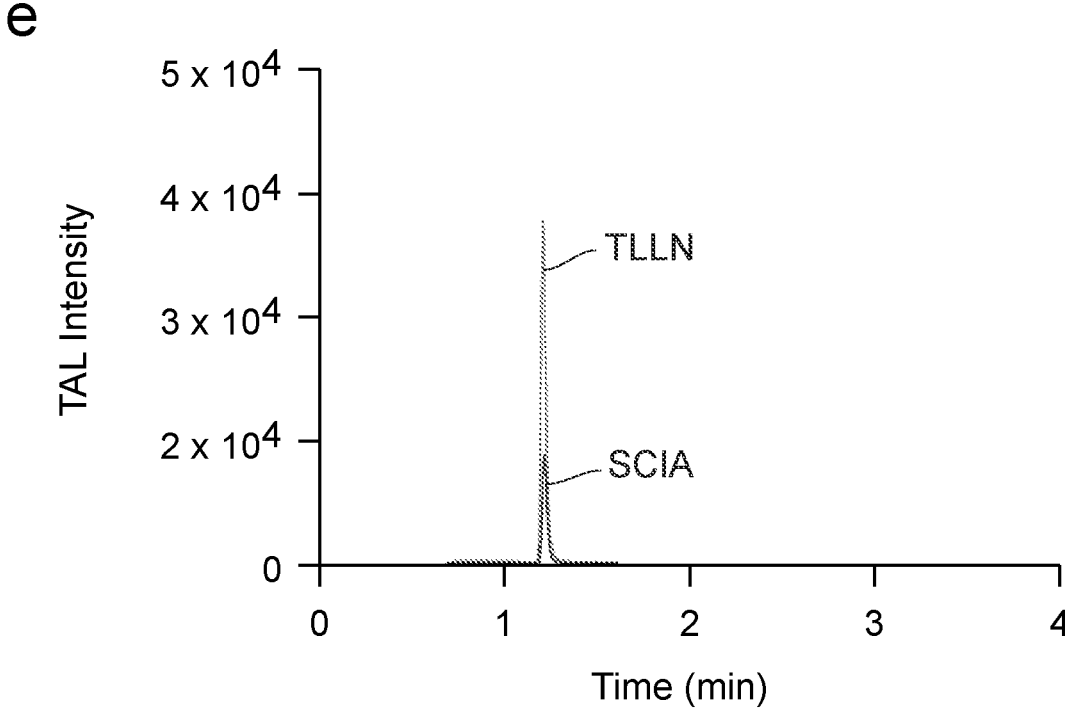
Figure 28:
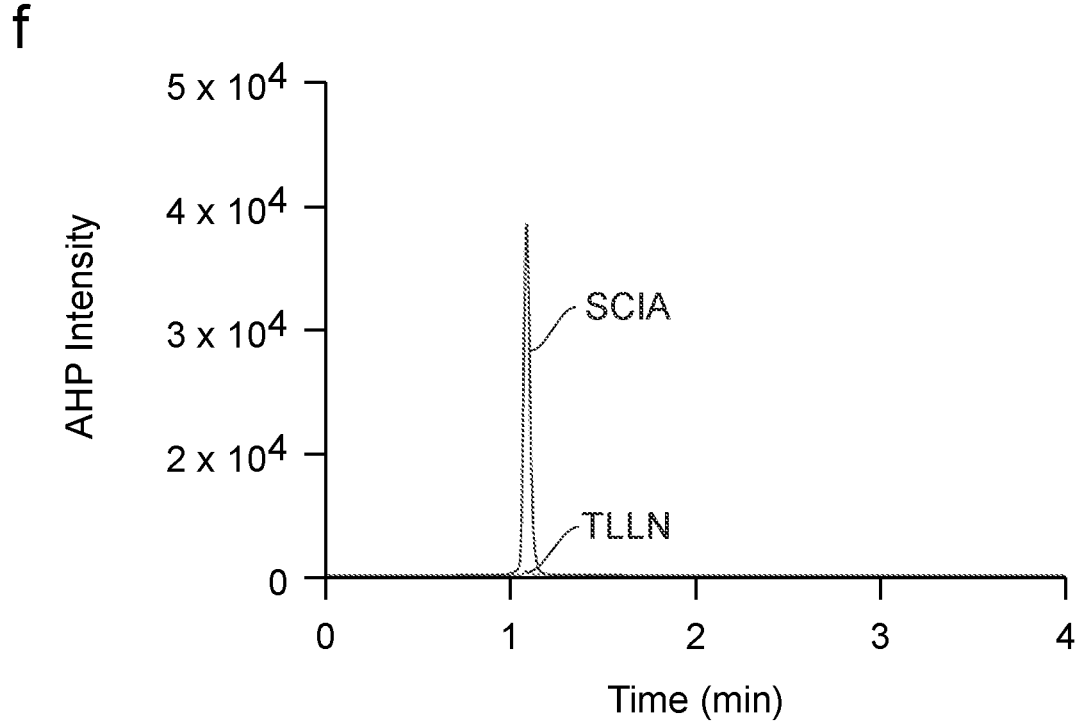

FIG. 28 shows HPLC-MS/MS of *Y. lipolytica* strains recovered from the picowells. a, Product ion mass spectrum of TAL showing intact ion (m/z: 127.1) and most abundant product ion (m/z: 43.2). b, Product ion mass spectrum of AHP showing intact ion (m/z: 169.1) and most abundant product ion (m/z: 127.1). Red arrows in a and b denote monitored mass transitions for HPLC-MS/MS analysis. c, Structures and masses of TAL and AHP, with proposed fragment pattern observed by MS/MS shown with dashed line. d, Overlaid chromatograms of HPLC-MS/MS for TAL calibration samples. Legend titles represent concentration of TAL in mg/mL. e, Overlaid TAL mass chromatograms for SCIA and TLLN mutants. f, Overlaid AHP mass chromatograms for SCIA and TLLN mutants. AHP abundance for TLLN production is too low to detect.

Figure 29:
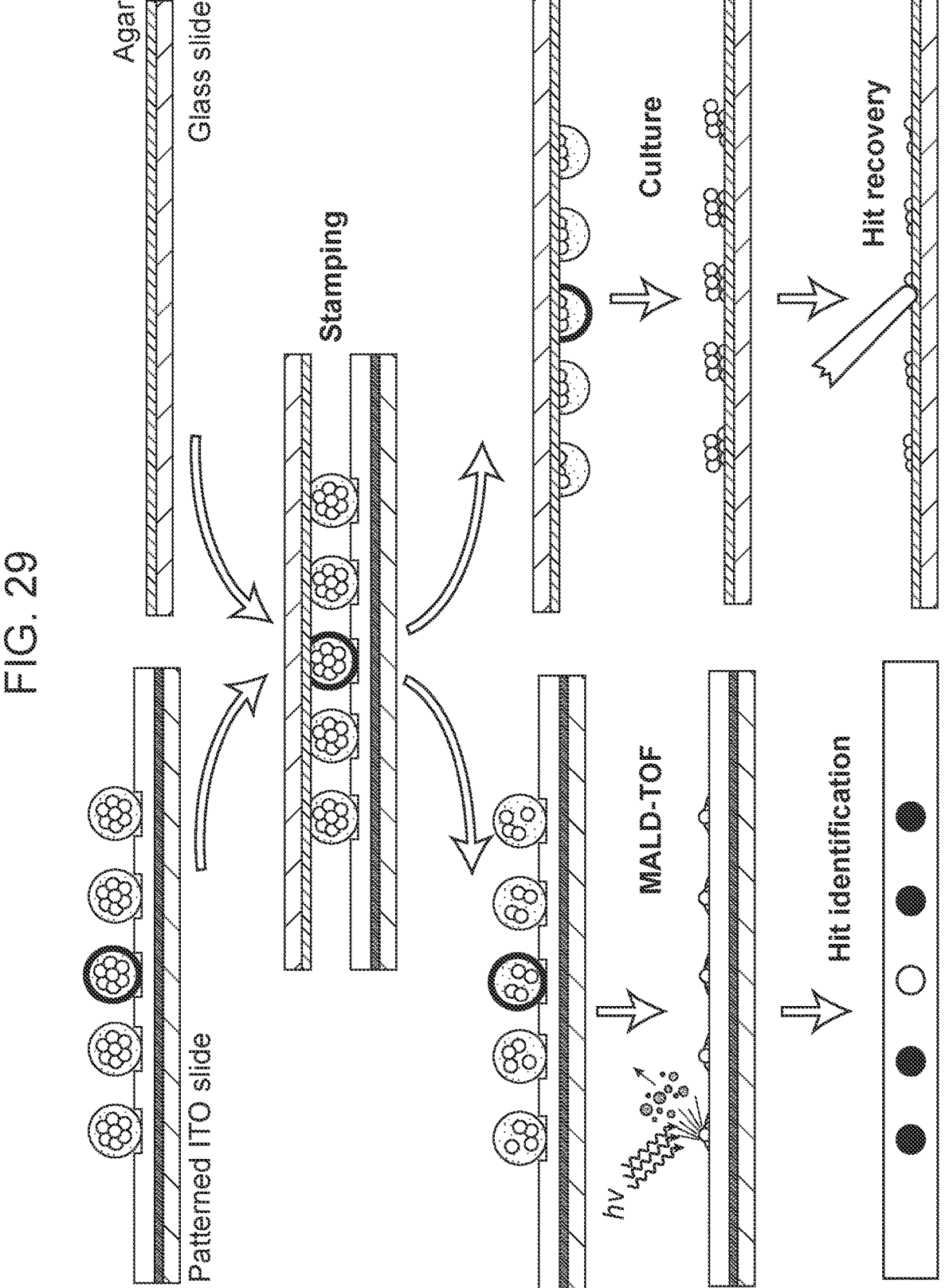

FIG. 29 shows an exemplary method employing the transfer of droplet material to the replicate plate.

DETAILED DESCRIPTION

Provided is a method including encapsulating a biological material in a droplet having a volume of 500 nl or less, depositing the droplet to an addressable location of a substrate, and performing mass spectroscopy on the droplet. The method can further include conducting omic analysis on the droplet, such as sequencing DNA or analyzing mRNA, after the mass spectroscopy. In some cases, the method can be used to screen hundreds of thousands of genetically different cells to identify correlations between genetics and the production of a metabolite, wherein the metabolite is detected by mass spectroscopy. Also provided is a system for performing the method.

Before the present invention is described in greater detail, it is to be understood that this invention is not limited to particular embodiments described, as such may vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and exemplary methods and materials may now be described. Any and all publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a droplet" includes a plurality of such droplets and reference to "the discrete entity" includes reference to one or more discrete entities, and so forth.

It is further noted that the claims may be drafted to exclude any element, e.g., any optional element. As such, this statement is intended to serve as antecedent basis for use of such exclusive terminology as "solely", "only" and the like in connection with the recitation of claim elements, or the use of a "negative" limitation.

The publications discussed herein are provided solely for their disclosure prior to the filing date of the present application. Further, the dates of publication provided may be different from the actual publication dates which may need to be independently confirmed. To the extent the definition or usage of any term herein conflicts with a definition or usage of a term in an application or reference incorporated by reference herein, the instant application shall control.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Definitions

The terms droplet, discrete entity, and microdroplet are used interchangeably herein. Droplet refers to small, generally spherically structures, containing at least a first fluid phase, e.g., an aqueous phase (e.g., water). Droplets according to the present disclosure generally range from 1 μm to 1000 μm, inclusive, in diameter. Droplets according to the present disclosure may be used to encapsulate a single cell, multiple cells, reagents, and a variety of other components. The term droplet may be used to refer to a droplet produced in, on, or by a microfluidic device and/or flowed from or applied by a microfluidic device.

Methods

Provided is a method including encapsulating a biological material in a droplet having a volume of 500 nl or less, depositing the droplet to an addressable location of a substrate, and performing mass spectroscopy on the droplet.

In some cases, the method further includes conducting another analysis, e.g. omic analysis, on the droplet after the performance of the mass spectroscopy. Exemplary omic analyses include genomic analysis, proteomic analysis, metabolomic analysis, and glycomic analysis. Omic analysis includes characterizing the biological molecules that impact the physical structure and metabolism of organisms.

In some cases the omic analysis is genomic analysis, i.e. analyzing the genome of a cell. The genomic analysis can be performed on an intact cell, a lysed cell, or on nucleic acids isolated from a cell or other source. In some cases, the genome is based on DNA. In cases where the biological material is an RNA virus, the genomic analysis assesses RNA.

In some cases the genomic analysis includes aspirating material at the addressable location and moving it to a genomic analysis device. In some cases this involves depositing water at the addressable location, and then aspirating the resulting mixture of water and the material that was already present at the addressable location and moving the mixture to a genomic analysis device. In other cases, the genomic analysis involves assessing the genome while the genetic material is still at the addressable location. In some cases the genomic analysis includes polymerase chain reaction (PCR). In some cases the genomic analysis includes sequencing DNA in the droplet, e.g. from the cell, analyzing mRNA in the droplet, or a combination thereof.

In some cases, the omic analysis is proteomic analysis, i.e. the assessment of proteins present in a biological sample. The proteome is the entire set of proteins that are produced by a particular organism. In some cases, the omic analysis is transcriptomic analysis, i.e. the assessment of the RNA transcripts of a cell. This analysis can only include coding regions RNA, or it can also include non-coding regions of RNA. In some cases the analysis includes only mRNA assessment, but in other cases it can include other types of RNA assessment as well. In some cases, the omic analysis is metabolomic analysis, i.e. the assessment of the metabolites produced by a cell. Metabolomic analysis examines the metabolome of a cell. In some cases the omic analysis is glycomic analysis, i.e. the assessment of glycomes, which are the sugars of a cell.

In some cases, the droplet contains a single cell, i.e. the biological material is a single cell. This droplet can be directed deposited onto a substrate, or it can be optionally incubated until the single cell divides into multiple isogenic cells, e.g. 5 or more, 50 or more, or 100 or more. In other cases, the droplet before incubation includes two or more cells. In some cases these cells are genetically identical. In some cases, the cells are isogenic. In some cases, the cells are non-identical genetically, wherein they can be referred to as being part of a consortia of cells. In some cases these genetically non-identical cells are part of a synthetic microbial consortia, which can also be referred to as a co-culture. In some cases, the incubation is not performed.

In some cases, the biological material is a lysed cell, or two or more lysed cells. In some cases, the biological material has been isolated from one or more cells, such as a nucleic acid or a protein. The biological material can contain a single nucleic acid, or multiple nucleic acids. In some cases the biological material includes a single protein, or multiple proteins. In some cases, the biological material is an organoid, which is a three-dimensional grouping of cells that is created in vitro and mimics the function and structure of an in vivo organ of a living organism. In other words, since biological processes inside a cell are sometimes influenced by nearby cells and the extracellular environment, and organoid creates a better model for studying biological functions than cells arranged in a two-dimensional structure across a surface, not to mention a single isolated cell. As such, in some cases an organoid is encapsulated in a droplet. In some cases the organoid includes 5 or more cells, such as 10 or more, 25 or more, 50 or more, 100 or more, or 250 or more. In some cases, the biological material is an organelle, which is a subunit of a cell. For example, an organelle can be isolated from a lysed cell and then encapsulated in the droplet, wherein exemplary organelles include ribosomes, cytoskeletons, flagellums, nucleolus, endoplasmic reticulum, Golgi apparatus, mitochondrion, nucleus, cilium, plasmid, and pilus.

In some cases, the method includes encapsulating a single cell in the droplet. In some cases, the method further includes incubating the droplet at a storage location after encapsulating and before the depositing until the single cell divides into 2 or more isogenic cells, such as 5 or more cells, 10 or more cells, 50 or more cells, 100 or more cells, or 1,000 or more cells. In other cases, the method includes encapsulating multiple genetically identical cells in the droplet. In some cases the incubation is not performed.

In some cases, the method further includes detecting the number of cells or the density of cells in the droplet before depositing. For instance, the droplets can be incubated for a time period and checked to see how many or what density of cells are in the droplet. If the droplets have sufficient cells, they can be deposited onto the substrate. Alternatively, if they have less than a desired number or density of cells, they can be placed, returned or discarded to the storage location so that they can incubate and increase in cell number. Since the mass spectroscopy can be used to detect a cellular metabolite, and since more cells will generate more metabolite than less cells, this detection can help ensure that enough metabolite will be produced for detection.

In some cases, the method further includes sorting the droplet before the depositing. The droplet can be sorted based on detection of the number or density of cells in the droplet. If the droplet has less than desired the number or density of cells, the droplet can be sorted to a storage location for incubation. The sorting can also sort an undesired droplet to a waste container. For example, if the droplet has zero cells, it can be sorted to a waste container. In some cases the incubation is not performed.

Any suitable type of cell can be used, such as a yeast cell, an animal cell, a bacterial cell, or a plant cell.

In some cases the droplet have a volume of 500 nl or less, such as 100 nl or less, 10 nl or less, 1 nl or less, 500 pl or less, 100 pl or less, 50 pl or less, 10 pl or less, 5 pl or less, or 1 pl or less. In some cases, the droplet has a volume greater than 500 nl, such as 750 nl or less or 1,000 nl or less.

An addressable location is a position on the substrate that is distinct from other addressable locations on the substrate.

Since droplets are positioned at addressable locations, the droplets can be individually analyzed by mass spectroscopy in a manner such that the presence of a nearby does not significantly interfere, or does not interfere at all, with the analysis of the droplet. For example, if droplets were directly adjacent to one another and touching one another, such placement might result in errors during mass spectroscopy, omic analysis, or both. The term addressable location is used interchangeably herein with the term discrete location.

In some cases the addressable location on the substrate comprises a well. The well can also be referred to as a region with a surface that is lower in elevation compared to a surface of an adjacent inter-well region. In some cases the well has a concave bottom surface, i.e. wherein the concavity of the bottom surface points upwards. In some cases the well has a circular cross section. In some cases the well has a width or diameter ranging from 20 μm to 500 μm. In some cases the well has a height ranging from 40 μm to 800 μm. In some cases the well has a rectangular or square cross-section. In some cases, the well has an irregular shape.

In some cases, the method can be used to aid in drug discovery or biological pathway engineering.

In some cases the droplet includes water during the depositing step. After being deposited at the addressable location on the substrate, the liquid, e.g. water, of the droplet can evaporate, leaving dried compounds. In some cases the mass spectroscopy is performed after the liquid of the droplet has evaporated.

A reagent can be added to the droplet with the one or more cells. The reagent can be added in any suitable manner, such as by selectively merging the cell-containing droplet with a reagent-containing droplet, e.g. in a microfluidic device. In some cases the reagent is capable of being metabolized by an enzyme of the cell. In some cases the mass spectroscopy involves detecting a metabolite generated by metabolism of the reagent by the enzyme. As such, the method can allow for the determination of how the genetics of the cell that relate to the enzyme influence the metabolism of the cell. In some cases, the reagent is a cellular growth reagent, e.g. food, vitamins, and nutrients. In some cases, the reagent is an inducing reagent for activating biological processes. In some cases, the reagent is an inhibitor for inhibiting biological processes.

Various mass spectroscopy techniques can be employed, such as Matrix-Assisted Laser Desorption/Ionization (MALDI) spectroscopy, Desorption Electrospray Ionization (DESI) spectroscopy, Nanostructure-Initiator (NIMS) spectroscopy, or Electrospray Ionization (ESI) spectroscopy. In some cases the mass spectroscopy involves MALDI spectroscopy.

Various microfluidic structures and techniques can be employed to perform the encapsulation step. In some cases the encapsulation involves a cross-junction droplet encapsulation device or a plug-squeeze mechanism.

The method can further include encapsulating a second biological material in a second droplet having a volume of 1 nl or less, depositing the second droplet to a second addressable location of the substrate, and performing mass spectroscopy on the same droplet. As used herein, the original "droplet" is also referred to as the "first droplet". Thus, the first and second droplets are deposited onto the same substrate.

In some cases during the encapsulating the first droplet traveled through a microfluidic channel and the second droplet also traveled through the same microfluidic channel. In some cases the time between the first encapsulation of the first droplet and the second encapsulation of the second droplet is 1 second or less, such as 0.1 second or less, 0.01 second or less, 0.001 second or less, or 0.0001 second or less. In other words, when performing encapsulations with a microfluidic device, encapsulations can be performed at a rate of 1 Hz or more, 10 Hz or more, 100 Hz or more, 1,000 Hz or more, or 10,000 Hz or more.

In some cases during the depositing the first droplet traveled through a microfluidic channel and the second droplet traveled through the same microfluidic channel. The time between the depositing of the first droplet and the depositing of the second droplet can be 5 seconds or less, such as 1 second or less, or 0.1 second or less.

The depositing of droplets can either be selective or unselective. In cases of selective depositing, a particular droplet is deposited to a particular addressable location, and the knowledge of which droplet is at which location is retained, e.g. by a human or by a computer. For example, a first droplet known to contain a single cell with genetic profile A can be deposited at location 1, and a second droplet known to contain a single cell with genetic profile B can be deposited at location 2. As such, since mass spectroscopy is performed in a manner such that the mass spectrometer knows which addressable location is being analyzed, mass spectroscopy results can be correlated with genetic profiles based on the location of each droplet. Hence, in some cases the method includes performing omic analysis before the depositing. In unselective depositing, droplets are deposited onto the substrate in a manner that does not control which droplet resides at which addressable location. As an example of unselective depositing, droplets with single cells can be deposited to onto the substrate, and inertia or gravity can result in the droplets moving into different addressable locations, such as wells. Mass spectroscopy can determine a property of each droplet, and omic analysis afterwards can determine an omic property of the droplets. These mass spectroscopy results and omic analysis can then be compared with one another, even though the droplets were not placed in a controlled manner, nor were they deposited to specific addressable locations.

In some cases the outlet of the microfluidic device physically moves between addressable locations of the substrate, whereas in other cases the substrate moves to align the addressable locations with the outlet of the microfluidic device. This physical motion can be used to selectively deposit droplets to particular addressable locations.

As an example, a researcher might want to find a genetic profile that would produce a large amount of metabolite. The researcher could encapsulate the first and second droplets with first and second cells that are genetically different, deposit the first and second droplets onto first and second addressable locations, and perform mass spectroscopy on the first and second droplets. If the second droplet showed high amounts of metabolite produced by mass spectroscopy, then the second droplet could be analyzed genetically in order to determine which genetic variations lead to the high levels of metabolism. In other words, to find what variation of an enzyme was highly effective at metabolizing a reagent into a metabolite. In addition, if the first droplet showed little to no metabolite produced, then the researcher could skip performing genetic analysis on the first droplet because the genetic profile of the first cell would not be useful to the researcher.

The method can also include selectively conducting genomic analysis on either the first droplet or the second droplet based on the mass spectroscopy. Stated in another manner, if the method involves selectively conducting genetic analysis based on the mass spectroscopy results, then genetic analysis is purposefully not performed on at least one of the droplets but genetic analysis is performed on at least one of the droplets based on the mass spectroscopy results. In addition, since the droplets are retained at addressable locations, the mass spectroscopy results for a particular droplet can be compared to the genomic analysis results for the particular droplet.

In some cases, the genetic analysis is performed by individually genetically analyzing each of the desired droplets. In other cases, each of the desired droplets are barcoded, e.g. using barcode beads, and the droplets are pooled before being genetically analyzed.

In some cases the first cell and the second cell differ at a genetic region that corresponds to an enzyme. The method can include adding a reagent to the first droplet and the second droplet after the encapsulating steps but before the depositing steps, wherein at least one variation of the enzyme is capable of metabolizing the reagent.

The method can further include generating the first cell and second cell as part of a mutant library before the encapsulation steps.

The method can optionally include generating a report comparing a mass spectroscopy result and an omic analysis result. For example, the report could describe at least a part of the genetic sequence corresponding to an enzyme (an example of a genomic analysis), and the report could also describe the amount of an enzyme substrate that was metabolized by the enzyme, which can be determined by mass spectroscopy. The mass spectroscopy can either determine the amount of metabolism either by assessing the quantity of metabolite generate, or by assessing the amount of enzyme substrate that remained. For example, if 100 ng of an enzyme substrate had been added to the droplet, and the mass spectrometer determined that only 40 ng remained, then it could be inferred that 60 ng was metabolized by the enzyme. Alternatively, the mass spectrometry could directly measure the metabolite at approximately 60 ng.

In some cases, generating the report involves results from 2 or more droplets, such as 5 or more, 10 or more, 50 or more, 100 or more, 500 or more, 1,000 or more, or 5,000 or more. For instance, the report can compare a mass spectroscopy result and an omic analysis result from a first droplet with a mass spectroscopy and omic analysis result from a second droplet. In some cases, the report can indicate that a certain omic result is associated with increased metabolism of the enzyme substrate by the enzyme compared with a different omic result. For instance, given the example discussed above, the report could state that the first cell produced little to no metabolite, whereas the second cell produced a large amount of metabolite, and the report also describes the results of the omic analysis of the first and second cells. In some cases, this comparison is performed on 5 or more droplets, such as 50 or more. In some cases, this comparison involves comparing the omic result, e.g. the genome or transcriptome or proteome corresponding to the enzyme, to the amount of metabolite generated.

Typically, although not necessarily, the method for two cells occurs in the following order: the optional step of generating the mutant library, encapsulating the first cell, encapsulating the second cell, optionally incubating the first and second droplets until each cell divides into 5 or more cells, depositing the first droplet and second droplet, analyzing the first and second droplet by mass spectroscopy, performing genetic analysis on one or both of the droplets optionally selectively based on the mass spectroscopy results, and optionally creating a report describing a correlation between the mass spectroscopy and genomic analysis.

The method can also be extended to 3 or more droplets, such as 10 droplets, 20 droplets, 50 droplets, 100 droplets, 500 droplets, 1,000 droplets, 10,000 droplets, or 100,000 droplets.

When the method is described for a certain number of droplets, it is to be understood that the method also typically involves an equal number of addressable locations. For instance, if 75 droplets are encapsulated, then 75 droplets are deposited to 75 addressable locations. However, since some droplets might have zero cells or multiple cells after encapsulation, then these droplets might not be desired, and so they are in some cases sorted to a waste container. In such cases, 75 droplets might be encapsulated, but if 40 of the droplets have zero cells, then those 40 droplets can be sorted to a waste container and the remaining 35 droplets can be deposited to 35 addressable locations of the substrate.

Although in some cases the method intends to encapsulate a single cell in a single droplet, droplets can also be produced that have zero cells or two or more cells. In some cases the microfluidic device is configured such that 50% or more of the cells from a library are encapsulated as single cells, such as 75% or more or 90% or more.

In some cases, the method includes generating 20 droplets having a volume of 1 nl or less, whereas at least one droplet has a single cell encapsulated therein and at least one droplet has zero cells, detecting the number of cells in each of the 20 droplets, sorting the 20 droplets such that droplets with a single cell are deposited to an addressable location on the substrate and other droplets are recycled or directed to a waste container.

In some cases, the method includes encapsulating 500 cells in 500 droplets each having a volume of 1 nl or less, depositing the 500 droplets to 500 addressable locations of the substrate, and performing mass spectroscopy on the 500 droplets. Such a method can also include selectively conducting genomic analysis on 1 to 4999 of the droplets based on the mass spectroscopy.

In some cases, the method includes encapsulating 50,000 cells in 50,000 droplets each having a volume of 1 nl or less, depositing the 50,000 droplets to 50,000 addressable locations of the substrate, and performing mass spectroscopy on the 50,000 droplets. Such a method can also include selectively conducting genomic analysis on 1 to 49,999 of the droplets based on the mass spectroscopy.

In some cases the density of the addressable locations on the substrate is 10 per $cm^2$ or more, such as 100 per $cm^2$ or more, 1,000 per $cm^2$ or more, or 10,000 per $cm^2$ or more. The substrate can sometimes have a surface area of 150 $cm^2$ or less, such as 80 $cm^2$ or less, 40 $cm^2$ or less, or 20 $cm^2$ or less. The substrate can include any suitable material, such as glass. In some cases, the substrate includes metal.

In some cases, the method involves encapsulating two or more cells in a single droplet and studying a cell-cell interaction between each of the two or more cells. In some cases, studying the cell-cell interaction involves mass spectroscopy. In some cases, each of the two or more cells are of the same type, e.g. there are five cells and all five cells are liver cells. In other cases, the two or more cells include different cell types. For example, there can be one or more immune cells, e.g. T cells, and one or more cancer cells. In such a case, studying the cell-cell interaction can involve studying the efficacy of an immune cell at killing a cancer cell.

Cluster Analysis

In some cases, the method further comprises conducting cluster analysis on the mass spectroscopy data, thereby identifying two or more clusters. As used herein, "cluster analysis" and "clustering" refer to categorizing samples into groups (i.e. clusters) so that each sample in a cluster is more similar to the other samples in that cluster than it is to samples in another cluster. In the present methods, the different "samples" refers to different droplets that contain different enzymes. The clustering can be performed using a machine learning algorithm. In some cases the droplet have a volume of 500 nl or less, such as 100 nl or less, 10 nl or less, 1 nl or less, 500 pl or less, 100 pl or less, 50 pl or less, 10 pl or less, 5 pl or less, or 1 pl or less. In some cases, the droplet has a volume greater than 500 nl, such as 750 nl or less or 1,000 nl or less. As such, cluster analysis results in the categorization of enzymes into clusters so that each enzyme in a cluster is more similar to other enzymes in that cluster than to enzymes in a different cluster. The clustering analysis can be performed by a computer processor.

Exemplary types of cluster analysis include connectivity models (e.g. hierarchical clustering), centroid models (e.g. k-means algorithms), distribution models (e.g. multivariate normal distributions), density models (e.g. DBSCAN and OPTICS), subspace models (e.g. biclustering), HCS clustering, signed graph models, and neural models. The clustering can include principal component analysis (PCA) or independent component analysis (ICA).

In some cases, the clustering is performed with two-dimensional data. For instance, the intensity of the mass spectrum at two different mass-to-charge (m/z) ratio values can be assessed, and the enzymes can be clustered based on this two-dimensional data. Stated in another manner, the clustering is based on 2 mass-to-charge (m/z) ratio values. For example, with two dimensions, the data can be plotted on a two-dimensional graph and clusters can be directly visualized. In other cases, clustering is performed based on 3 or more m/z ratio values, such as 5 or more, 10 or more, 15 or more, 20 or more, 30 or more, 50 or more, or 100 or more. In some of such cases, the number of m/z ratio values is less than 150, such as less than 75, less than 45, or less than 25. The number of samples that are subjected to cluster analysis can be 10 or more, such as 50 or more, 100 or more, 500 or more, 2,000 or more, or 10,000 or more. In some of such cases, the number of samples is less than 15,000, such as less than 3,000, less than 700, or less than 400. For example, 100 or more enzymes can be clustered based on 5 or more m/z ratio values. As another example, 500 or more enzymes can be clustered based on 10 or more m/z ratio values. Such clustering can be performed by a computer processor, e.g. using a machine learning algorithm.

In some cases, the clustering results in each sample being assigned to a single cluster (i.e. hard clustering or strict partitioning clustering). In other cases, each sample belongs to one or more clusters to a certain degree or with a certain probability (i.e. soft clustering, fuzzy clustering, overlapping clustering). The clustering can result in samples that are not assigned to a particular cluster, e.g. erroneous samples or statistical outliers, which can also be considering as being assigned to an outlier or erroneous cluster. The erroneous samples or statistical outliers can be considerably different from one another. The clustering can also include hierarchical clustering, wherein samples are assigned to two or more clusters (i.e. "parent clusters"), which each contain two or more clusters within them (i.e. "child cluster" or "subcluster"). In addition, the clustering can be modified by modifying the clustering threshold or by adjusting the number of desired clusters.

The cluster analysis can comprise dimensionality reduction, such as nonlinear dimensionality (e.g. uniform manifold approximation and projection (UMAP)). As used herein, "dimensionality reduction" refers to creating a lower-dimensional representation that approximates higher-dimensional data. For instance, as described above the clustering can be performed based on based on 10 or more m/z ratio values, such as 12 m/z ratios. Dimensionality reduction can transform this 12-dimensional data into a lower-dimensional representation, such as a 3-dimensional representation that can be visualized through 3-dimensional computer software or a 2-dimensional representation that can be visualized as a planar image on a computer monitor or piece of paper. After undergoing dimensionality reduction, in some cases the clusters are more easily visualized, represented, or identified.

Clustering the mass spectroscopy data of multiple enzymes can provide a manner of identifying clusters that correspond to changes in the activity of the enzymes. Enzymes catalyze the conversion of enzyme substrates into metabolites. For instance, a reference cluster might correspond to the generation of a first metabolite by a reference enzyme and by mutant enzymes that also produce the first metabolite. In addition, a second cluster might correspond to the generation of a different (i.e. second) metabolite by different mutant enzymes.

As used herein, "mutant enzyme" and "enzyme variant" refer to an enzyme of the same type as the reference enzyme, but which is not identical to the reference enzyme. For instance, the mutant enzyme and reference enzyme can both be encoded by the same gene, e.g. due to one or more mutations in the gene, such as between 1 and 20 mutations or 1 to 5 mutations. The mutant enzyme and reference enzyme might differ due to alternative RNA splicing, e.g. of the same allele. The term "reference enzyme" merely identifies the enzyme being used as a point of comparison, and the term reference enzyme is used interchangeably with "first enzyme".

In addition to differences in the identity of the metabolite generated by the enzymes, the clusters can also correspond to differences in which substrates the enzymes use to make the metabolite. For instance, a reference cluster might represent enzymes converting a first substrate to the metabolite, whereas the second cluster might represent enzymes converting a second substrate to the metabolite. The clusters can also represent differences in the speed at which the enzymes catalyze conversion of a substrate to a metabolite.

Thus, the clustering analysis can provide a manner of identifying whether some of the mutant enzymes have different enzymatic activity than the reference enzyme. Such differences in activity include the production of a different metabolite, the use of a difference enzyme substrate, differences in the speed of converting the enzyme substrate to the metabolite, or a combination thereof. In some cases multiple reference enzymes are employed, e.g. including different groups of mutant enzymes derived from each of the reference enzymes.

In some cases, the method involves encapsulating ten or more enzymes in separate droplets; depositing the ten or more droplets to separate addressable locations of one or more substrates; performing mass spectroscopy on the ten or more droplets, thereby generating mass spectroscopy data; and conducting cluster analysis on the mass spectroscopy data, thereby identifying two or more clusters. For instance, one or more of the ten enzymes can be a reference enzyme, such as two or more, three or more, or four or more. In addition, encapsulating ten or more enzymes in separate droplets means that each enzyme is located in a droplet and no droplet contains more than one enzyme. The depositing step means that the ten or more droplets are deposited onto ten or more separate addressable locations, wherein each addressable location contains no more than one droplet.

In some cases, the cluster analysis is based on m/z values that are selected based on signal-to-noise ratios, inter-sample variance, or a combination thereof. The signal-to-noise ratio refers to the intensity of the mass spectrum peaks relative to the noise, baseline, or presence of overlapping neighboring peaks in the mass spectrum. By inter-sample variance it is meant that some m/z values have significantly different values between samples whereas other m/z values have relatively similar values between most or all samples. The m/z values that are significantly different might correspond to the peaks of metabolites, substrates, or other components that are at significantly different concentrations due to the different activities of the enzyme variants.

In some cases, the m/z values or peaks used for cluster analysis correspond to enzyme substrates or metabolites. In other cases, the m/z values instead correspond to other compounds in the sample (e.g. other compounds in a cell expressing the enzyme) that are perturbed due to enzyme activity. In particular, production of a new metabolite will alter the overall metabolism of the cell (e.g. alter the central metabolism of the cell), which will have secondary effects on the levels of other compounds which can be detected by mass spectroscopy. Thus, even if the identities of these other compounds is not determined, and even if peaks in the mass spectra are not assigned to particular compounds, the cluster analysis can show that the overall metabolism of the cell has significantly changed, suggesting a change in enzyme activity, e.g. significant production of a new metabolite.

The method can also include further biochemical analysis based on the clustering analysis. For example, if the clustering analysis indicates a new cluster appearing to have different enzyme activity than the reference cluster, samples of the new cluster can be investigated. For instance, omic analysis can be performed on 1 or more samples from the new cluster, e.g. 5 to 1000 samples, 10 to 500 samples, or 20 to 100 samples. Omic analysis can also be performed on samples from the reference cluster, or previously recorded omic analysis of the reference cluster or reference enzyme can be obtained. The omic analysis results between the reference cluster and new (mutant) cluster can be compared, thereby identifying a possible biochemical mechanism causing the differences that resulted in the new cluster. This comparison of omic results can be performed by a computer processor, e.g. by a DNA or RNA sequence comparison software program or by a statistical analysis software program. Exemplary causes include a different enzyme structure due to mutations in DNA encoding the enzyme, alternative RNA splicing, or a combination thereof. In other words, the method can include using the omic analysis to identify one or more DNA mutations, alternative RNA splicing differences, or a combination thereof that resulted in the reference enzyme and mutant enzyme being located in different clusters.

The method can also include evaluating whether or not the mutant enzyme produces a compound that the reference enzyme does not produce based on the mass spectroscopy data. Stated in another manner, the method can include determining whether the mutant enzymes of the new cluster produce a different metabolite than the reference cluster, or a new metabolite in addition to the metabolite of the reference cluster. For instance, the mass spectroscopy data from mutant samples can be analyzed, such as by comparing the mass spectrum to a database of known or predicted mass spectrum. Such analysis can be performed by a computer processor.

Replicate Plating

In some cases, the droplet is deposited to an addressable location of a substrate, and the mass spectroscopy is performed while the material is still at the addressable location on the substrate. For instance, cells can be grown at the addressable location, and the mass spectroscopy can be performed at that location.

However, in some cases, although not all cases, the mass spectroscopy can make it difficult to successfully recover the cells in a living state, or to successfully recover or analyze the omic material, such as genetic material. As such, in some cases the droplet is contacted with a second substrate such that a portion of the droplet is transferred to a second addressable location on the second substrate, while another portion of the droplet remains at the addressable location of the first substrate. In some cases, at least some of the cells of the droplet are transferred to the second substrate. The second substrate is also referred to herein as the "replicate substrate" or "replicate plate". The transfer of such material is also referred to herein as "stamping". In some cases, the second substrate lowered onto the droplet or droplets, raised, and then rotated by 180 degrees, e.g. so that the droplets sit on the plate. In some cases the droplet material is transferred to the second substrate by hydrostatic forces.

Afterwards, mass spectroscopy can be performed at one of the addressable locations (e.g. the first addressable location on the first substrate), thereby allowing for analysis of the droplet. In addition, since the other location (e.g. the second addressable location on the second substrate) did not undergo mass spectroscopy, further steps can be performed at the other location without possible negative effects from the mass spectroscopy. For instance, any cells at the other location can be incubated in order to grow the cell colony or increase the number of cells for further analysis. As another example, any omic material at the other location can be subjected to omic analysis, such as genomic analysis. In some cases, by preserving the living cells on the second substrate, if the cells were found to have advantageous technical properties during the mass spectroscopy, then the living cells on the second substrate can be directly used for further analyses or possibly grown for commercial use. In contrast, if all living cells were lost during the method, e.g. due to the mass spectroscopy, then further analysis or use of the cells would involve the step of manually re-creating the cells, e.g. by genetically engineering existing cells to match the genetic profile of the lost cells, which would involve additional time and effort. FIG. 29 shows an exemplary method employing the transfer of droplet material to the replicate plate.

In some cases the second substrate has a surface comprising a hydrocolloid (e.g. pectic and gelatin) or a hydrogel (e.g. agar). Such surfaces can aid in the growth of cells transferred to the second substrate. Such surfaces can also have adhesive properties that aid in the transfer of droplet material from the first substrate to the second substrate.

Systems

Provided are systems that include a substrate with addressable locations, a microfluidic device configured to encapsulate a cell in a droplet having a volume of 1 nl or less and deposit the droplet to one of the addressable locations, a mass spectrometer, and a genomic analysis device.

In some cases the system further includes a storage location that is configured to store the droplet for 1 hour or more after the encapsulating but before the depositing. The storage location can be part of the microfluidic device or separate from the microfluidic device. However, the storage location is operably connected to the microfluidic device such that each droplet can be moved from the encapsulation location to the storage location, and then to element that deposits the droplet to the addressable location. In some cases the system further includes a detector that is configured to detect the number of cells or density of cells in the droplet and a sorter configured to sort the droplet based on the detection. For example, the sorter can sort the droplet to the storage location if it has too few cells such that the cells will be incubated in the storage location and multiply.

The microfluidic device can be configured to produce droplets of any suitable size or volume, such as droplets with a volume of 1 nl or less, such as 500 pl or less, 100 pl or less, 50 pl or less, 10 pl or less, 5 pl or less, or 1 pl or less.

In some cases the addressable location includes a well. In some cases the well has a concave bottom surface. In some cases the substrate includes glass. In some cases, the substrate includes glass coated with a layer of indium tin oxide (ITO).

In some cases the microfluidic device is configured to add a reagent to a droplet after the encapsulation but before the deposition. For example, the microfluidic device can be configured to merge a first droplet containing the cell with a second droplet containing the reagent.

In some cases the mass spectrometer is a Matrix-Assisted Laser Desorption/Ionization (MALDI) spectrometer, Desorption Electrospray Ionization (DESI) spectrometer, or Electrospray Ionization (ESI) spectrometer. In some cases the microfluidic device is configured to perform the encapsulation using a cross-junction, a plug-squeeze mechanism.

The system can also include a pump configured to aspirate the droplet at the addressable location and move it to a genomic analysis device. In some cases, the liquid of the droplet has evaporated by the time that the pump is to move the droplet to the genomic analysis device. As such, the pump can be configured to deposit a liquid, e.g. water, to the addressable location and thereby create a mixture of the remaining material of the droplet and the water. The pump can then aspirate this mixture and move it to the omic analysis device. In some cases the genomic analysis device is a polymerase chain reaction (PCR) tube. In some cases the genomic analysis device is configured to conduct DNA sequencing, mRNA analysis, or both.

The microfluidic device can be configured to perform the encapsulation at a rate of 1 Hz or more, such as 10 Hz or more, 100 Hz or more, or 1,000 Hz or more, or 10,000 Hz or more. The microfluidic device can be configured to perform depositions at a rate of 0.1 Hz or more, such as 0.2 Hz or more, 1 Hz or more, 10 Hz or more, or 100 Hz or more.

The substrate can include numerous addressable locations, e.g. wherein each addressable location includes a well. The substrate can have 100 or more addressable locations, such as 500 or more, 5,000 or more, 10,000 or more, 50,000 or more, or 100,000 or more. In some cases the density of the addressable locations on the substrate is 100 per $cm^2$ or more, such as 1,000 per $cm^2$ or more, 10,000 per $cm^2$ or more, or 100,000 per $cm^2$ or more. In some cases the substrate has a surface area of 150 $cm^2$ or less, such as 80 $cm^2$ or less, 40 $cm^2$ or less, or 20 $cm^2$ or less. For example, the substrate can have 5,000 or more addressable locations that each include a well with a density of 100 or more addressable locations per $cm^2$ and a substrate with a surface area of 80 $cm^2$ or less.

In some cases, the microfluidic device, substrate, and mass spectrometer are positioned relative to one another and optionally operatively coupled to one another such that the droplets can be deposited onto the substrate, and the mass spectroscopy can be performed, without having to move the substrate, e.g. movement by a human. In other cases, the substrate is moved by a robot or human between the depositing step and the mass spectroscopy step. Similarly, the relative positions and operative coupling of the substrate, microfluidic device, and omic analysis device can be such that the substrate does not need to be moved between the depositing and the omic analysis. In other cases, the substrate is moved between such steps.

The system can also include an output device that reports a correlation between the mass spectroscopy and the genomic analysis. The output device can include a computer.

Notwithstanding the appended claims, the disclosure is also defined by the following clauses:

1. A method, comprising:
   encapsulating a biological material in a droplet having a volume of 500 nl or less;
   depositing the droplet to an addressable location of a substrate; and
   performing mass spectroscopy on the droplet.

2. The method of clause 1, further comprising sorting the droplet before the depositing.

3. The method of clause 2, wherein the sorting is based on a number of cells or density of cells detected in the droplet.

4. The method of any of clauses 1-3, wherein the biological material is a single cell, further comprising incubating the droplet at a storage location after the encapsulating until the single cell divides into 5 or more isogenic cell, and then conducting the depositing.

5. The method of any of clauses 1-4, further comprising incubating the biological material after the depositing and before performing of mass spectroscopy.

6. The method of any of clauses 1-5, further comprising conducting image analysis, fluorescent labeling, or a combination thereof on the droplet after performing mass spectroscopy.

7. The method of any of clauses 1-6, further comprising conducting omic analysis on the droplet after performing mass spectroscopy.

8. The method of clause 7, wherein the omic analysis comprises genomic analysis.

9. The method of clause 8, wherein the genomic analysis comprises aspirating material at an addressable location and moving it to a genomic analysis device.

10. The method of clause 9, wherein the genomic analysis comprising depositing water at an addressable location, and then aspirating a mixture of the water and material that was already present at the addressable location and moving a mixture of the water and the material to a genomic analysis device.

11. The method of any of clauses 8-10, wherein the genomic analysis comprises polymerase chain reaction (PCR).

12. The method of any of clauses 8-11, wherein the genomic analysis comprises sequencing DNA, analyzing mRNA, or a combination thereof.

13. The method of any of clauses 8-12, wherein the genomic analysis comprises genome-wide profiling of open chromatin region, DNA methylation sequencing, or a combination thereof.

14. The method of clause 7, wherein the omic analysis comprises proteomic analysis.

15. The method of clause 7, wherein the omic analysis comprises transcriptome analysis.

16. The method of clause 7, wherein the omic analysis comprises metabolomic analysis.

17. The method of clause 7, wherein the omic analysis comprises glycomic analysis.

18. The method of any of clauses 7-17, further comprising generating a report comparing a mass spectroscopy result and an omic analysis result.

19. The method of any of clauses 1-18, wherein the biological material is a single cell.

20. The method of any of clauses 1-18, wherein the biological material is two or more cells.

21. The method of clause 20, wherein the two or more cells are genetically identical.

22. The method of clause 20, wherein the two or more cells are not genetically identical.

23. The method of any of clauses 1-18, wherein the biological material is contents of a lysed cell.

24. The method of any of clauses 1-18, wherein the biological material is an organoid.

25. The method of any of clauses 1-18, wherein the biological material is cell free extract.

26. The method of any of clauses 1-25, wherein the droplet has a volume of 100 nl or less.

27. The method of clause 26, wherein the droplet has a volume of 10 nl or less.

28. The method of clause 27, wherein the droplet has a volume of 1 nl or less.

29. The method of clause 28, wherein the droplet has a volume of 0.1 nl or less.

30. The method of any of clauses 1-29, wherein the addressable location comprises a well.

31. The method of clause 30, wherein the well comprises a concave bottom surface.

32. The method of any of clauses 30-31, wherein the well has a width or diameter ranging from 20 μm to 500 μm and a height ranging from 40 μm to 800 μm.

33. The method of any of clauses 1-32, wherein the droplet comprises water during the depositing step and the mass spectroscopy is performed after the water of the droplet has evaporated.

34. The method of any of clauses 1-33, further comprising adding a reagent to droplet after the encapsulating but before the depositing.

35. The method of clause 34, wherein the reagent is an enzyme substrate that is capable of being metabolized by an enzyme in the droplet.

36. The method of any of clauses 1-35, wherein the mass spectroscopy comprises detecting a metabolite generated by the metabolism of the enzyme substrate by the enzyme.

37. The method of any of clauses 1-36, wherein the mass spectroscopy is Matrix-Assisted Laser Desorption/Ionization (MALDI) spectroscopy, Desorption Electrospray Ionization (DESI) spectroscopy, Nanostructure-Initiator (NIMS) spectroscopy, or Electrospray Ionization (ESI) spectroscopy.

38. The method of any of clauses 1-37, wherein the encapsulation involves a cross-junction droplet encapsulation device, a plug-squeeze mechanism, centrifugation, shaking emulsion, or a combination thereof.

39. The method of any of clauses 1-38, wherein further comprises encapsulating a second biological material in a second droplet having a volume of 500 nl or less, depositing the second droplet to a second addressable location of the substrate, and performing mass spectroscopy on the second droplet.

40. The method of clause 39, further comprising conducting omics analysis on the second droplet after performing mass spectroscopy on the second droplet.

41. The method of clause 40, further comprising generating a report comparing a mass spectroscopy result and an omic analysis result of the droplet with a mass spectroscopy result and an omic analysis result of the second droplet.

42. The method of clause 41, wherein the report indicates that a certain omics result is associated with increased metabolism of an enzyme substrate compared to a different omics result.

43. The method of any of clauses 39-42, wherein during the encapsulating the first droplet traveled through a microfluidic channel and the second droplet also traveled through the microfluidic channel.

44. The method of any of clauses 39-43, wherein the time between the first encapsulating and the second encapsulating is 0.1 second or less.

45. The method of clause 44, wherein the 0.1 seconds or less is 0.001 second or less.

46. The method of any of clauses 1-45, wherein during the depositing the first droplet traveled through a microfluidic channel and the second droplet also traveled through the microfluidic channel.

47. The method of any of clauses 1-46, wherein the time between the first depositing and the second depositing is 5 seconds or less.

48. The method of clause 47, wherein the 5 seconds or less is 1 second or less.

49. The method of any of clauses 39-48, further comprising selectively conducting omics analysis on either the droplet or the second droplet based on the mass spectroscopy.

50. The method of any of clauses 39-49, further comprising barcoding the addressable location of the droplet and the second droplet, further comprising conducting genomic on both the droplet and the second droplet.

51. The method of clause 50, wherein the addressable locations are barcoded with barcode beads.

52. The method of any of clauses 39-51, wherein the biological material is a cell and the second biological material is a second cell.

53. The method of clause 52, further comprising generating the cell and second cell as part of a mutant library.

54. The method of any of clauses 39-53, wherein the cell and the second cell differ at a genetic region that corresponds to an enzyme.

55. The method of any of clauses 39-54, further comprising adding an enzyme substrate to the droplet and the second droplet, wherein at least one variation of the enzyme is capable of metabolizing the enzyme substrate.

56. The method of any of clauses 1-55, comprising:
   generating 20 droplets having a volume of 500 nl or less, wherein at least one droplet has a single cell encapsulated therein and at least one droplet has zero cells;
   detecting the number of cells in each of the 20 droplets; and
   sorting the 20 droplets such that each droplet with a single cell is deposited to a different addressable location on the substrate and other droplets are recycled or directed to a waste container.

57. The method of clause 56, comprising encapsulating 500 cells in 500 droplets each having a volume of 500 nl or less, depositing the 500 droplets to 500 addressable locations of the substrate, and performing mass spectroscopy on the 500 droplets.

58. The method of clause 57, comprising selectively conducting genomic analysis on 1 to 499 of the droplets based on the mass spectroscopy.

59. The method of any of clauses 57-58, comprising barcoding the 10,000 addressable locations of the 10,000 droplets, further comprising conducting genomic analysis on the 10,000 droplets.

60. The method of any of clauses 57-59, comprising encapsulating 10,000 cells in 10,000 droplets each having a volume of 1 nl or less, depositing the 10,000 droplets to 10,000 addressable locations of the substrate, and performing mass spectroscopy on the 10,000 droplets.

61. The method of any of clauses 57-60, comprising selectively conducting omic analysis on 1 to 9,999 of the droplets based on the mass spectroscopy.

62. The method of any of clauses 57-61, comprising barcoding the 10,000 addressable locations of the 10,000 droplets, further comprising conducting omic analysis on the 10,000 droplets.

63. The method of any of clauses 57-62, wherein the density of the addressable locations on the substrate is 100 per $cm^2$ or more.

64. The method of any of clauses 57-63, wherein the density of the addressable locations on the substrate is 10,000 per $cm^2$ or more.

65. The method of any of clauses 57-64, wherein the substrate has a surface area of 80 $cm^2$ or less.

66. A system, comprising:
   a substrate comprising addressable locations;
   a microfluidic device configured to encapsulate a biological material in a droplet having a volume of 500 nl or less and deposit the droplet to one of the addressable locations;
   a mass spectrometer; and
   an omic analysis device.

67. The system of clause 66, wherein the microfluidic device further comprises a storage location that is configured to store the droplet for 1 hour or more after the encapsulating but before the depositing.

68. The system of any one of clauses 66-67, wherein the microfluidic device further comprises a detector that is configured to detect the number of cells or density of cells in the droplet and a sorter configured to sort the droplet based on the detection.

69. The system of any one of clauses 66-68, wherein the droplet has a volume of 10 nl or less.

70. The system of any one of clauses 66-69, wherein the addressable location comprises a well.

71. The system of clause 70, wherein the well comprises a concave bottom surface.

72. The system of any one of clauses 66-71, wherein the microfluidic device is configured to add a reagent to the droplet after the encapsulation but before the deposition.

73. The system of any one of clauses 66-72, wherein the mass spectrometer is a Matrix-Assisted Laser Desorption/Ionization (MALDI) spectrometer, Desorption Electrospray Ionization (DESI) spectrometer, or Electrospray Ionization (ESI) spectrometer.

74. The system of any one of clauses 66-73, wherein the omic analysis device is a genomic analysis device.

75. The system of any one of clauses 66-73, wherein the omic analysis device is a proteomic analysis device.

76. The system of any one of clauses 66-73, wherein the omic analysis device is a metabolomic analysis device.

77. The system of any one of clauses 66-73, wherein the omic analysis device is a glycomic analysis device.

78. The system of any one of clauses 66-77, wherein the microfluidic device is configured to perform the encapsulation using a cross-junction, a plug-squeeze mechanism, centrifugation, shaking emulsion, or a combination thereof.

79. The system of any one of clauses 66-78, further comprising a pump configured to aspirate the droplet at the addressable location and move it to the genomic analysis device.

80. The system of clause 79, wherein the pump is configured to selectively aspirate only certain droplets at certain addressable locations based on mass spectroscopy results from the mass spectrometer.

81. The system of clause 74, wherein the genomic analysis device is configured to conduct DNA sequencing, mRNA analysis, or both.

82. The system of any one of clauses 66-81, wherein the microfluidic device is configured to perform encapsulations at a rate of 100 Hz or more.

83. The system of clause 82, wherein the 100 Hz or more is 10,000 Hz or more.

84. The system of any one of clauses 66-83, wherein the microfluidic device is configured to perform depositions at a rate of 0.1 Hz or more.

85. The system of clause 84, wherein the 0.1 Hz or more is 1 Hz or more.

86. The system of any one of clauses 66-85, wherein the substrate comprises 500 or more addressable locations.

87. The system of clause 86, wherein the 500 or more is 5,000 or more.

88. The system of any one of clauses 66-87, wherein the density of the addressable locations on the substrate is 100 per $cm^2$ or more.

89. The system of clause 88, wherein the 100 per $cm^2$ or more is 10,000 per $cm^2$ or more.

90. The system of any one of clauses 66-89, wherein the substrate has a surface area of 80 $cm^2$ or less.

91. The system of any one of clauses 66-90, further comprising an output reporting device configured to generating a report comparing a mass spectroscopy result and an omic analysis result of a first droplet with a mass spectroscopy result and an omic analysis result of a second droplet.

92. The system of clause 91, wherein the report indicates that a certain omics result is associated with increased metabolism of an enzyme substrate compared to a different omics result.

93. A method, comprising:
   encapsulating ten or more enzymes in separate droplets;
   depositing the ten or more droplets to separate addressable locations of one or more substrates;
   performing mass spectroscopy on the ten or more droplets, thereby generating mass spectroscopy data;
   conducting cluster analysis on the mass spectroscopy data, thereby identifying two or more clusters.

94. The method of clause 93, wherein the cluster analysis is based on 3 or more mass-to-charge (m/z) ratio values.

95. The method of clause 94, wherein the cluster analysis is based on 15 or more mass-to-charge (m/z) ratio values.

96. The method of any one of clauses 93-95, wherein the mass-to-charge (m/z) values are selected based on signal-to-noise ratios, inter-sample variance, or a combination thereof.

97. The method of any one of clauses 93-96, wherein a first cluster comprises a reference enzyme and a second cluster comprises a mutant enzyme.

98. The method of clause 97, further comprising omic analysis of the mutant enzyme, the reference enzyme, or a combination thereof.

99. The method of clause 98, further comprising using the omic analysis to identify one or more DNA mutations, alternative RNA splicing differences, or a combination thereof that resulted in the reference enzyme and mutant enzyme being located in different clusters.

100. The method of any one of clauses 97-99, further comprising evaluating whether or not the mutant enzyme produces a compound that the reference enzyme does not produce based on the mass spectroscopy data.

101. The method of clause 100, further comprising identifying the compound based on the mass spectroscopy data.

102. The method of any one of clauses 93-101, wherein the ten or more enzymes are two hundred or more enzymes.

103. The method of clause 102, wherein the two hundred or more enzymes are one thousand or more enzymes.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); nt, nucleotide(s); and the like.

Introduction

Microbes can be designed and engineered to synthesize a variety of valuable chemicals, including pharmaceuticals, fuels, fabrics, foods and fragrances, and accomplish this at normal temperature and pressure and in aqueous environments. They accomplish these feats using enzymes, biocatalysts that are unmatched in their ability to accelerate chemical transformations with high specificity. To advance microbial bioproduction by improving its production efficiency and expanding its products profile, scientists sometimes identify a novel enzyme or engineer existing enzyme for high specificity and efficacy. For example, enzymes are discovered and engineered to enable the bioproduction of antimalaria drug, the complete biosynthesis of medicinal cannabinoids as well as the production of drop-in jet biofuel.

These efforts help advance microbial cell factories to replace traditional chemical synthesis industry with a significantly positive impact on both economics and environment.

The discovery and engineering of biocatalytic enzymes with novel functions have accelerated in recent years with the advance of DNA synthesis and sequencing technologies. Together, they allow comprehensive probing of enzyme sequence-function landscapes to identify enzymes with powerful new abilities. Key to this process is the ability to construct and test massive numbers of enzyme mutants, which typically relies on testing modalities that utilize fluorogenic reporters or chemical assays. Construction of such testing modalities can be complicated, lead to false-discoveries, and is sometimes only applicable to a small fraction of enzymes compatible with the selection or fluorescence assay.

One objective of this work is to provide a solution for ultrahigh throughput discovering novel biocatalysts using microscale mass spec. Consequently, the technology has utility for both academic and industrial applications, allowing academic scientists to perform unbiased functional annotation of enzymes, and industrial scientists to construct enzymes with new or enhanced activities. Here, the workflow and its proof-of-concept application in strain engineering for value added chemical production are described

General Workflow

Figure 1:
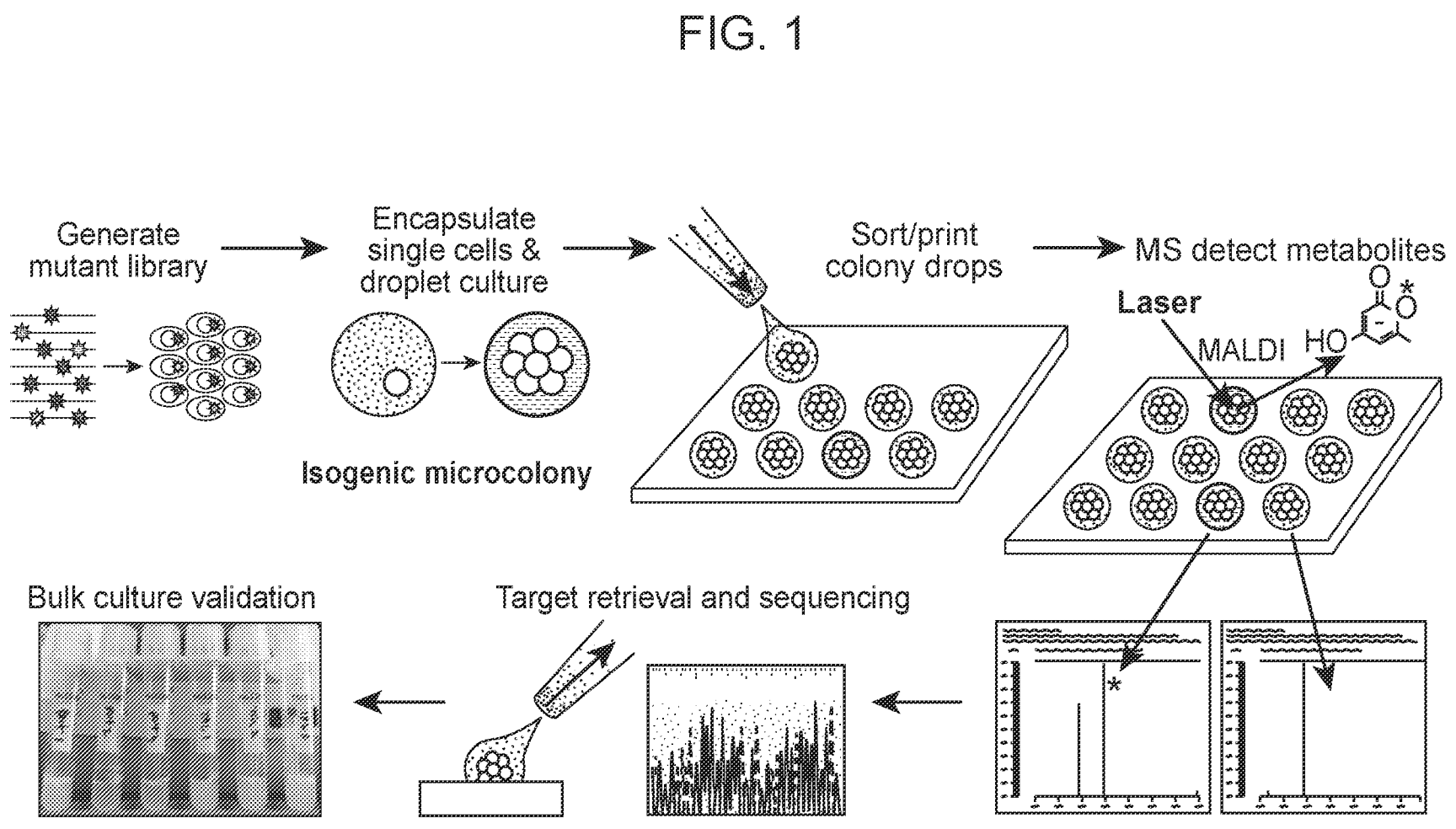

As shown by FIG. 1, there are five steps in the workflow, droplets preparation to form isogenic microcolony and target metabolites, target droplet sorting and printing to the unique picowell substrate, MALDI mass spec imaging and analysis, recovery of yeast-genome information from specific picowells of the picowell substrate, and verification of the screening results.

The first step is to encapsulate and culture individual yeast cells from the library in picoliter droplets, generating millions of isogenic microcolonies. This is accomplished using a cross-junction droplet encapsulation device that encapsulates single cells in droplets at kilohertz rates through a plug-squeeze mechanism following a Poissonian process. The generated emulsion is incubated so that isolated single cells can expand into isogenic microcolonies within each picoliter droplets. Moreover, according to needs, a droplet merging step can be performed after in-droplet culturing to ensure the production of target metabolites. Thus, the microcolonies in droplets provide both ample DNA and mRNA for sequencing and target metabolites for detection.

After the droplets are prepared, they are reinjected into the droplet printer and screened optically one by one at kilohertz rates. The droplets containing yeast microcolony are autofluorescent in FITC channel and the intensity of the autofluorescence is proportional to the cell density. Therefore, droplets with similar numbers of yeast are identified, sorted and printed into each picowell of the picowell substrate.

Once the arrays of droplets are form, micro colonies carrying sequences of interest are identified using a microscale mass spectrometry technology such as MALDI mass spec imaging. To enhance the sensitivity of MALDI mass spec imaging, different matrix should be tested to find out which one works best for the metabolites of interests. Modifications were made to the profile of the picowells of the picowell substrate to be bowl-shape (concave bottom surface) instead of cylinder. This special profile is not only preventing cells dries to the walls of picowell, but also concentrate the dried cells and chemicals of the droplet to the center of the picowell. From the experiment, this modification enhances the signal intensity of MALDI MS and makes the signal across the whole substrate more uniform.

Based on the result of the microscale mass spectrometry, the positions of the target picowells are found. There are at least two ways to recover the genome information from the picowells: one way is only to recover the materials from target picowells by using a glass micropipette. Through extracting the materials of each target picowells into individual PCR tubes, PCR with specific primers to the target gene is performed and then sequencing is done to find out the 'hit' sequences. The second way is to perform spatial RNA sequencing. The information of mRNA is recovered from all the picowells and linked with the mass spec imaging to find out the 'hit' sequencing.

After the 'hit' sequencings are identified, they are reinserted into the yeast to verify the screening efficiency. And based on that, second round screening can be performed.

Example 1: Depositing Droplets Containing Dyes into Picowells and Validation of Detection Sensitivity, Linearity, and Purity This experiment demonstrated that MALDI mass spectroscopy could be used to detect fluorescent dyes that were encapsulated in microfluidic droplets that were printed into the picowells.

Figure 2:
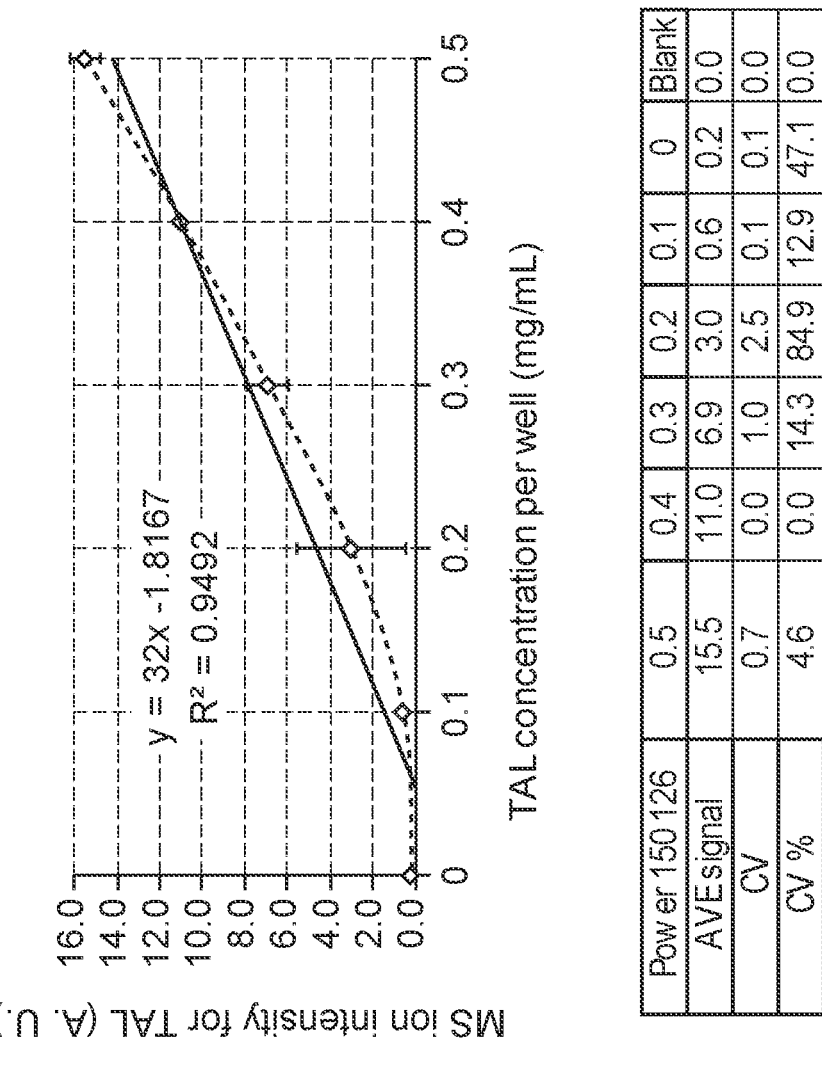
FIG. 2 shows quantification of pure chemicals by mass spec imaging. Droplets with different concentrations of triacetic acid lactone (TAL) are printed and scanned to get the mass spec ion imagining. From top to bottom, the concentration of TAL in droplets are 0.5, 0.4, 0.3, 0.2, 0.1 and 0 mg/mL respectively. Fluorescent dyes are added to aid droplet sorting and printing.
Figure 2:
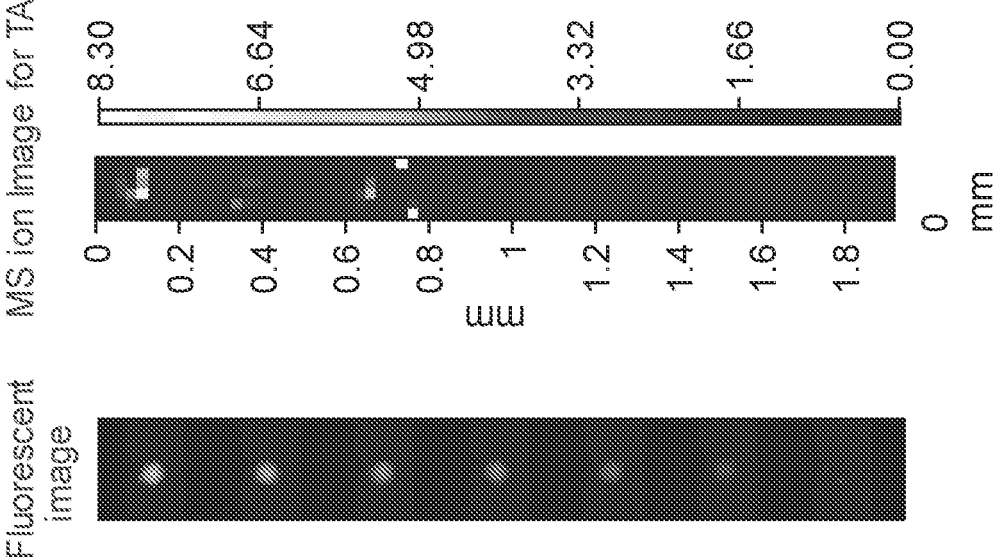

To demonstrate the accuracy and sensitivity of target metabolites detection using the approach with MALDI mass spec imaging, experiment was performed to print droplets containing different amount of TAL onto the picowell substrate (FIG. 2). Two types of droplets with 0.1 mg/mL TAL in water with 1 pM red fluorescent dye and water only with 1 pM blue fluorescent dye are encapsulated respectively. Then the droplets are mixed together and based on the color of fluorescence, six rows of droplets were printed on the picowells substrate: from top to bottom, for the first row was print five red droplets into each picowell. For the next rows were program the printer head to print one less red droplet and one more blue droplet into each picowell of the corresponding row. For example, each picowell of the sixth row contains only five blue droplets. After that the substrate was dried and prepare it with matrix. Then MALDI MS was performed imaging of the printed picowell substrate. As shown by the fluorescent and mass spec images, the mass spec signal of TAL is linear with the amount of it from the picowells of each row.

Figure 3:
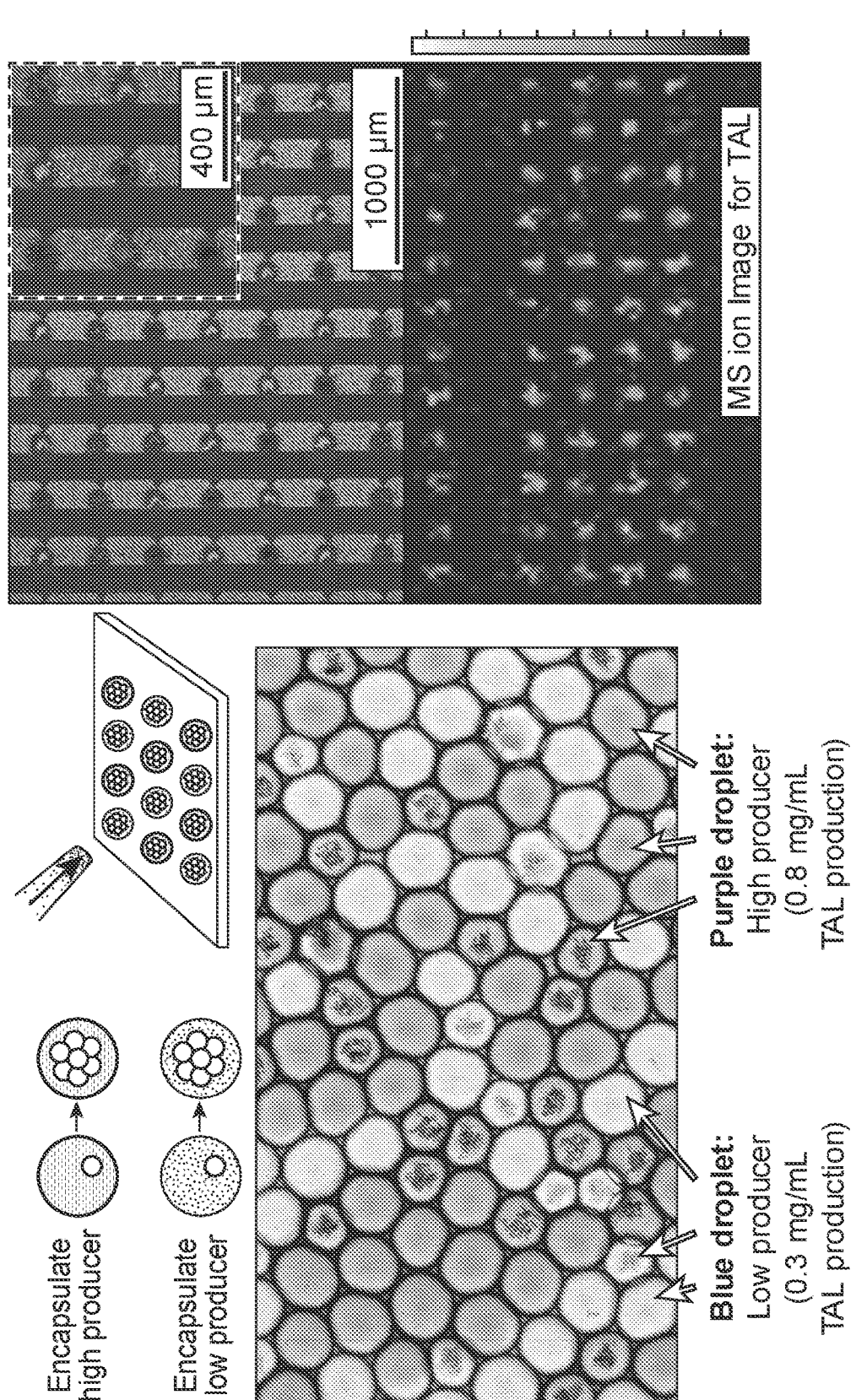
FIG. 3 shows the capacity of accurate quantification of TAL production of *Yarrowia lipolytica* yeast cultured in droplets using the described method. Two strains of yeasts are encapsulated with droplets. The high producer which can produce 0.8 mg/mL TAL is labeled with purple fluorescent dye and the low producer which can produce 0.3 mg/mL TAL is labeled with blue fluorescent dye. Bottom left image shows a mixture of droplets containing those two types of yeast after three days incubation. Top right image shows the overlap image of the tranilluminescent and fluorescent channels of the microwell substrate after droplet printing and matrix addition. Bottom right image shows the mass spec ion imaging for TAL of the same substrate. Scale bar is 1 mm.

The proposed method depends on minimal cross contamination of target metabolites between droplets. To investigate cross contamination, two strains were cultured of *Yarrowia lipolytica* with different levels of TAL production in droplets together for three days, print them in a checkerboard pattern and verify the level of TAL by MALDI mass spec imaging (FIG. 3). Two strains were prepared and encapsulated of *Yarrowia lipolytica*, the droplets containing yeast that can produce 0.8 mg/mL TAL are labeled with 1 pM red fluorescein dyes and the droplets containing yeast that can produce 0.3 mg/mL TAL is labeled with 1 pM blue fluorescein dyes respectively. The two types of droplets were mixed together and incubated for 3 days. Based on the fluorescent labels of the droplets and the auto-fluorescent signal from the yeast, a checkerboard pattern was printed of those droplets, prepare the printed substrate with matrix and perform MALDI MS imaging in a similar fashion as previously described. As illustrated by the fluorescent and mass spec images, the mass spec signal of TAL shows a checkboard pattern that agrees with the fluorescent signal.

Example 2: Depositing Droplets Containing Yeast Cells into Picowells and Detecting Metabolites Generated by the Cells by Mass Spectroscopy Screening for TAL Production in *Yarrowia lipolytica*

This experiment involved printing microfluidic droplets containing different yeast strains into picowells of a substrate. The yeast cells metabolize and generate TAL, which was then detected by MALDI mass spectroscopy. This experiment demonstrated the feasibility of detecting the production of metabolites by cells deposited into wells as part of droplets.

Figure 4:
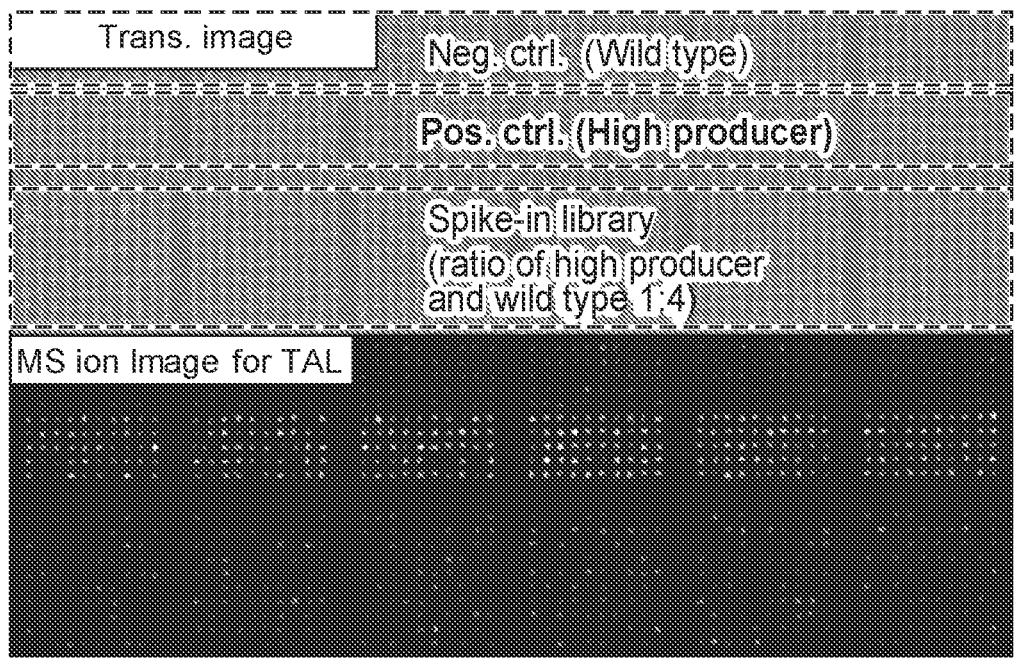
FIG. 4 shows screen test of a spike-in TAL production *Yarrowia lipolytica* mock library using the described method. The images on the left show the same area of the microwell substrate under tranilluminscent and mass spec ion image modes. The top right image shows the analysis result of the mass spec ion image for TAL by MATLAB. To determine which microwells of the spike-in library are positive, a threshold value is set based on the mass spec ion intensity for TAL from microwells of the positive and negative controls. If the mass spec ion intensity of the microwells of the mock library is higher than the threshold, it is considered as positive and marked with a red dot. Vice versa, a green dot is placed on top for microwells considered as negative.
Figure 4:
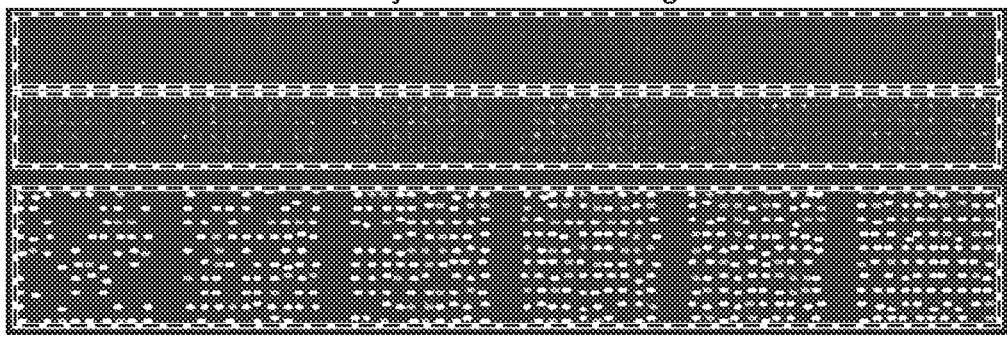
Figure 4:
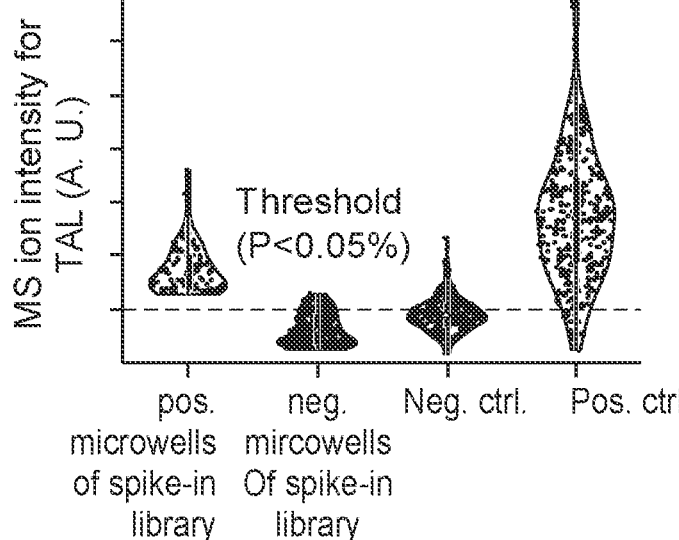

To mimic the real library, wild type *Yarrowia lipolytica* strain (nonproducer) was spiked in with a strain that can produce 1 mg/mL TAL to make the mock library (FIG. 4). The spike in ratio is 1:4. Three types of droplets were prepared and encapsulated: one contains only wild type yeast as negative control, one only contains the yeast that can produce 1 mg/mL TAL as positive control and the one with the mock library. From up to bottom, for the first five rows, droplets were printed of negative control. For the second five rows, the droplets were printed of positive control and for the next ten rows, the droplets were printed of the mock library. After that in a similar way as before, MALD mass-spec imaging was performed. Then analysis was conducted of the result with a customized MATLAB program to identify the location of 'hit' picowells according to the z score of the picowells that containing positive control and negative control droplets respectively. As shown by the violin plot of FIG. 4, the ratio identified by the mass spec imaging agrees with the initial spike-in ratio of the library. To further demonstrate the capability of the method for screening, recovery of genome information was performed from the 'hit' picowells using glass micropipettes. It was chosen to recover the materials from five picowells of positive-control droplets, five of negative-control droplets, five of library 'hit' ones and five of library 'negative' ones. Transfer them into twenty individual PCR tubes. Then PCR was done of all the tubes, run the gel electrophoresis to check the length of DNA and sequence the product by Sanger sequencing. As shown by the gel and sequencing results, it was recovered the target gene from four out of five target genes from picowells of the positive-control droplets, five out of five from picowells of the library 'hit' droplets and none from ones of the negative-control droplets or the library 'negative' droplets.

Figure 5:
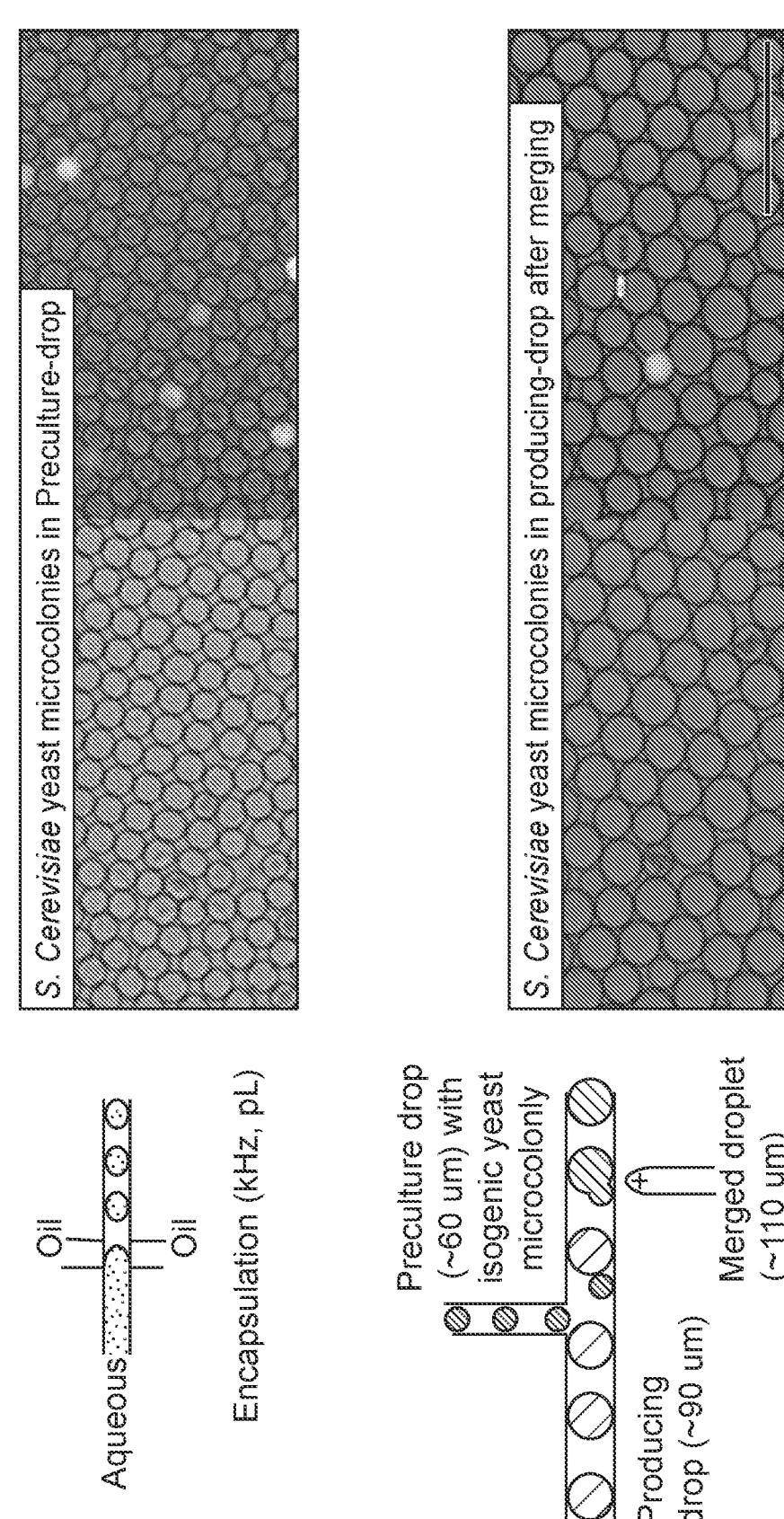
FIG. 5 shows quantification of naringenin production of *Saccharomyces cerevisiae* strain that requires a chemical induction for production using the method. The first image shows the droplets with pre-culture medium contain the yeast microcolonies after three-day incubation and the second image shows merged droplets with production medium contain the yeast microcolonies after another three-day incubation for production inducation. The third diagraph shows the mass spec ion intensities of naringenin for *Saccharomyces cerevisiae* yeasts after this two-step culture process in droplets. The strains can be detected as producing 50 μg/mL and 350 μg/mL naringenin respectively. For the yeast strain that can produce 350 μg/mL naringenin, a titer of it with 10, 100 and 1000 folds dilution is tested as well. The bottom histogram shows the quantification result for each strain. Scale bar is 400 μm.
Figure 5:
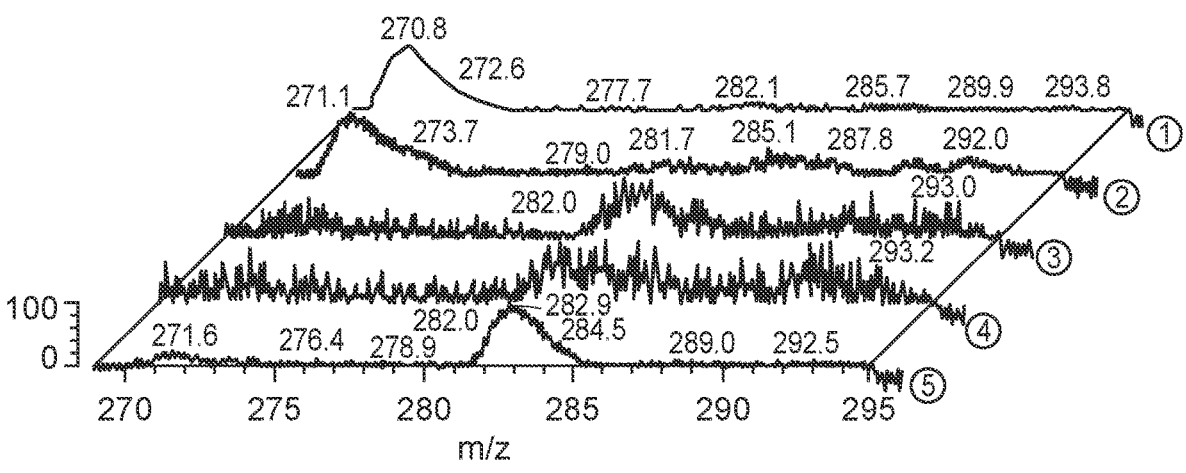
Figure 5:
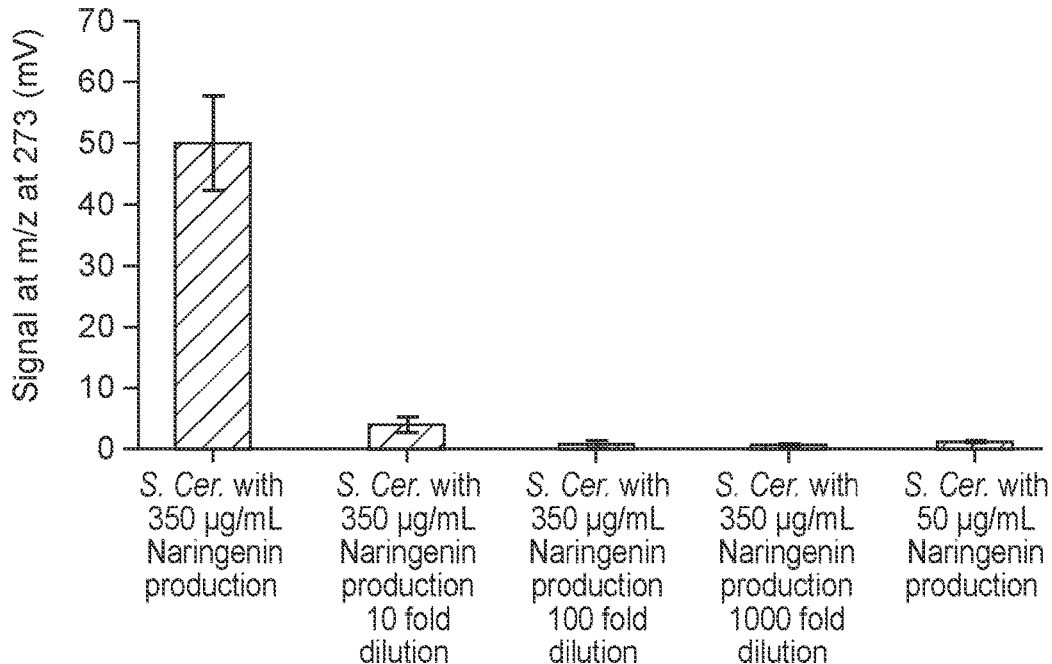

Example 3: Depositing Droplets Containing Yeast Cells that Involves Production Induction into Picowells and Detecting Metabolites Generated by the Cells by Mass Spectroscopy Screening for Naringenin Production in *Saccharomyces cerevisiae* Through Droplet Microfluidics Enabled Production Induction To demonstrate the generosity of the method, this technology was also applied to two *Saccharomyces cerevisiae* strains which can produce 50 μg/mL and 350 μg/mL naringenin respectively (FIG. 5). Note here that unlike the previous described culture workflow, two-step in-droplet culturing was performed here to accommodate the need for production induction as naringenin is toxic to the cells. First the yeast cells were cultured in 60-μm droplets containing pre-culture yeast medium to form isogenic microcolonies.

Then an 80-μm droplet was merged containing production yeast medium that contains production inducing chemical with droplets containing isogenic microcolonies for the production induction. Following culture the merged droplets of the two *Saccharomyces cerevisiae* strains, it was confirmed the production difference of the two strains through using MALDI MS measurement of merged droplets. For the *Saccharomyces cerevisiae* strain that can produce 350 μg/mL Naringenin, the merged solution was diluted with producing medium to 10, 100 and 1000 folds respectively and then tests them with MALDI MS instrument again. As shown in FIG. 5, mass spec signal was able to detect naringenin from the microcolonies of the high producers that cultured in droplets even the solution is diluted by 10 folds.

Example 4: Metabolite Profiling of Microbes Using Microscale Mass Spectrometry

Introduction

Microbes are increasingly considered as critical contributor to human health. Detecting pathogenic microbe through metabolites profiling has been demonstrated as powerful approach for clinical diagnosis. Furthermore, analyses focusing on commensal microbes have yielded a deluge of knowledge of their impact on human health. The innovation is well positioned to tackle challenges and applications in high throughput microbe analysis. For example, microscale mass spec technology can be used for drug metabolism analysis of microbiome: by allowing microbe culturing and drug testing in droplets, the technology can identify drug metabolizing microbes and their reaction and products in high throughput. This would be valuable for personalized medicine. As a proof-of-concept, the microscale mass spec has been applied to demonstrate its capacity of distinguishing two different yeast species.

Workflow

Two different species of yeast cells (*Yarrowia lipolytica* and *Saccharomyces cerevisiae*) are used in this demonstration. Yeast are inoculated from a frozen glycerol stock to culture tube with 2 mL culture medium (20 g/L glucose, 6.7 g/L YNB with ammonium sulfate and 0.79 g/L CSM) for 16 hours at 30° C. The yeasts are then pelleted and re-suspended with fresh culture medium. The yeast cells are counted and diluted to $3 \times 10^7$ cells per mL with fresh culture medium. This cell concentration is chosen to ensure roughly 1 in 10 droplets containing a single yeast cell when encapsulated. Then the dilutions of these two types of yeast cells are encapsulated independently into millions of 80-μm droplets by co-flowing the diluted yeast cell medium and Novec HFE-7500 oil (3M) with 2% EA surfactant using a droplet encapsulation device. Each of the droplets are collected into a 5 mL syringe which is then positioned vertically in an incubating shaker for three days at 30° C. to form isogenic microcolonies in droplets. The droplets are printed onto the substrate followed by MALDI MS imaging.

Results

Figure 6:
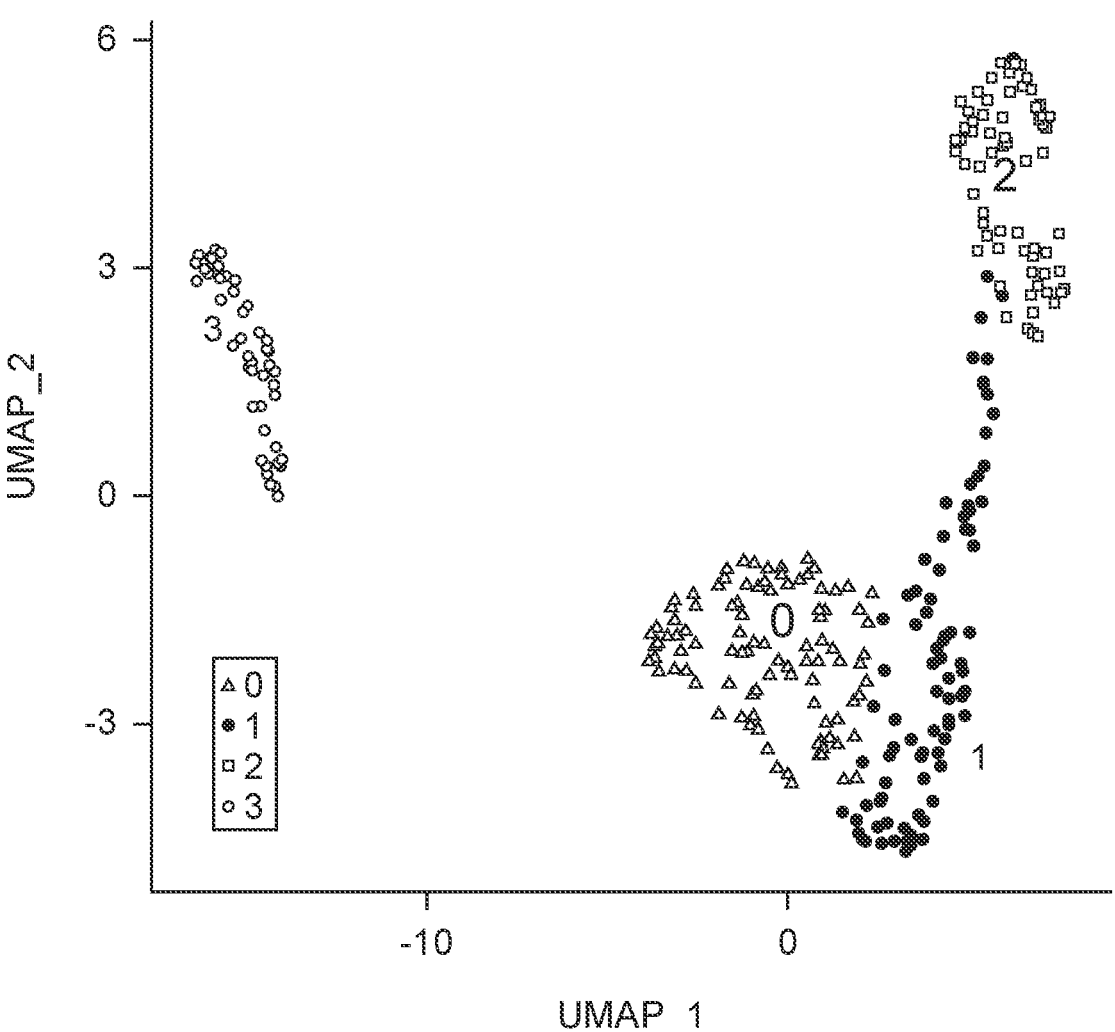
FIG. 6 shows the example of using the method to differentiate biological materials. Mass spec imaging of two types of droplets containing yeast microcolonies and four types of droplets containing single mammalian cells are shown. Top images shows the same area of the printed substrate in tranilluminacent and mass spec ion imaging modes. Bottom is the uMAP analysis based on the mass spec signal of each microwells. 4 groups identified by uMAP is labeled with 0, 1, 2 and 3. From that, we also label each microwells at the mass spec ion image with its group number based on the uMAP groups

As shown by FIG. 6, by feeding the mass spectrometry data into UMAP based multi-dimension reduction algorithm, it was possible to cluster yeast colonies based on their metabolite profiles.

Example 5: Metabolite Profiling of Mammalian Cells

Introduction

Cells are basic structural units that play vital roles in the functioning of living organisms. Analysis of the chemical composition and content of a single cell plays a vital role in ensuring precise investigations of cellular metabolism. To this end, it was attempted a proof-of-concept metabolite analysis of mammalian cells using the microscale mass spectrometry technology. By encapsulating cells in droplet before mass spectrometry analysis, this platform is more versatile comparing with existing technologies as the (1) cells can be lysed before mass spec analysis without loss of analyst and (2) cells can be co-culture before mass spec analysis to enable the discovery of roles of metabolites in cell-cell communication.

Workflow of Proof-of-Concept Experiment

K562, 3T3 and Raji cells (ATCC) are cultured in 75 cm2 flasks in the presence of Dulbecco's modified Eagle's medium (DMEM) supplemented with 10% fetal bovine serum (FBS) and 1× Penicillin-Streptomycin at 37° C. and 5% C02. Cells are treated with 0.25% Trypsin-EDTA and washed with media to generate cell suspensions. The viability and cell concentration are counted by a TC20 automated cell counter (BioRad). Cell suspensions are diluted to 1 million/mL in media. Suspensions are pelleted at 400 g for 3 min and resuspended in 1 mL DPBS. The K562 suspension is treated with 1 μg/mL of Calcein Green (Thermo-Fisher) the 3T3 suspension is treated with 2 μg/mL of Calcein Red (Thermo-Fisher) and Raji suspension is treated 1 μg/mL of Calcein Blue (Thermo-Fisher) with for 15 min at 37°, followed by the addition of 4 mL media. Suspensions are pelleted and resuspended in media. Cells are mixed together in a 1:1 ratio and diluted in DPBS to form a final concentration of 250 k/mL. This cell concentration is chosen to ensure roughly 1 in 20 droplets containing a single mammalian cell when encapsulated. Then the dilutions of these three types of mammalian cells are encapsulated independently into millions of 80-μm droplets by coflowing the cell medium and Novec HFE-7500 oil (3M) with 2% EA surfactant using a droplet encapsulation device. Then droplets are placed on ice and ready to be used for droplet printing. Droplets are printed onto the picowell substrate in a one-droplet per picowell fashion followed by MALDI imaging analysis.

Results

As shown in FIG. 6, by feeding the mass spectrometry data into UMAP based multi-dimension reduction algorithm, it was possible to cluster cells based on their metabolite profiles.

Figure 7:
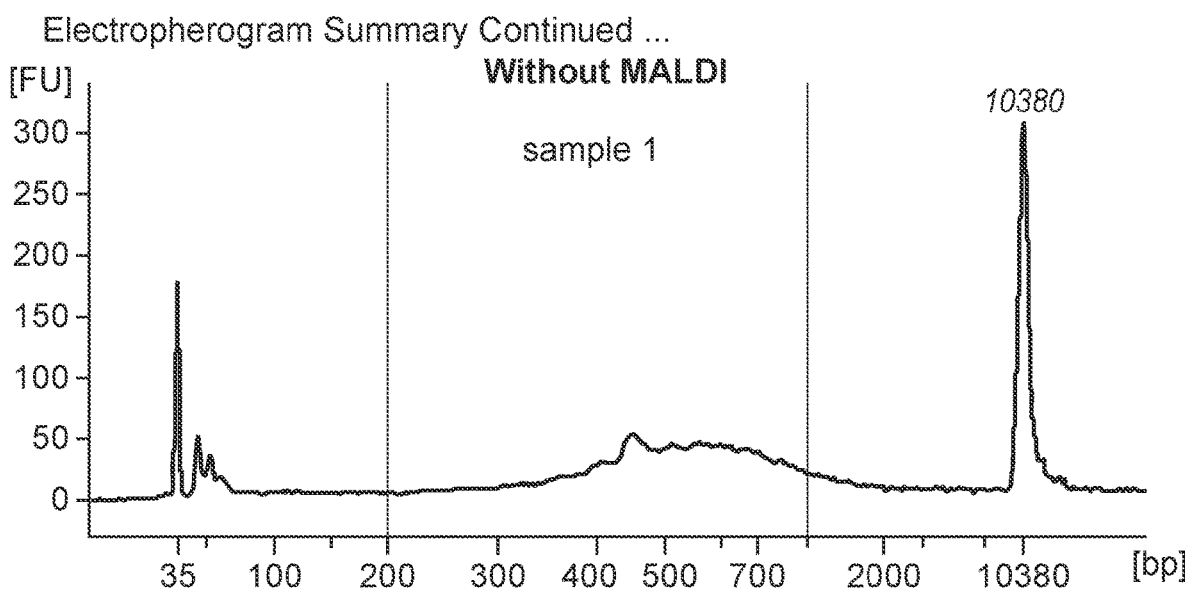
FIG. 7 shows messenger RNA transcripts can be recovered from *S. cerevisiae* microcolonies in picowells post MALDI imaging. After MALDI imaging, single cell mRNA expression information can be recovered through single cell RNA-seq workflow. This gene expression information in combination of mass spec profile is valuable for many biological applications including pathway optimization.
Figure 7:
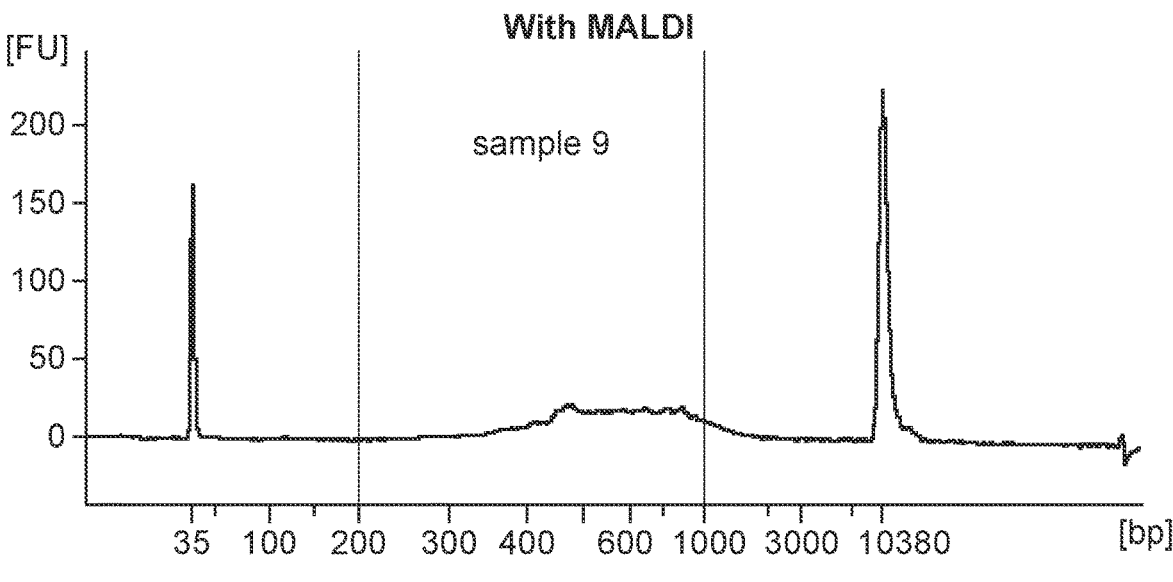
Figure 7:
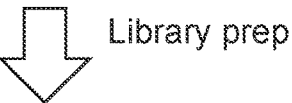
Figure 7:
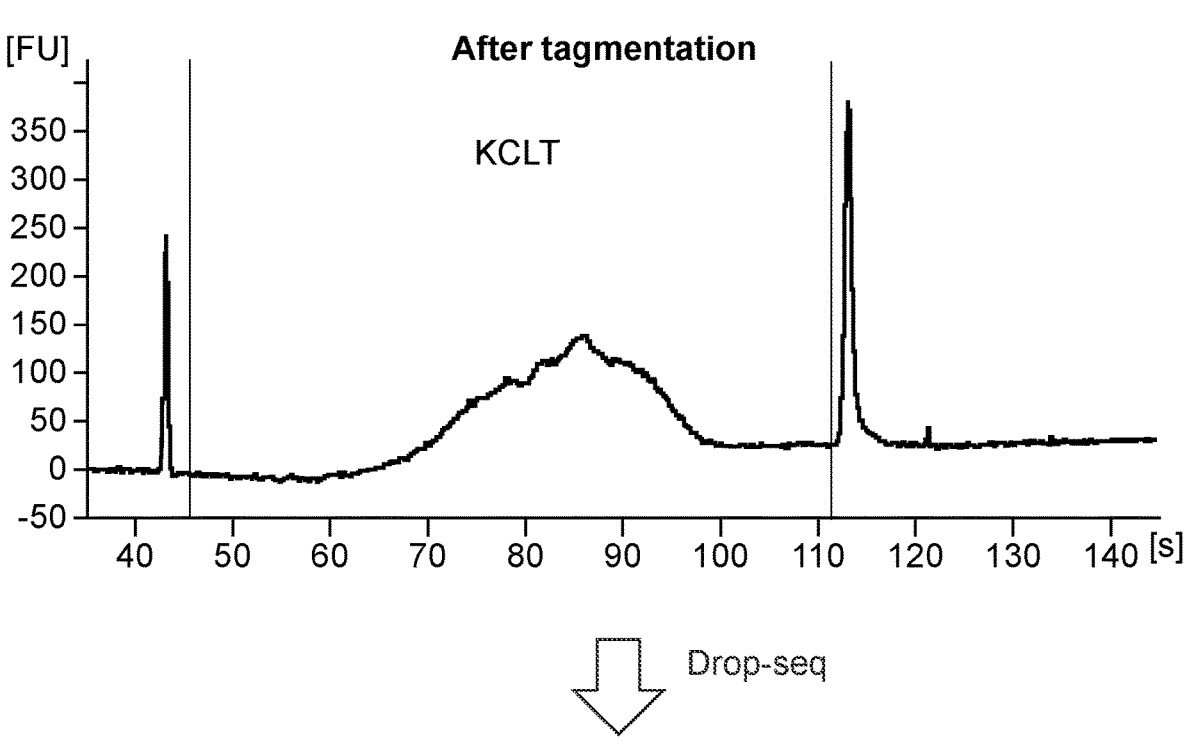

Example 6: Integrating Transcriptome and Metabolome for High Throughput Multimodal Analysis of Biological Entities Introduction Bioproduction enables cheap and efficient synthesis of a large array of compounds under ambient conditions, ranging from direct methane-methanol conversion to complex drugs and natural products with multiple stereocenters that are otherwise difficult, if not impossible, to be chemically synthesized under similar costs and conditions. Achieving high biosynthesis yields involves optimizing expression level of each pathway enzyme to increase the flux of substrates through the pathway and prevent accumulation of unwanted inhibitory intermediates. However, biosynthesis often involves multiple steps; for example, efficient triacetic acid lactone production by *Yarrowia lipolytica* involves tuning expression of 5 genes, while that of opioid hydrocodone by *Saccharomyces cerevisiae,* 23 genes. Identifying, or "debugging", pathway bottlenecks thus becomes increasingly difficult with each additional step as the combinatorial complexity grows rapidly. This problem was overcome by developing a high-throughput platform to screen a large pathway library of such combinatorial expression levels. This method is based on the fact that the "soft ionization" nature of MALDI results in relatively mild destruction of the samples being investigated, and it has been discovered that both DNA and RNA can be recovered from yeast after MALDI imaging (FIG. 7).

Workflow and Results

Figure 8:
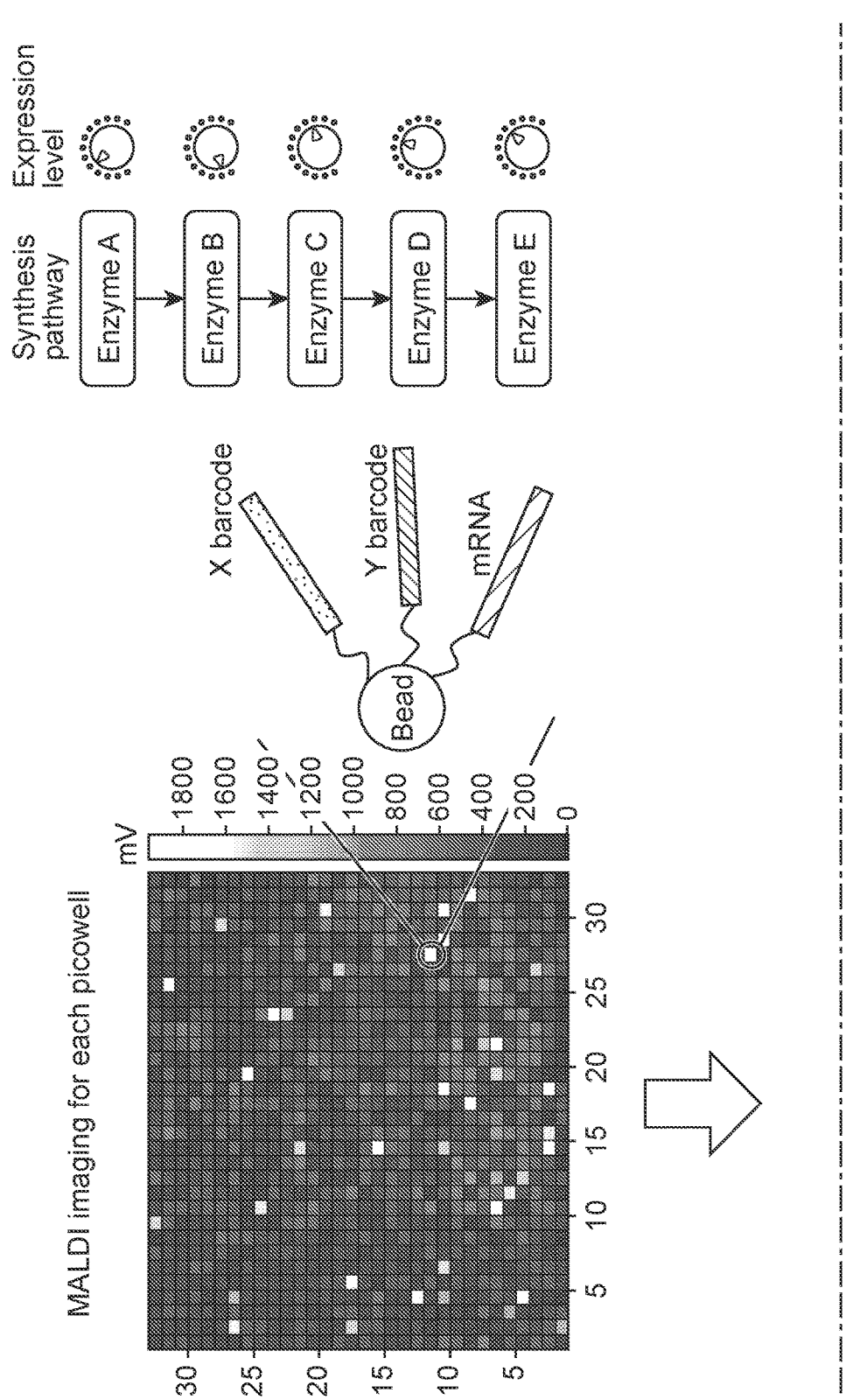
FIG. 8 shows schematics for applications of our metabolomic-transcriptomic co-profiling platform. a) The mRNA reads from each picowell are mapped by the spatial (X-Y) barcodes. Expression level of each synthesis gene is recovered and can be correlated with the production yield information from MALDI imaging. b) For protein mutagenesis library, our platform allows direct mapping of the fitness landscape based on enzymatic activity. The "inaccessible" evolutionary paths are hindered by non-functional or lethal evolutionary intermediates.
Figure 8:
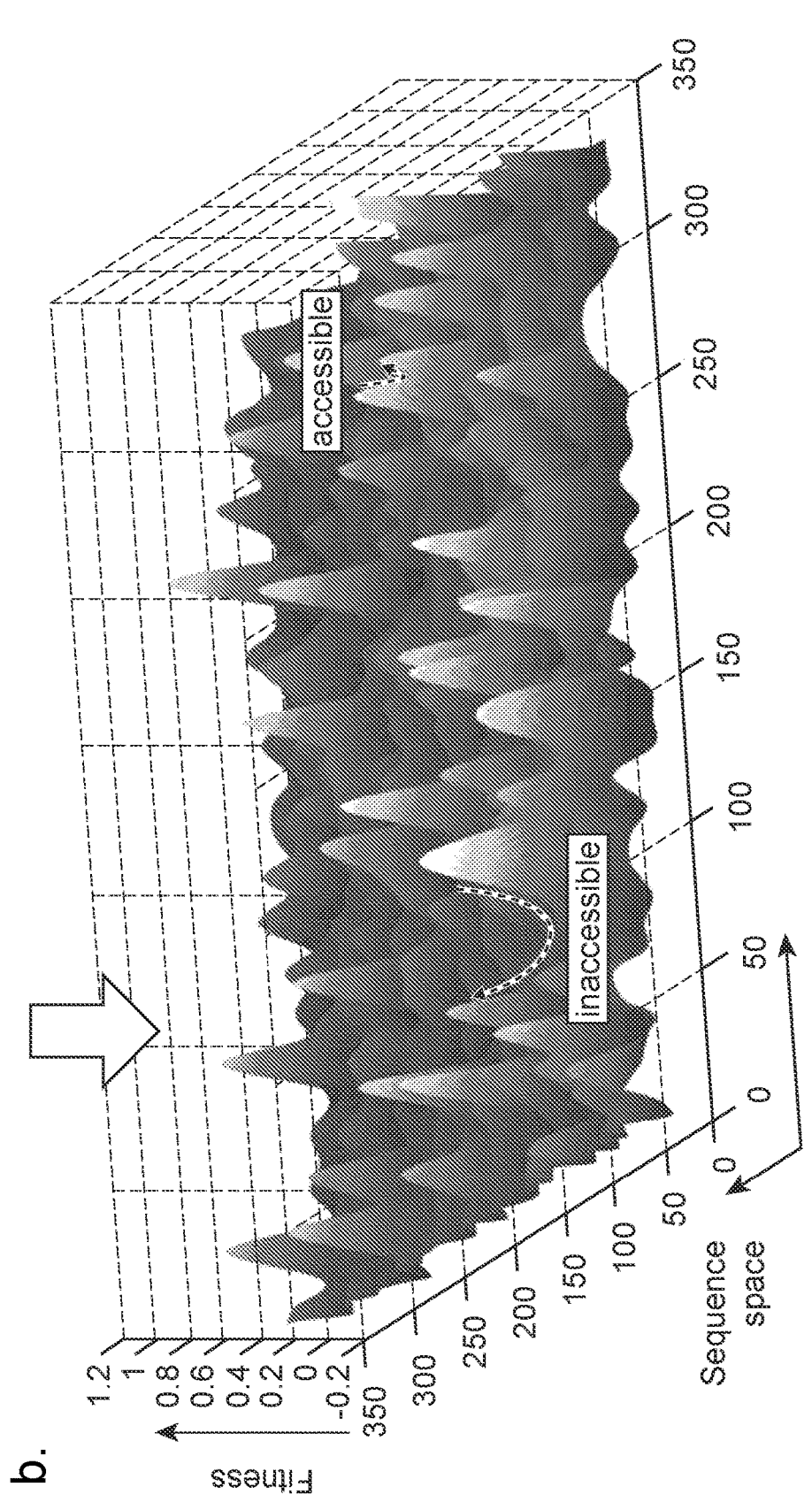

Briefly, after preparing the library yeast strains, single yeast cells were encapsulated with culture medium into droplets and allow them to grow into isogenic microcolonies to synthesize desired metabolites. The droplets are then printed into picowells, and the MALDI matrix is applied by air brush. The production yield is determined by MALDI imaging. The MALDI matrix is then gently washed away by ice-cold 70% ethanol. Using sciFLEXARRAYER S3 (Scienion AG), the picowells are then "barcoded" by DNA oligos encoding spatial information. The yeast cell walls are lysed by printing droplets with zymolyase. Multiple drop-seq beads resuspended in lysis buffer are then printed into each picowell to recover both spatial oligos and mRNA transcripts. The drop-seq beads are spun out from picowells by centrifuge, collected and then washed for sequencing library preparation per standard drop-seq protocol. Transcript reads are mapped to each picowell by integrating the information from bead barcodes and the captured spatial barcodes (FIG. 8, panel A). The production yield from each library strain can thus be correlated with the expression levels of not only all the pathway genes, but also the intrinsic transcriptome that may impact synthesis.

In addition, the method can be applied to protein engineering, where multiple sites of the rate-limiting enzymes are randomly mutated. Since Drop-seq recovers the 3'-end sequence of the captured transcripts, the identities of cell strains can be easily mapped with high-throughput by introducing a cell barcode to the 3'-end of the enzyme gene during library strain generation. This allows direct mapping of fitness landscape based on catalytic activity (FIG. 8, panel B). To date, such high-throughput for sequence-function mapping of proteins can only be achieved by fluorescence readouts, instead of direct detection of the reaction products. A comprehensive protein fitness landscape can allow us to direct in vitro evolution across inaccessible evolutionary paths (the "valleys" in fitness landscape; FIG. 8, panel B) that are hindered by non-functional or lethal evolutionary intermediates, and explore novel variants with activities and properties superior than their parental strains.

This method can be extended to single-cell metabolomic and transcriptomic co-profiling. It has been shown that metabolic features are divergent in tumor cells with identical genomic background due to various microenvironment stimuli and cell-intrinsic processes. The platform may provide orthogonal information that is important for uncovering such combinatorial oncogenic drivers.

Example 7: Additional Negative and Positive Control Test

Figure 9:
FIG. 9 shows proof-of-concept test demonstrates screening based on MALDI MS imaging.
Figure 10:
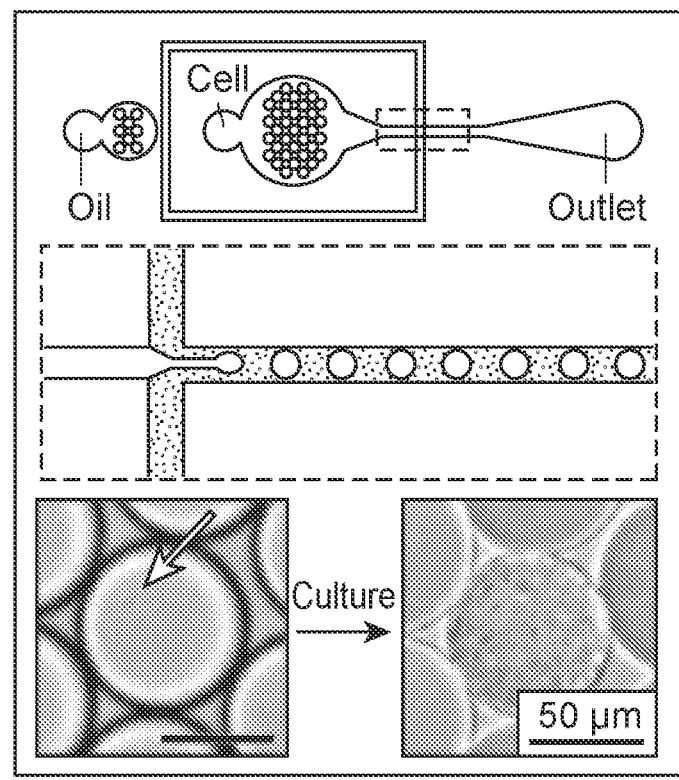
FIG. 10 shows an exemplary embodiment wherein cells are encapsulated in droplets.
Figure 10:
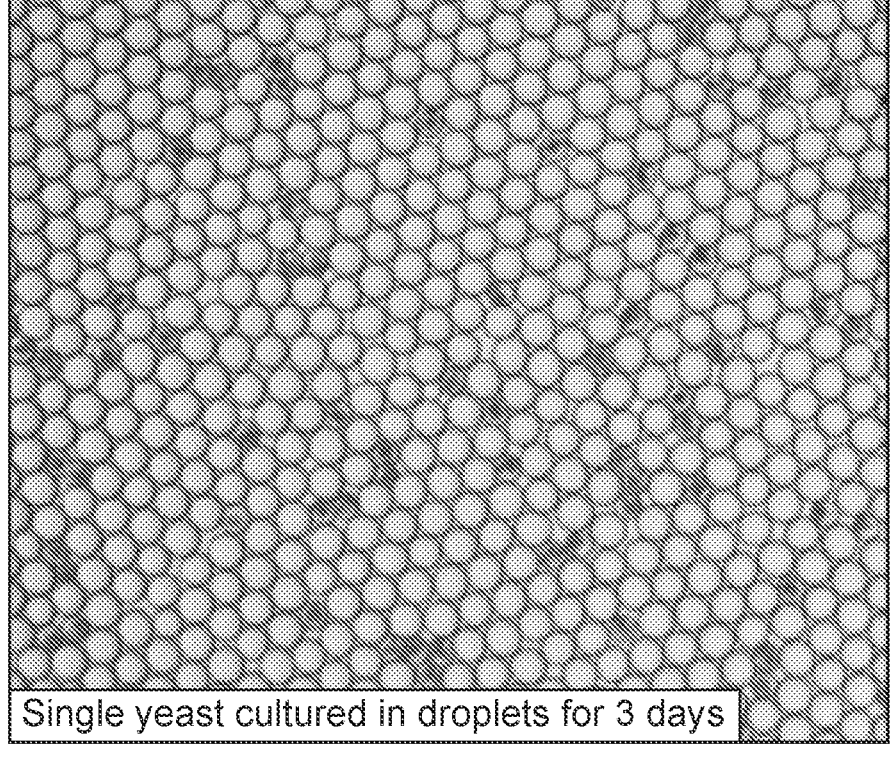
Figure 11:
FIG. 11 shows exemplary substrates with microwells.
Figure 12:
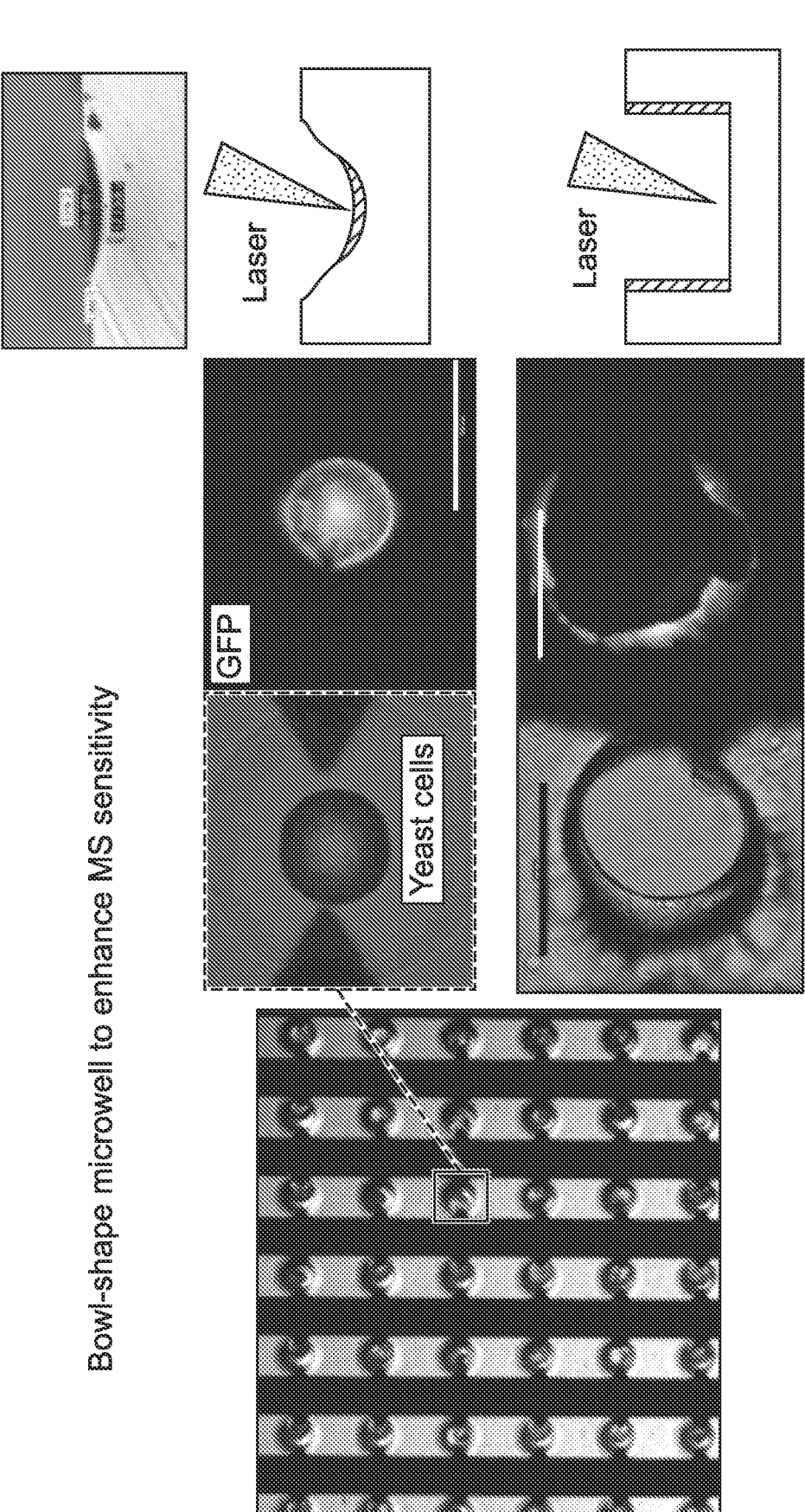
FIG. 12 shows how MALDI mass spectrometry sensitivity was increased with a bowl-shaped well with a concave bottom surface. With a flat bottom, as the liquid evaporated it preferentially moved towards the walls, and the green fluorescent protein was mostly located on the walls, where it was hard to detect by MALDI mass spectrometry. But with the curved well, evaporation left most liquid in the center of the well, where it could be detected by the mass spectrometry laser.
Figure 13:
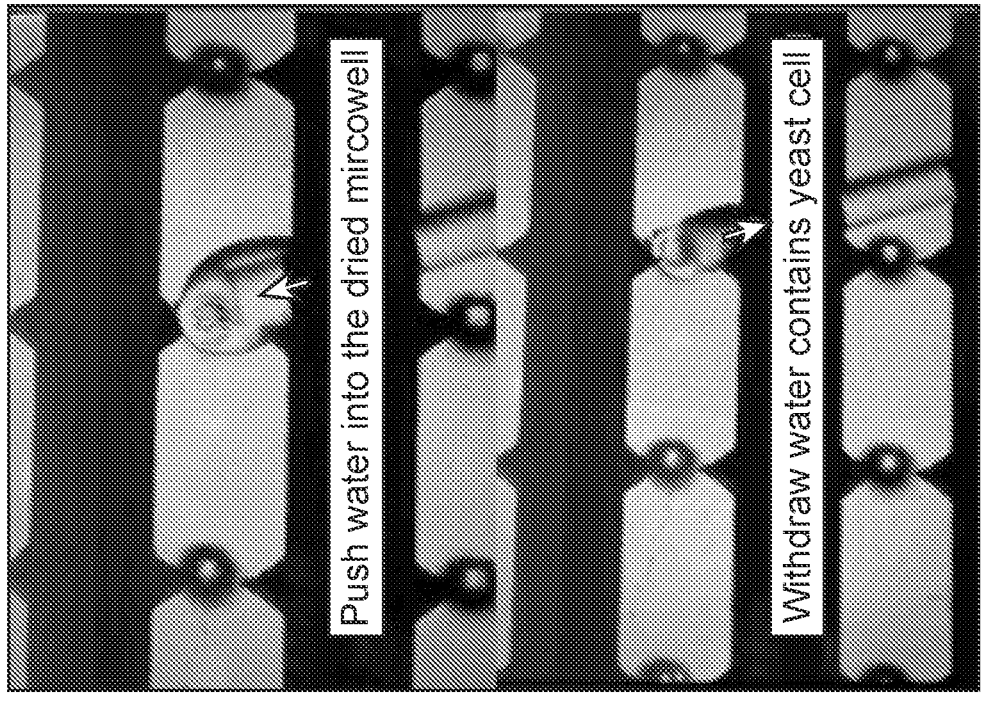
FIG. 13 shows how water is pushed into the dried microwell, and then withdrawn, to recover biological materials post MALDI MS analysis for genomic analysis.
Figure 13:
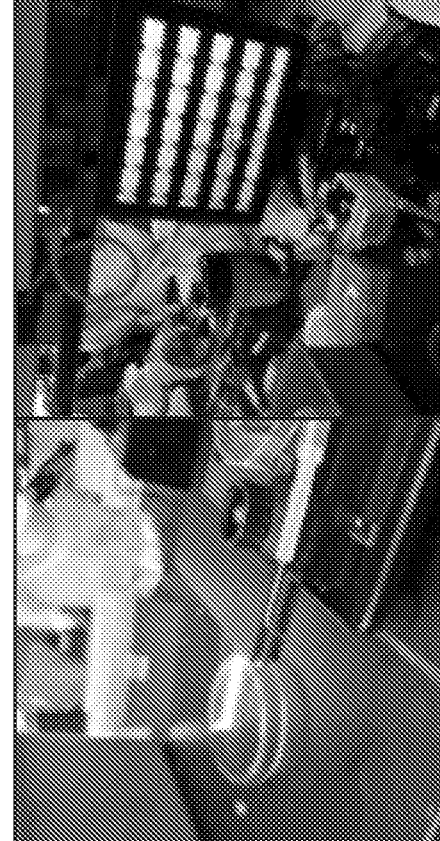
Figure 14:
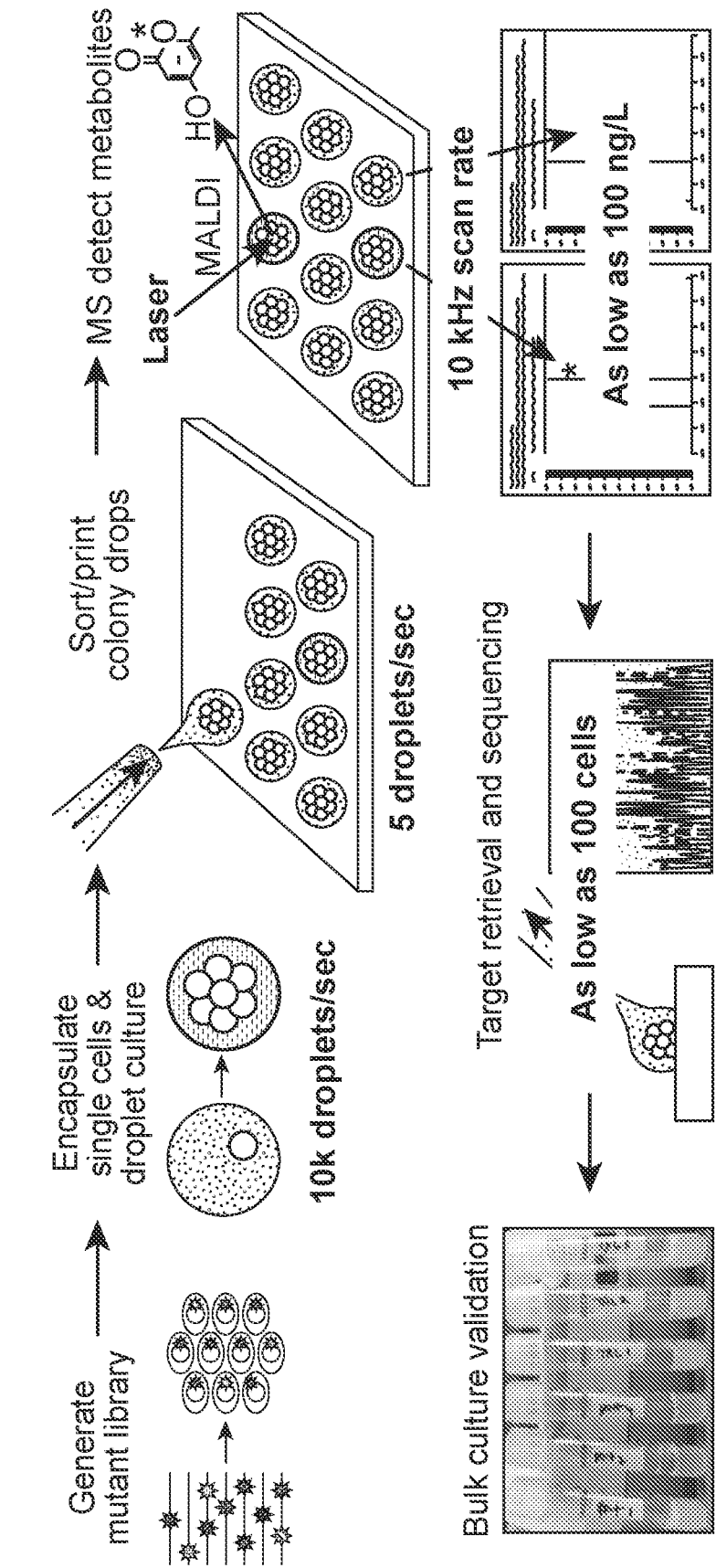
FIG. 14 shows exemplary throughout and sensitivity of each step in the workflow.

Proof-of-concept experiments has been performed to demonstrate the feasibility of our proposed method as shown by FIG. 9: (1) Enzyme library construction: a yeast strain of *Yarrowia Lipolytica* (HYL) have been engineered from the wild type (WYL) to produce a specific metabolite, triacetic acid lactone (TAL), by inserting specific genes into the chromosome of the yeast. By HPLC, the production level of TAL is 0 g/L and 1 g/L for WYL and HYL respectively. (2) Enzyme expression through in droplet single cell culture: Droplets (~100 μm) are made with yeast cells from each strain respectively. The cell density is adjusted to make sure there is one cell per droplet in average. Cell culture medium is optimized to enhance the growth of single yeast in droplet and minimize the interference with MALDI MS. (3) Enzyme loading into droplet array: After days of single-yeast culture in droplets, isogenic microcolony is formed in the droplet and we sort out the droplets containing similar numbers of yeast and print the sorted droplets into an array of customized-microwells on a standard glass slide in a one droplet per microwell fashion. In the first 5 rows we print only the droplets containing WYL; in the next five rows we print only the droplets containing HYL and in the next 10 rows we print a mock library by mixing droplets of HYL with droplets of WYL in 1 to 4 ratio. (4) Mass spec analysis of droplet array: After droplet printing, the glass slide is dried in nitrogen for 1 hour and then matrix is air brushed on top of the slide. A Bruker Rapiflex® is used to produce the mass spec imaging based on MALDI. (5) Gene recovery from a mock library based on mass spec imaging and validation. Based on the mass spec imaging, remaining yeasts in the microwell is recovered by a glass micropipette. Then PCR is performed. Both gel and sequencing data show the target gene inserted into the HYL for TAL production is recovered based on the mass spec imaging.

Example 8: Cluster Analysis for Improved Study of Enzymes

As will be discussed below, existing methods were modified by adding the step of performing cluster analysis on the mass spectroscopy data from many different samples. It has been shown that such cluster analysis has significantly helped in identifying enzymes mutants that generate new metabolites.

As described in Examples 1-7 above, experiments were performed wherein the methods assessed for the production of certain compounds, such as triacetic acid lactone (TAL), by certain enzymes. As described in Example 1, two different strains of *Yarrowia lipolytica* that produce different levels of TAL were cultured. As shown in Example 2, cells of these yeast strains were encapsulated in droplets, printed to addressable locations, and mass spectroscopy was able to detect the different levels of TAL produced by each strain.

In addition to measuring the level of a known metabolite, it could be useful to be able to screen for production of new and different metabolites. For instance, the method could begin by identifying a desired metabolite along with determining or estimating its mass spectrum. As such, the methods described above could be repeated with different strains or mutants of a known enzyme, and the particular features of the mass spectrum of the desired new metabolite could be searched for. As an example, if the current metabolite has a primary peak at 188 m/z and the desired new metabolite is estimated to have a primary peak at 144 m/z, the mass spectra of many samples could be scanned for a particular enzyme or variant that shows a large peak at 144 m/z, and optionally a decrease in the peak at 188 m/z.

However, such a method would involve certain aspects such as: (i) the need to select a particular new metabolite to search for; (ii) knowledge or estimation of the mass spectrum of the new metabolite; (iii) a metabolite that leaves a sufficiently distinctive signature in mass spectroscopy; and (iv) a mass spectroscopy signature that does not overlap too much with other compounds already present in the biological fluid.

In search of an improved procedure, a method was developed that involved performing cluster analysis on the mass spectroscopy data of many different samples. Instead of manually checking each spectrum for a single indication of a single new metabolite (e.g. a peak at 144 m/z), cluster analysis processed many individual data points (e.g. the value at 19 different m/z values for each of 500 different samples) to generate a cluster map showing proposed clusters. After identifying the clusters, each cluster can be assigned to a particular category, such as: (i) a reference cluster producing the existing metabolite, (ii) a cluster possibly producing a new metabolite, (iii) an error cluster of erroneous samples. Afterwards, a certain number of samples from the new metabolite cluster can be investigated, e.g. by omic analysis, by mass spectroscopy to identify the possible new metabolite, or by other chemical techniques to identify the possible new metabolite.

Thus, the cluster analysis step can reduce the time and effort necessary to identify enzyme variants that produce a new metabolite by highlighting particular samples. The cluster analysis step also achieves this result without the need to pre-selecting which new metabolite to search for, and without the need to pre-determine the mass spectra of the new metabolite.

Furthermore, the method involving cluster analysis can detect production of a new metabolite even if the new metabolite itself is not easily detectable by mass spectroscopy. In particular, production of a new metabolite will alter the overall metabolism of the cell (e.g. alter the central metabolism of the cell), which will have secondary effects on the levels of other compounds which can be detected by mass spectroscopy. Thus, even if the identities of these other compounds is not determined, and even if peaks in the mass spectra are not assigned to particular compounds, the cluster analysis can show that the overall metabolism of the cell has significantly changed, suggesting significant production of a new metabolite.

Figure 15:
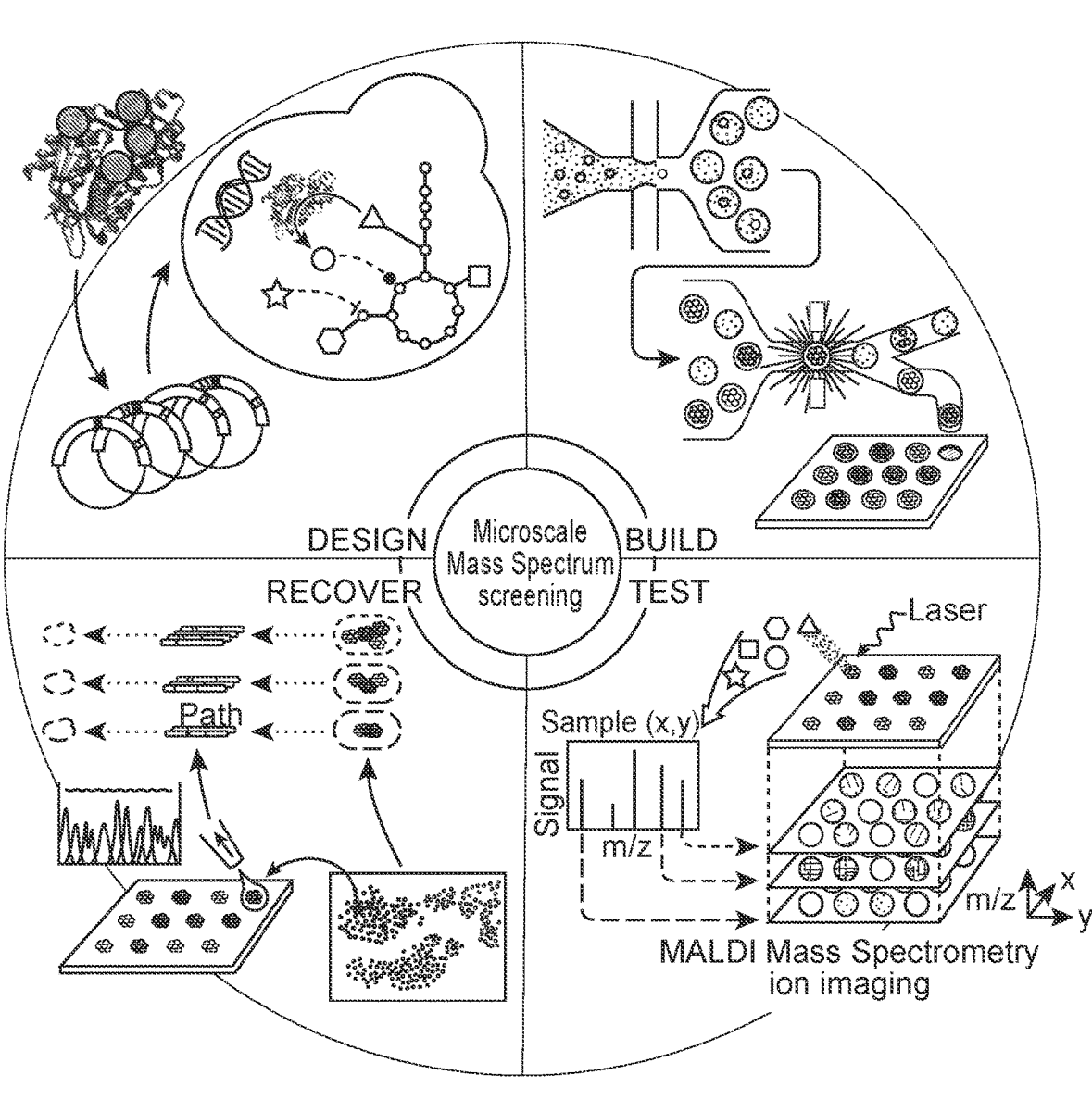
FIG. 15 shows metabolic biosensing with microscale mass spectrometry provides a general strategy for screening enzymes. Enzyme variants are designed and transformed into yeast (design), then synthesized in the yeast where they consume molecules of central metabolism to generate product (build). Using printed droplet microfluidics, they are dispensed to a picoliter well array and subjected to MALDI-MS imaging to quantify the how cell metabolites (test). Principle components analysis clusters cells according to metabolic profile, where each cluster indicates a different phenotype of the enzyme. Desired mutants are extracted from the plate, sequenced, and confirmed in bulk cultures.
Figure 17A:
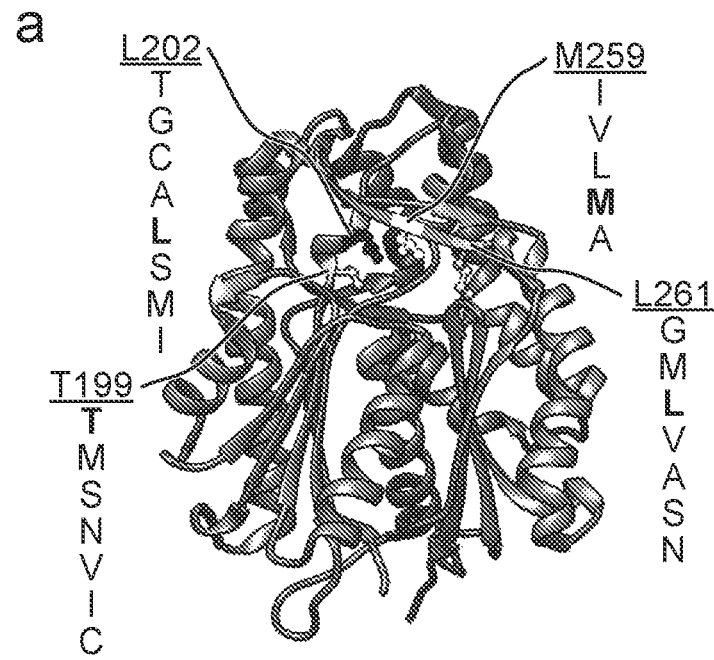
FIG. 17A shows crystal structure of *Gerbera hybrida* G2PS1 (PDB ID: 1EE0) showing the location of the four residues selected for mutagenesis and identity of the residue mutants. All residues except T199 directly form the active site cavity.
Figure 17B:
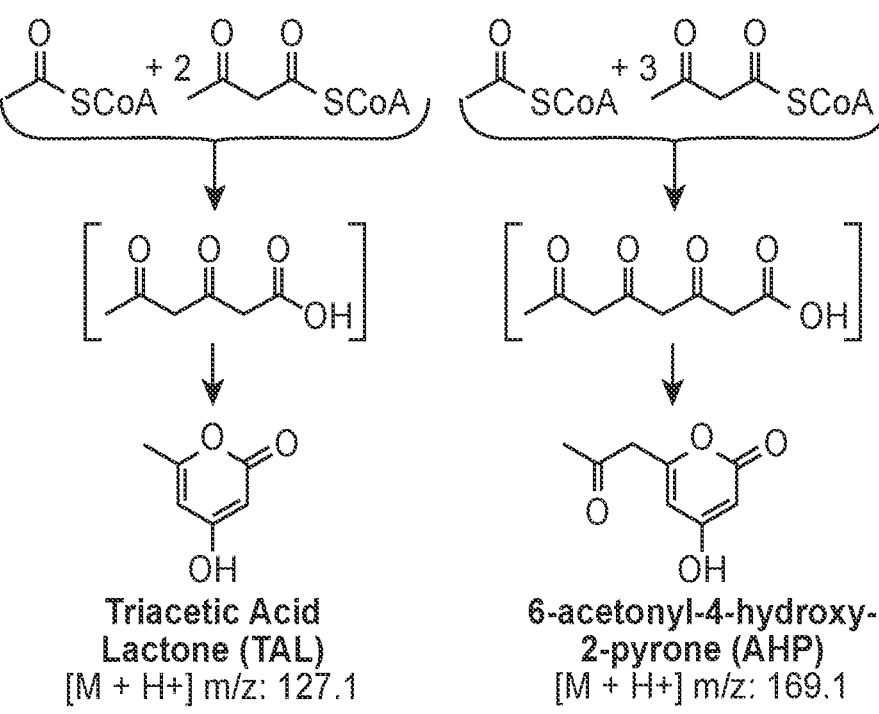
FIG. 17B shows the smallest condensation/cyclization products expected from type III polyketide synthase activity: Triacetic Acid Lactone (TAL, the native product of G2PS1) from one acetyl-CoA and two Malonyl-CoA & 6-Acetonyl-4-Hydroxy-2-Pyrone (AHP) from one acetyl-CoA and three Malonyl-CoA. Higher order polyketides, not shown, are possible from additional condensations of Malonyl-CoA.
Figure 18:
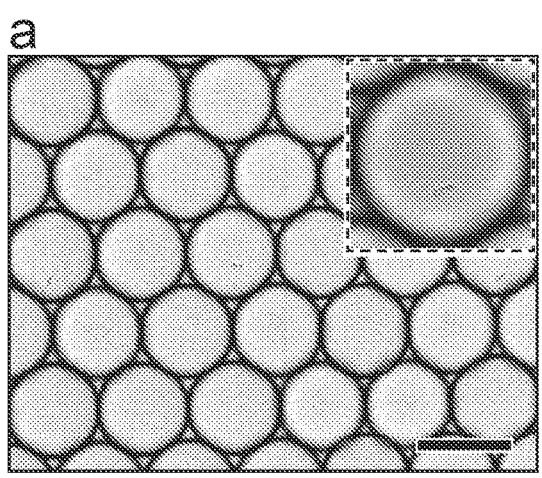
FIG. 18 shows culture Po1g of *Y. lipolytica* in droplets. a, Single cell is encapsulated in the droplets containing culture medium following Poisson distribution in oil. b, After a week incubation in droplets, the single cell forms an isogenic microcolony in the droplet. Scale bar: 100 μm.
Figure 18:
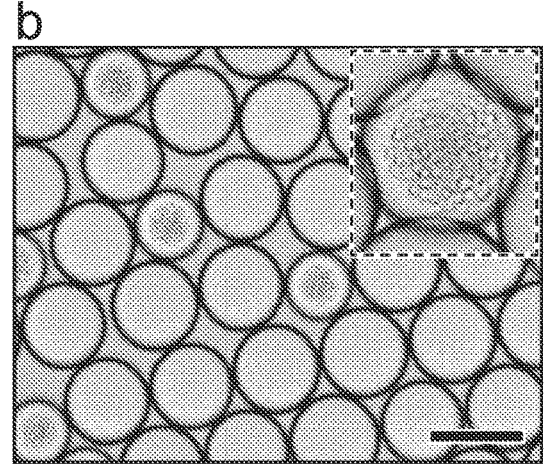
Figure 19:
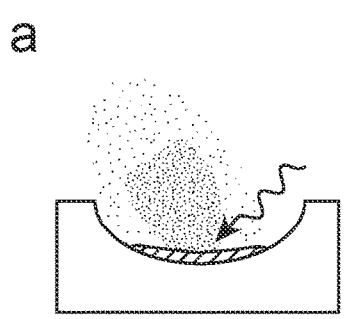
FIG. 19 shows a schematic of how well shape influences the drying pattern of printed material. a, illustrate the drying pattern of the droplet containing cells in the well of bowl-shape. Due to the geometry of the well, all the cells are dried to the center of the well, which facilitate the laser ionization later while in b, for the cylinder-shape well, the cells tends to dry on the walls of the well and prohibit the laser ionization during MALDI MS ion imaging. Scale bar: 50 μm.
Figure 19:
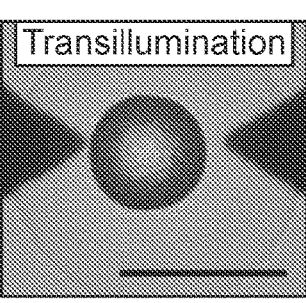
Figure 19:
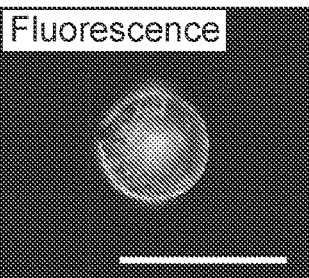
Figure 19:
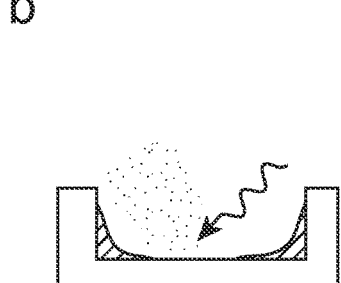
Figure 19:
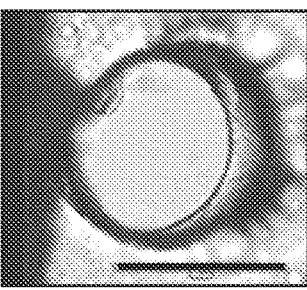
Figure 19:
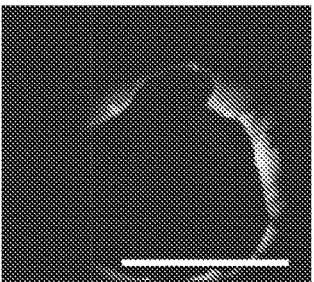
Figures 20, 21:
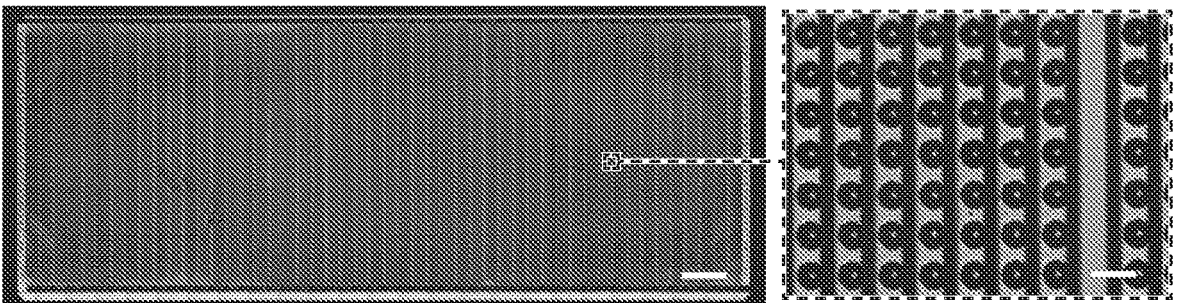
FIG. 20 shows higher capacity well arrays by increased well packing. a, linage of 100,000 well arrays on a 25-by-75 mm microscope slide. Scale bar: 5 mm b, Enlarged image of slide. Scale bar: 100 μm.
FIG. 21 shows setup of the printer droplet microfluidics. Insert is the enlarged view of the print head contains microfluidic channels and optical fibers. Scale bar represents 1 mm.

To demonstrate the utility of the approach, it was applied to a semi-rationally varied 4-position library of the *Gerbera hybrida* G2PS1 type-3 polyketide synthase (t3PKS)6, comprising 1960 codon shuffled members (FIG. 17A). This enzyme is responsible for biosynthesis of triacetic acid lactone (TAL) through the condensation of a starter acetyl-CoA unit with two malonyl-CoA molecules and subsequent cyclization of the triketide chain (Jez, J. M. et al. Chem Biol 7, 919-930 (2000) and Markham, K. A. et al. PNAS 115, 2096-2101 (2018)). Mutations in the active site can alter the kinetics and spectrum of polyketide products formed, potentially accessing unintended products (FIG. 17B). After the library is synthesized and transformed into *Yarrowia lipolytica*, the resultant cells are encapsulated and cultured in 300 pL droplets at tens of kilohertz rates to generate isogenic colonies (FIG. 18); this produces additional cell-material, boosting signal compared to a single cell, and enabling mass spectrometry (MS) characterization and sample clustering (FIG. 15). To perform MS, the droplets were sorted and transferred onto a high-density plate comprising a glass slide etched with 10,000 picoliter wells, with 80 μm diameters and rounded bottoms (FIG. 16A); this shape concentrates the material to the center, allowing accurate matrix assisted laser desorption ionization (MALDI) MS quantitation (FIG. 19). Moreover, the total numbers of wells on one glass slide can be further increased to 100,000 by increasing the well density (FIG. 20).

Figure 22A:
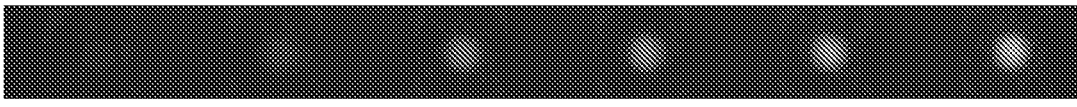
FIG. 22A shows quantification test of the MALDI MS ion imaging of the printed droplet arrays after drying and airbrushing with matrix. a, Image of a slide used for MALDI MS ion imaging after coating with matrix. Scale bar: 2 mm. b, Titration series of triacetic acid lactone (TAL) proportionally mixed with Dextran labeled dye. Purple insert shows magnified fluorescent imaging of droplets. Bottom image is signal intensity heatmap for TAL's 127 mass-to-charge (m/z) signal. Concentration versus signal plot shows a linear response over the tested concentration range. Error bars represent coefficient of variance from the quantification. c, High-magnification picture of nanoarray with printed *Y. lipolytica* colonies. Scale bar represents 2 mm. d, Resultant TAL m/z signal intensity heatmap of a printed population of either empty-vector or G2PS1-expressing *Y. lipolytica* cells. Scale bar represents 500 μm. e, Scatter plot data quantifying TAL level for 300 empty-vector and 300 G2PS1-expressing cells. Black bar represents population mean.
Figure 22A:
Figure 22A:
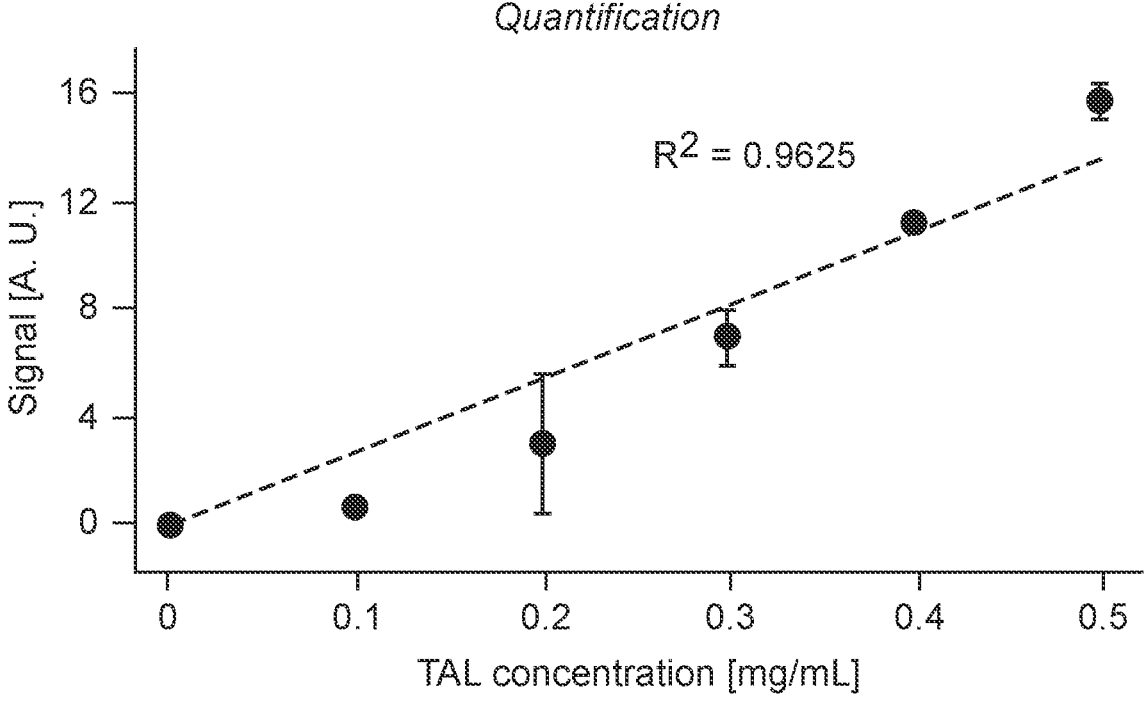
Figure 22B:
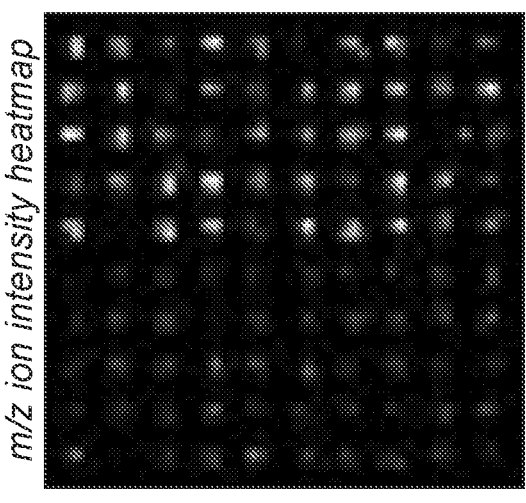
FIG. 22B shows additional data relating to FIG. 22A.
Figure 22B:
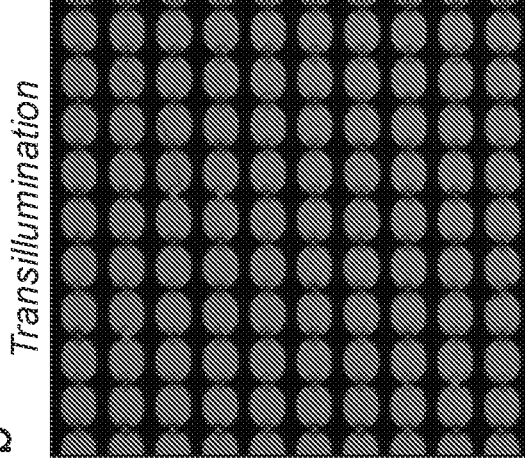
Figure 23:
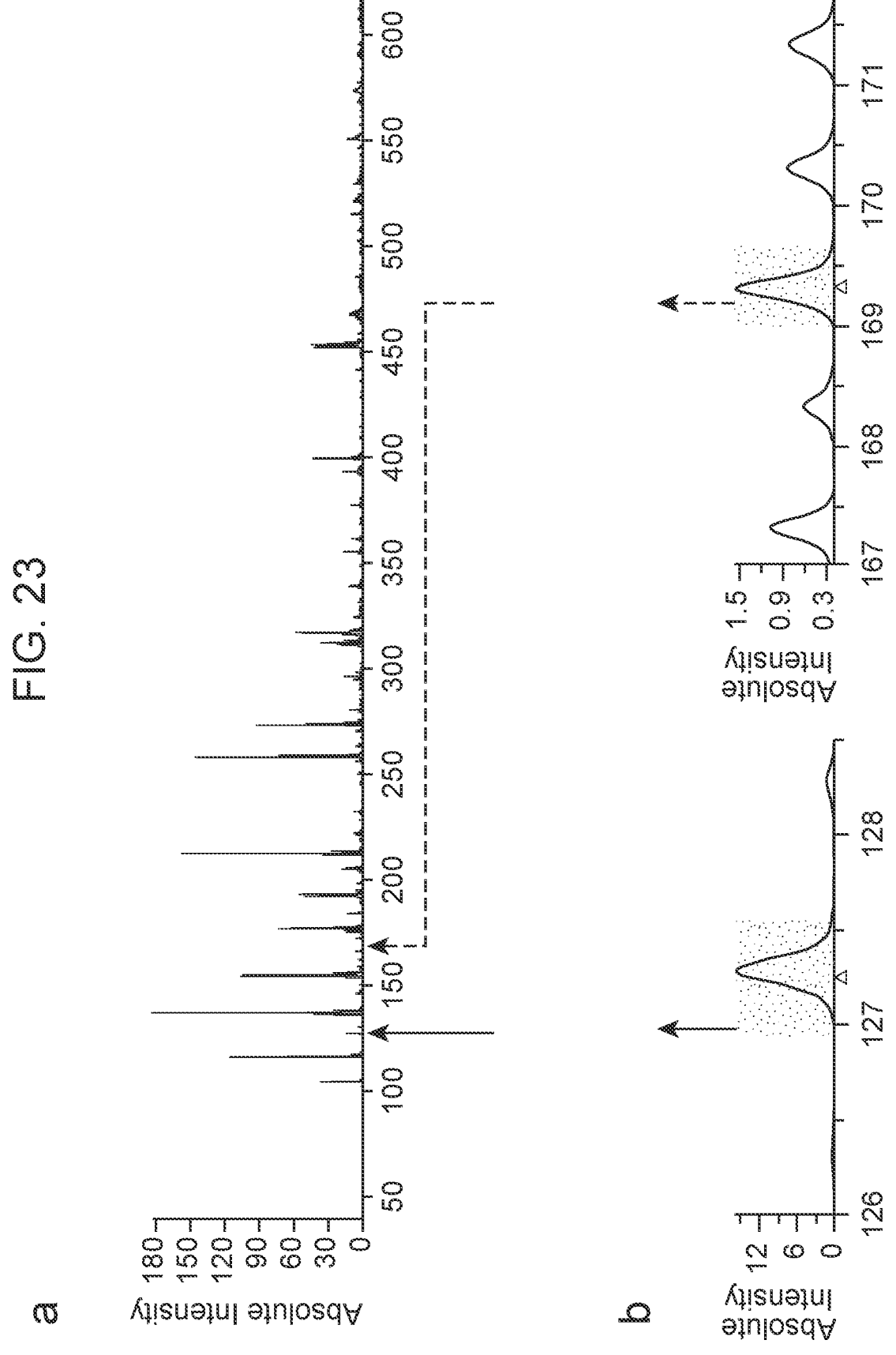
FIG. 23 shows MALDI MS ion imaging of the slide substrate. a, Sum of all mass spectra signals from all the 10,000 wells after total ion normalization and visual through the Bruker SCiLS Lab software. b, By selecting any m/z region with 30 to 630, targeted MS data can be interrogated for 10,000 picowells. As examples, the red insert shows the MS ion image for m/z 127 (corresponding to TAL) and the green insert shows the MS ion image for m/z 169 (corresponding to AHP). c, Ion signal intensity can also be visualized and interrogated across wells. As example, the m/z singal intensities corresponding to likely G2PS1 products were imaged. The top row of each picowell cluster corresponds to printed reference cells, showing an expected formation of TAL product.

To maximize droplet-loading efficiency and throughput, the plate was utilized by implementing printed droplet microfluidics (PDM) (Cole, R. H. et al. PNAS 114, 8728-8733 (2017)) (FIG. 21), a method that allows all wells to be loaded with colonies at a rate of 0.25 seconds/well. PDM also allows pre-screening, to dispense only colonies falling within a narrow density range, ensuring that measured profiles are not skewed by colony density. It also allows specification of where colonies are printed (Cole, R. H. et al. PNAS 114, 8728-8733 (2017), which we use to print 9,000 variants (4.5× coverage of the library) and 1,000 reference strains at known positions. After printing, the plate is dried, spray coated with matrix, and subjected to MALDI-MS imaging (FIG. 22A-B), providing data on all detectable metabolites from 30 to 630 Daltons. The results are reported as an 'image' in which each pixel comprises a 600-dimensional vector of signal amplitudes for each mass-to-charge ratio (m/z) value (FIG. 23). Thus, the data can be thought of as representing a 600 'color' image, in which each slice reports the amplitude of the metabolite corresponding to that m/z. Importantly, MALDI's soft ionization preserves DNA in the well, such that PCR recovery of constructs is possible after MS analysis (FIG. 24)

Figures 16A, 16B:
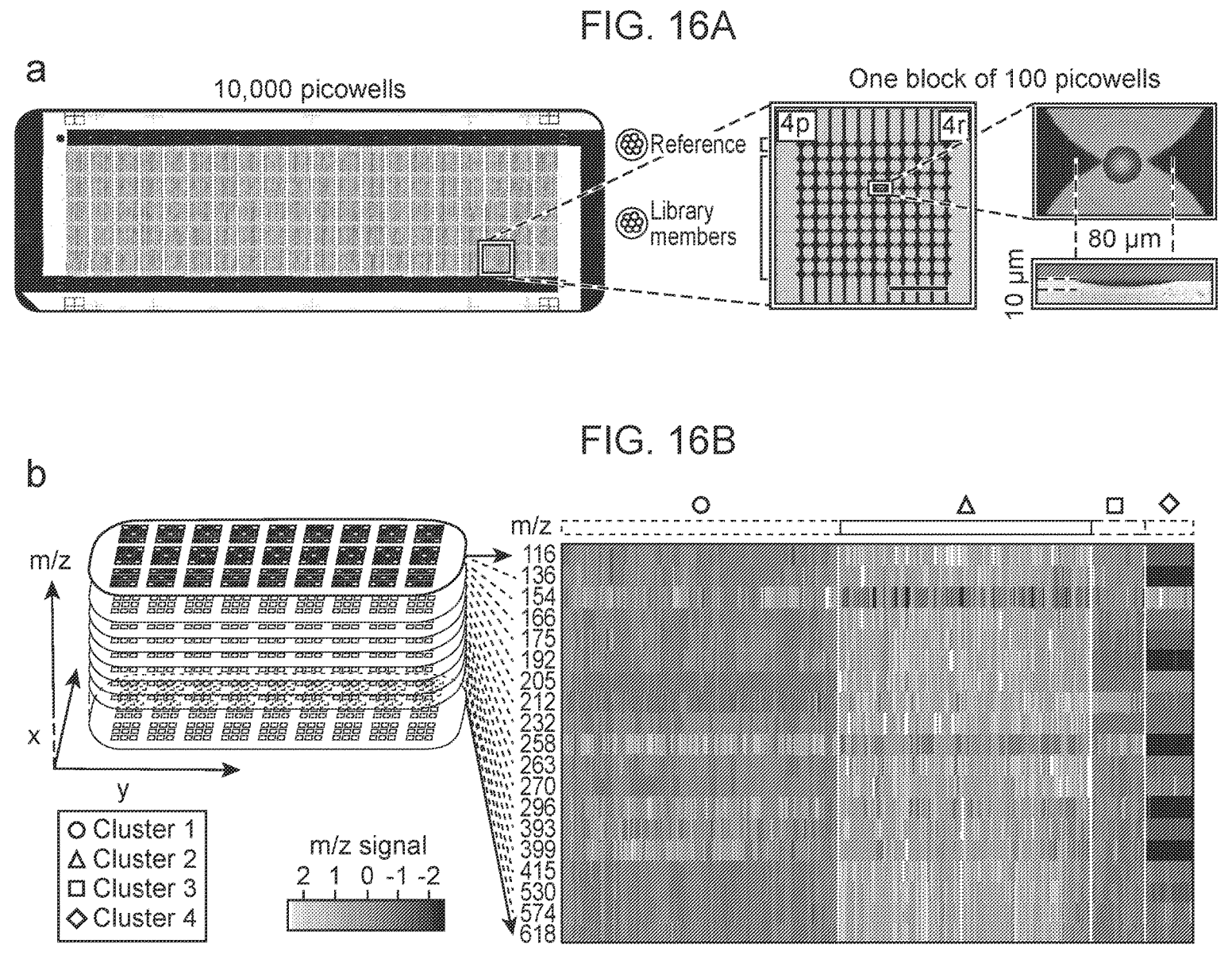
Figure 16C:
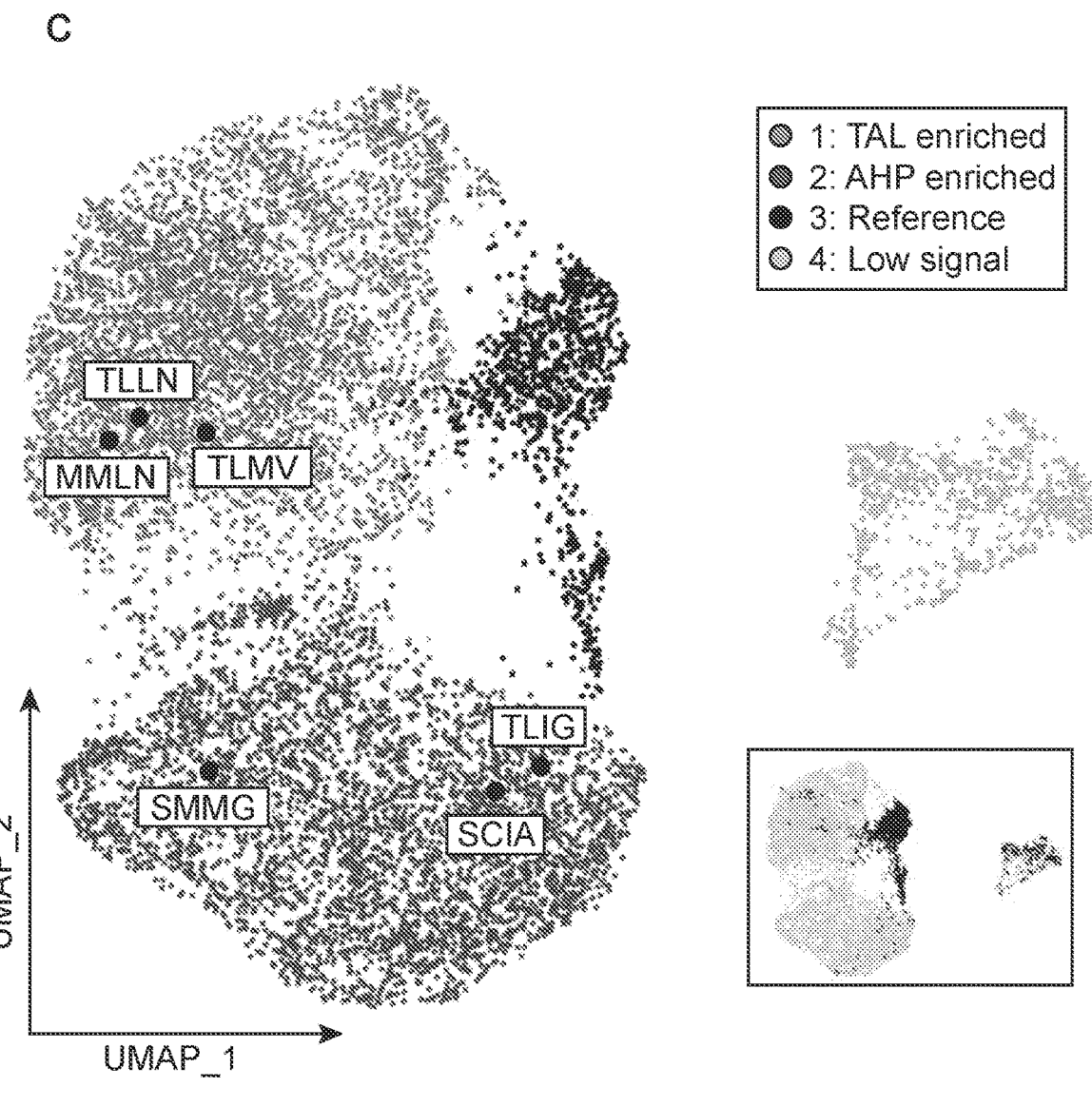
FIG. 16C shows based on the selected m/z peaks in FIG. 16B, umap is plotted. Insert figures show where the reference members are based on the printing locations.

The methods used uniform manifold approximation and projection (UMAP), a dimensionality reduction technique that projects high dimensional data onto a plane while preserving cluster information (Becht, E. et al. Nat Biotechnol 37, 38-44 (2019). To achieve the clearest clusters, the top nineteen m/z values were selected with the highest signal-to-noise ratio and inter-sample variance (FIG. 25, FIG. 16B). From this, four clusters were observed (FIG. 16C) (Si, T. et al. Spectrometry. J. Am. Chem. Soc. 139, 12466-12473 (2017) and Tebani, A. et al. Nature Communications 11, 4487 (2020)).

The compact blue cluster is the 1000 control cells, which was confirmed by well location (FIG. 16C, insert). The gray island of points corresponds to wells with few cells (FIG. 26). This leaves two large clusters (red and green) which were hypothesized to correspond to cells with distinct metabolic profiles. Mapping the m/z 127 data onto the clusters shows that the top red island represents productive TAL mutants (FIG. 16C, top right UMAP). Thus, in addition to the desired product, some mutants generate another product, which is dominantly produced in the lower green cluster. Upon inspecting the MS data more closely, it was determined that a molecule with the m/z value of 169 has differential abundance between these clusters (FIG. 27). Using liquid chromatography and tandem MS, it was confirmed the mass corresponds to the reported alternative product of this enzyme, tetraketide 6-acetonyl-4-hydroxy-2-pyrone (AHP) (Abe et al, J. Am. Chem. Soc. 127, 12709-12716 (2005) and Jindaprasert et al, ytochemistry 69, 3043-3053 (2008)). When the AHP amplitude (m/z 169) was overlaid with the UMAP, it is predominantly found in the green cluster (FIG. 16C, bottom right UMAP).

Figure 16D:
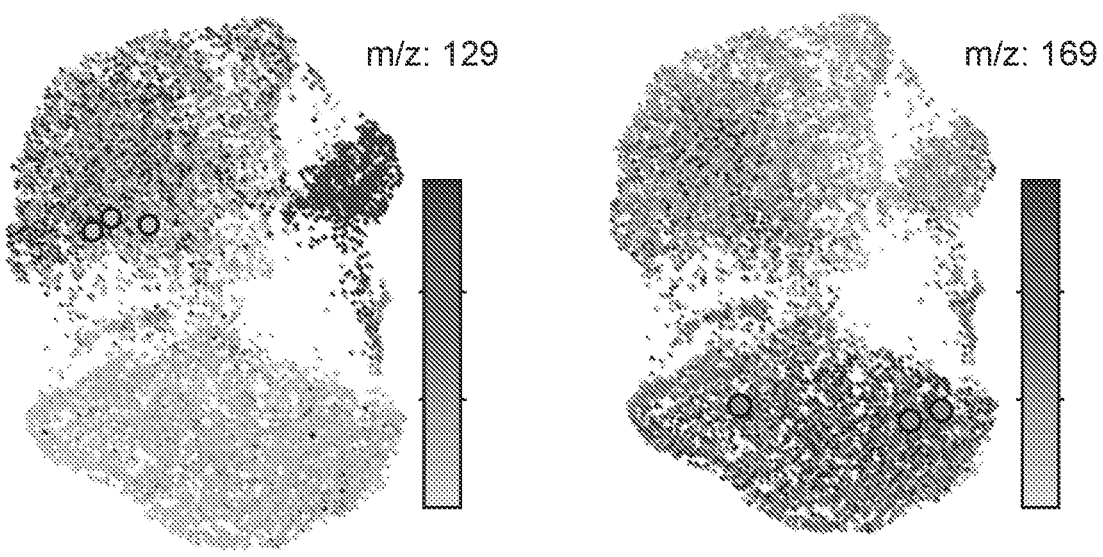
FIG. 16D shows additional data pertaining to FIG. 16C.
Figure 16E:
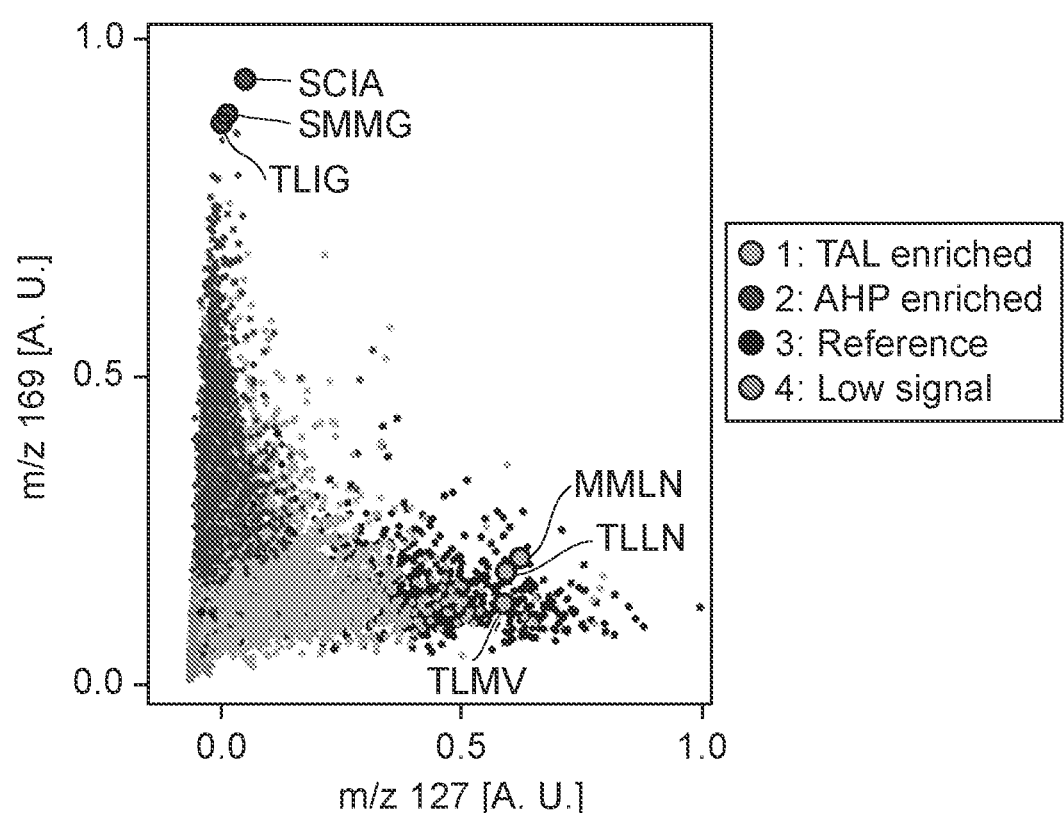
FIG. 16E shows m/z intensity plot for m/z169 vs. m/z 127 overlapped with umap clustering confirmed the identity for each cluster as TAL or AHP enriched respectively. Feature plots of m/z 127 and m/z169
Figure 16F:
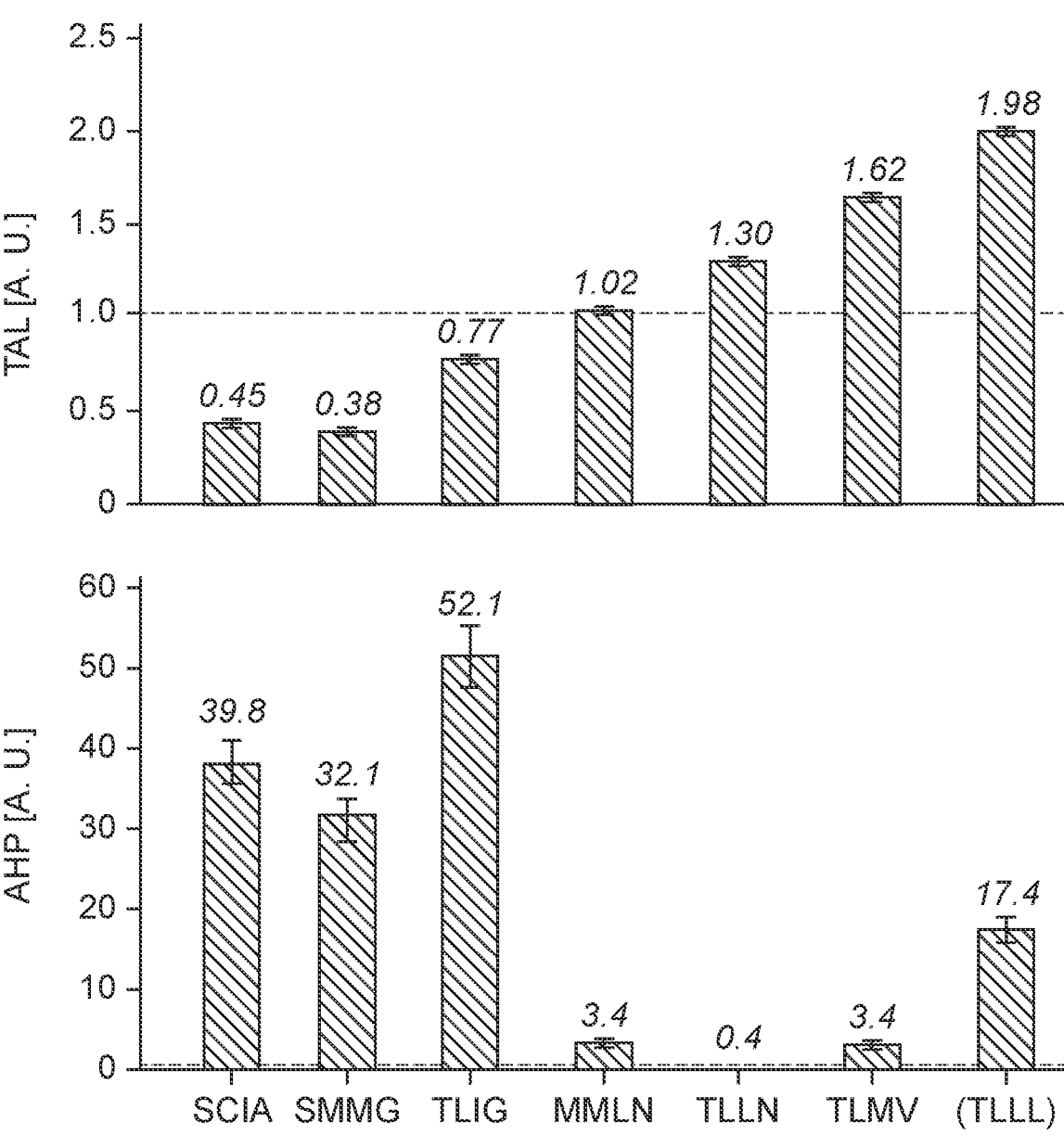
FIG. 16F shows further confirms the clusters are TAL enriched and AHP enriched respectively. The top members for each peak, m/z 169 and m/z 127, are recovered and verified by bulk verification. The figure shows the production level and specificity for the screened winners of TAL and AHP.

To determine any patterns of sequences or sequence relationships between the two library clusters, ~50 mutants were selected and sequenced from each cluster. Plotting the mutants versus normalized TAL and AHP shows colonies with high activity and, generally, that mutants efficient at producing one molecule are inefficient at producing the other (FIG. 16D). To validate these results, eight mutants with highest MS signal of TAL based on MS ion imaging re-transform and test and another eight mutants for APH respectively in bulk, finding good agreement (FIG. 16E, FIG. 28). The TLLL mutant based on consensus analysis of TAL enriched members from the UMAP also shows high TAL production, though it retains higher AHP side-activity than the TLLN mutant (FIG. 16E). These results demonstrate that generation of these products can be inferred from clustering of the host cells' metabolic profiles, even though the peaks associated with these molecules (m/z 127 and 169) are not included in the clustering.

Example 9: Transfer to Replicate Plate for Analysis

In some cases, the droplet is deposited to an addressable location of a substrate, and the mass spectroscopy is performed while the material is still at the addressable location on the substrate. For instance, cells can be grown at the addressable location, and the mass spectroscopy can be performed at that location. However, in some cases, although not all cases, the mass spectroscopy can make it difficult to successfully recover the cells in a living state, or to recover or analyze the omic material, such as genetic material. In some cases there is a need for retransformation or transferring mutations into a fresh background is a time-consuming step that limits platform efficiency. Being able to retain living cultures of high-performing genotypes would accelerate the build-test-design cycle, especially in the context of whole genome mutagenesis of stains for pathway optimization. The aim here is to establish a replica plating infrastructure compatible with the nanoarray that can retain live cells before MALDI-TOF analysis.

As such, an experiment was designed wherein material was transferred from the first plate to a second plate, i.e. from the substrate to a replicate plate. Such a transfer process can be referred to as "replica plating". To implement this approach, both hydrocolloid (pectin or gelatin) and hydrogel (agar) stamping plates can be made from glass slides with the same dimensions as the nanoarray droplet attachment and a customized 3D printed stamping mold will ensure consistent top-down stamping action.

Because transferred volume is determined by the surface tension, the remaining solution within the nanoarray should be uniform with little experimental bias. Feasibility of stamping will be tested using a preestablished pattern of known high and low TAL producing yeast. Droplets will be loaded with respective high or low concentrations of a fluorescent dye to provide a visual reference during printing and post-MALDI inspection. Cell populations will be processed and printed using the protocols developed and stamped against the replica plate prior to MALDI-TOF scanning. Microscopy will be used to confirm droplet transfer and fluorescence differences. The replica plate will be incubated to form microcolonies that will be tested for viability by picking with a toothpick or microneedle and scaling to 0.5 mL liquid cultures.

Materials and Methods

Microfluidic Devices Fabrication

All the microfluidic devices including the printer head, droplet maker and droplet merger are made from poly (dimethylsiloxane) (PDMS) based on the protocols of standard soft lithography. To be more specific: for the printer head a two-layer SU8 master mold is made. The first SU 8 layer or the flow channel layer for droplet reinjection and sorting was made to be 80-μm thick and then a second layer of 20-μm thick SU 8 is added on top of the first layer only at regions where the nozzle channel and optical fiber channel are to accommodate the insertion of the specific diameters of the optical fibers and the printing nozzle. After the master mold is made, uncured PDMS (10:1 polymer to cross-linker ratio) is poured onto the master and cured in an oven at 65° C. for one hour. Then the cured PDMS slab is peeled off and inlet and outlet holes are punched using a 0.75-mm biopsy core. The PDMS casting is then plasma bonded to a 25 mm×75 mm glass slide and baked at 65° C. overnight. One centimeter of PE/5 tubing (Scientific Commodities) as the printing nozzle of the printer head is inserted into the nozzle channel. The assembled printer head is then treated with AquaPel (AquaPel) and air dried. Similarly, the droplet encapsulation device and droplet merger are made from PDMS with a channel height of 70 μm.

Picowell Substrate Fabrication

The picowell substrate is fabricated based on a standard 25 mm×75 mm glass slide. The array consisted of 10,000 picowells arranged in a 200 by 50 format. The diameter and the pitch of the picowells are 100 μm and 250 μm respectively. Below each of the picowells is two sawtooth electrodes pointing each other with a 30 μm gap in between. To make such a picowell substrate, to start deposit a 200-A thick chromium layer on one side of the glass slide by electron sputtering (Huifong Company). Then by photolithography, sawtooth-shape electrode patterns are transferred from the photomask to a layer of 2-μm-thick MA-P 1215 positive photoresist (Micro Resist Technology). Then the glass slide is immersed in Chromium Etchant (Sigma) and washed thoroughly by Acetone, IPA and DI water. After the electrode is made, a 5-μm-thick layer of SU 8 3005 is span on top of the glass slide, baked, UV exposed and developed. Then a second layer of 15-μm-thick SU 8 3025 is span on top and preexposure-baked for 15 mins at 95° C. Then by photolithography (UV power at 200 mJ/cm2) and the alignment of the photomask with fabricated electrodes, patterns of picowells are transferred from the photomask to the second layer of SU 8. After that the coated slide is postexposure-baked at 150° C. for 20 mins and then developed in PGMEA developer (Sigma) for 5 mins. Note here that the timing of UV exposure and postexposure-bake is important to form the bowl-shape profile (concave bottom surface) of the picowells as the special shape of the picowells is formed by diffusion of radicals from the UV exposed region of SU 8 to the unexposed part. The last step is to bake the developed slide again at 95° C. overnight to make sure all the SU 8 is fully linked. All the baking is done on a hot plate.

Yeast Preparation

Engineered yeast strains (*Yarrowia lipolytica*) with varied copy numbers of g2ps1 are used in this study have been reported. Yeasts from a frozen glycerol stock is first inoculated in a culture tube with 2 mL culture medium (20 g/L glucose, 6.7 g/L YNB with ammonium sulfate and 0.79 g/L CSM) for 16 hours at 30° C. The yeasts are then pelleted and resuspended with fresh culture medium. The yeast cells are counted and diluted to $3\times10^7$ cells per mL with fresh culture medium. This cell concentration is chosen to ensure roughly 1 in 10 droplets containing a single yeast cell when encapsulated. Similarly, the engineered yeast strains (*Saccharomyces cerevisiae*) is prepared with its own culture medium.
Yeast in Droplet Culture By coflowing the diluted yeast cell medium and Novec HFE-7500 oil (3M) with 2% EA surfactant using a droplet encapsulation device, 80-μm and 60-μm droplets are formed for *Yarrowia lipolytica* and *Saccharomyces cerevisiae* yeasts respectively. Each of the droplets are collected into a 5 mL syringe (BD) which is then positioned vertically in an incubating shaker for three days at 30° C. to form isogenic microcolonies in droplets. The droplets containing *Yarrowia lipolytica* isogenic microcolonies are ready to use for printing.
Production Induction in Droplet Through Droplet Merging For *Saccharomyces cerevisiae* yeast strain, due to the toxicity of product, two-stage production is designed with galactose induction. To allow this workflow, a different culture medium, production medium, that contains an inducing chemical is introduced into the culture medium after the initial culturing in droplets through droplet merging. The 90-μm droplets containing production medium are prepared by the encapsulation device. Then both of the droplets containing *Saccharomyces cerevisiae* isogenic microcolonies after the initial culturing and the ones containing production medium are reinjected into the droplet merger device along with spacing flows of oil (Novec HFE-7500 oil with 2% EA surfactant). By adjusting flow rates, the two different types of droplets are paired before entering merging channel. By applying an alternating current (AC) voltage (300 V, 58 kHz) to the electrodes close to the flow channel, the production medium droplets are merged into the initial yeast culture droplet. The merged droplets (~110 μm in diameter) are collected into a 5 mL syringe (BD) which is then positioned vertically in an incubating shaker for five days at 30° C. After incubation, the merged droplets containing *Saccharomyces cerevisiae* isogenic microcolonies are ready for printing experiment.
Printer Head Setup and Droplet Sorting An optical setup of the printer head is used here: a multimode excitation fiber with a core diameter of 105 μm and a NA of 0.10 (Thorlabs) is inserted into a guide channel in the printer head. Similarly, an emission detection fiber with core diameter of 105 μm and NA of 0.22 (Thorlabs) is inserted into a second guide channel in the printer head. Four 50 mW continuous wave lasers with wavelengths of 405, 473, 532, and 640 nm are combined and coupled to the excitation fiber. Emitted light is columnated and ported into a quad-bandpass filter, then passed through a series of dichroic mirrors. Bandpass filters of 448, 510, 571, and 697 nm past each dichroic mirror enable wavelength-specific detection of emitted light by four individual PMTs. Electrode channels and a "Faraday moat" is filled with a 5 M NaCl solution. A positive electrode is connected to a function generator and a high voltage amplifier while a second electrode is grounded. Fluidic inputs into the PDM device are driven by syringe pumps (New Era). Bias and spacer oils containing Novec HFE-7500 oil are flowed through the device at a flow rate of 2000 μL/h. A waste channel is driven with a negative flow rate of −3000 μL/h. Droplet with yeast cells prepared previously are reinjected into the device at a flow rate of 100±50 μL/h. Real-time optical signal acquisition through a field programmable gate array (FPGA) (National Instruments) is displayed on a customized LabView software. Optical signal is processed in real time and displayed, so droplets of interest (in this case, with similar numbers of yeast cell inside) can be identified by specifying gates. Controlled by customized LabView software, droplets are subsequently sorted by passing a high frequency pulse through a high voltage amplifier (Trek 690E-6). Typical droplet sorting parameters range from 10 to 20 kHz, 50 to 100 cycles, and 0.5 to 1.0 kV.
Picowell Substrate Setup The picowell substrate is immersed in a bath of Novec HFE7500 oil during printing operation. Copper tape with a conductive adhesive (Ted Pella) is affixed to two electrode contact pads on the picowell slide. One pad is connected to ground, while the other one is connected to a function generator and a high voltage amplifier, providing an electric power at 200-600 V at 20-30 kHz to trap the sorted droplets in the picowells by DEP force.
Printing Procedure During the printing process, the printer head is fixed to a XYZ micromanipulator and the picowell substrate is held on a motorized XY mechanical stage (MA-2000, ASI). The printing process is automated by customized LabView software. The software coordinates the droplet sorting of the printer head and the movement of mechanical stage where the picowell substrate is held. When do printing, the nozzle of the printer head is positioned close enough to the picowell substrate by the XYZ micromanipulator and the picowell substrate is moving from one picowell to next after desired number of droplets are sorted into it. After printing is done, all the bath oil is removed to let the printed picowell substrate dry by passive air convection. Then the substrate is placed in a petri dish and sealed with parafilm and stored at −20° C. until ready to use
Matrix Deposition and MALDI-Mass Spec Imaging A matrix solution of 2,5-Dihydroxybenzoic acid (DHB) is prepared by adding 15 mg/mL DHB into a mixture of 90% ACN and 0.1% TFA in DI water. Then it is feed into an automated matrix sprayer (TM Sprayer, HTX Imaging) and coat the printed picowell substrate with a layer of DHB matrix with a setup of 60° C., flow rate at 0.125 mL/min and velocity at 1200 mm/min. Around 2 mL of matrix solution is used for each substrate. For MALDI-Mass Spec imaging, Bruker Rapiflex is used and the parameter setup for the laser is 50% power, 50 μm spot size and positive mode.
Mass Spec Image Analysis A Bruker flexImaging software is used to analysis the mass spec imaging of the picowell substrate. Based on that, the locations of target picowells are identified automatically by a customized MATLAB program.
Recovery Genome Information from Target Picowells by Glass Micropipette Then a microliquid handler with a 100-μm ID glass micropipette (MPP200B, Bulldog Bio) is used to recover the yeast cells from each of the target picowells and transfer the recovered cells to individual PCR tubes (Fisher Scientific). Primers targeting the g2ps1 gene (5' ATGGGTTCGTATTCGTCTGA and 3' TGACTCGAACGGATCGC from IDT) and PCR reagents (Phire Plant Direct PCR Kit, Fisher Thermo) are added into each of the PCR tubes containing the recovered yeast following the protocols of the PCR kit manufacturer and PCR is performed. Then the sizes of the products from PCR are verified by gel electrophoresis. The sequences are confirmed by Sanger sequencing.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. Moreover, nothing disclosed herein is intended to be dedicated to the public regardless of whether such disclosure is explicitly recited in the claims.

The scope of the present invention, therefore, is not intended to be limited to the exemplary embodiments shown and described herein. Rather, the scope and spirit of present invention is embodied by the appended claims. In the claims, 35 U.S.C. § 112(f) or 35 U.S.C. § 112(6) is expressly defined as being invoked for a limitation in the claim only when the exact phrase "means for" or the exact phrase "step for" is recited at the beginning of such limitation in the claim; if such exact phrase is not used in a limitation in the claim, then 35 U.S.C. § 112 (f) or 35 U.S.C. § 112(6) is not invoked.

What is claimed is:

1. A method, comprising:
encapsulating a biological material in a droplet having a volume of 0.1 nl to 500 nl; depositing the droplet to an addressable location of a substrate; and
performing mass spectroscopy on the droplet;
conducting omics analysis comprising genomic analysis;
wherein the genomic analysis comprises aspirating material at an addressable location and moving it to a genomic analysis device; and
wherein the genomic analysis comprises depositing water at the addressable location, and then aspirating a mixture of the water and a material that was already present at the addressable location and moving a mixture of the water and the material to a genomic analysis device, wherein the genomic analysis comprises polymerase chain reaction (PCR), sequencing DNA, analyzing mRNA, genome-wide profiling of open chromatin region, or DNA methylation sequencing.

2. The method of claim 1, further comprising sorting the droplet before the depositing.

3. The method of claim 2, wherein the sorting is based on a number of cells or density of cells detected in the droplet.

4. The method of claim 1, wherein the biological material is a single cell, further comprising incubating the droplet at a storage location after the encapsulating until the single cell divides into 5 or more isogenic cells, and then conducting the depositing.

5. The method of claim 1, further comprising incubating the biological material after the depositing and before performing of mass spectroscopy.

6. The method of claim 1, further comprising conducting image analysis, fluorescent labeling, or a combination thereof on the droplet after performing mass spectroscopy.

7. The method of claim 1, further comprising conducting the omics analysis on the droplet after performing the mass spectroscopy.

8. The method of claim 7, wherein the omics analysis comprises proteomic analysis, transcriptome analysis, metabolomic analysis, or glycomic analysis.

9. The method of claim 7, further comprising generating a report comparing a mass spectroscopy result and an omics analysis result.

10. The method of claim 1, wherein the biological material is a single cell, two or more cells that are or not genetically identical, contents of a lysed cell, an organoid, or cell free extract.

11. The method of claim 1, wherein the addressable location comprises a well.

12. The method of claim 1, wherein the droplet comprises water during the depositing step and the mass spectroscopy is performed after the water of the droplet has evaporated.

13. The method of claim 1, further comprising adding a reagent to the droplet after the encapsulating but before the depositing.

14. The method of claim 13, wherein the reagent is an enzyme substrate that is capable of being metabolized by an enzyme in the droplet.

15. The method of claim 1, wherein the mass spectroscopy comprises detecting a metabolite generated by the metabolism of the enzyme substrate by the enzyme or wherein the mass spectroscopy is Matrix-Assisted Laser Desorption/Ionization (MALDI) spectroscopy, Desorption Electrospray Ionization (DESI) spectroscopy, Nanostructure-Initiator (NIMS) spectroscopy, or Electrospray Ionization (ESI) spectroscopy.

16. The method of claim 1, wherein the encapsulation involves a cross-junction droplet encapsulation device, a plug-squeeze mechanism, centrifugation, shaking emulsion, or a combination thereof.

17. The method of claim 1, wherein further comprises encapsulating a second biological material in a second droplet having a volume of 0.1 nl to 500 nl, depositing the second droplet to a second addressable location of the substrate, and performing mass spectroscopy on the second droplet.

18. The method of claim 17, further comprising conducting omics analysis on the second droplet after performing mass spectroscopy on the second droplet.

19. The method of claim 18, further comprising generating a report comparing a mass spectroscopy result and an omics analysis result of the droplet with a mass spectroscopy result and an omics analysis result of the second droplet.

20. The method of claim 19, wherein the report indicates that a certain omics result is associated with increased metabolism of an enzyme substrate compared to a different omics result.

21. The method of claim 17, wherein during the encapsulating the first droplet traveled through a microfluidic channel and the second droplet also traveled through the microfluidic channel.

22. The method of claim 17, wherein the time between the first encapsulating and the second encapsulating is 0.001 second to 0.1 second.

23. The method of claim 17, wherein during the depositing the first droplet traveled through a microfluidic channel and the second droplet also traveled through the microfluidic channel.

24. The method of claim 17, wherein the time between the first depositing and the second depositing is 1 second to 5 seconds.

25. The method of claim 17, further comprising selectively conducting omics analysis on either the droplet or the second droplet based on the mass spectroscopy.

26. The method of claim 17, further comprising barcoding the addressable location of the droplet and the second droplet, further comprising conducting genomic on both the droplet and the second droplet.

27. The method of claim 17, wherein the biological material is a cell and the second biological material is a second cell.

28. The method of claim 27, further comprising generating the cell and second cell as part of a mutant library.

29. The method of claim 27, wherein the cell and the second cell differ at a genetic region that corresponds to an enzyme.

30. The method of claim 17, further comprising adding an enzyme substrate to the droplet and the second droplet, wherein at least one variation of the enzyme is capable of metabolizing the enzyme substrate.

31. The method of claim 17, comprising:

generating 20 droplets having a volume of 0.1 nl to 500 nl, wherein at least one droplet has a single cell encapsulated therein and at least one droplet has zero cells;

detecting the number of cells in each of the 20 droplets; and sorting the 20 droplets such that each droplet with a single cell is deposited to a different addressable location on the substrate and other droplets are recycled or directed to a waste container.

32. The method of claim 31, comprising encapsulating 500 cells in 500 droplets each having a volume of 0.1 nl to 500 nl, depositing the 500 droplets to 500 addressable locations of the substrate, and performing mass spectroscopy on the 500 droplets.

33. The method of claim 32, comprising selectively conducting genomic analysis on 1 to 499 of the droplets based on the mass spectroscopy.

34. The method of claim 33, comprising barcoding the 500 addressable locations of the 500 droplets, further comprising conducting genomic analysis on the 500 droplets.

35. The method of claim 32, comprising encapsulating 10,000 cells in 10,000 droplets each having a volume of 0.1 nl to 1 nl, depositing the 10,000 droplets to 10,000 addressable locations of the substrate, and performing mass spectroscopy on the 10,000 droplets.

36. The method of claim 35, comprising selectively conducting omics analysis on 1 to 9,999 of the droplets based on the mass spectroscopy.

37. The method of claim 35, comprising barcoding the 10,000 addressable locations of the 10,000 droplets, further comprising conducting omics analysis on the 10,000 droplets.

38. The method of claim 35, wherein the density of the addressable locations on the substrate is 100 per $cm^2$ to 10,000 per $cm^2$.

39. The method of claim 35, wherein the substrate has a surface area of 80 $cm^2$ or less.

40. A system, comprising:

a substrate comprising addressable locations;

a microfluidic device configured to encapsulate a biological material in a droplet having a volume of 10 nl to 500 nl and deposit the droplet to one of the addressable locations; a mass spectrometer; and an omics analysis device; and wherein genomic analysis comprises depositing water at one of the addressable locations, and then aspirating a mixture of water and a material that was already present at the addressable location and moving the mixture of the water and the material to the omics analysis device, wherein the genomic analysis comprises polymerase chain reaction (PCR), sequencing DNA, analyzing mRNA, genome-wide profiling of open chromatin region, or DNA methylation sequencing.

41. A method, comprising:

encapsulating 10 to 1000 enzymes in separate droplets;

depositing the 10 to 1000 droplets to separate addressable locations of one or more substrates;

performing mass spectroscopy on the 10 to 1000 droplets, thereby generating mass spectroscopy data;

conducting cluster analysis on the mass spectroscopy data, thereby identifying two or more clusters; and wherein genomic analysis comprises depositing water at one of the addressable locations, and then aspirating a mixture of water and a material that was already present at the addressable location and moving the mixture of the water and the material to an omics analysis device, wherein the genomic analysis comprises polymerase chain reaction (PCR), sequencing DNA, analyzing mRNA, genome-wide profiling of open chromatin region, or DNA methylation sequencing.

* * * * *